US012595496B2

(12) United States Patent
Schirmer et al.

(10) Patent No.: US 12,595,496 B2
(45) Date of Patent: Apr. 7, 2026

(54) ENZYMATIC BIOSYNTHESIS OF LACTONES

(71) Applicant: Genomatica, Inc., San Diego, CA (US)

(72) Inventors: Andreas W. Schirmer, Hayward, CA (US); Katherine Ann Murphy, San Diego, CA (US); Angelica Zabala Bautista, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 962 days.

(21) Appl. No.: 17/420,908

(22) PCT Filed: Jan. 15, 2020

(86) PCT No.: PCT/US2020/013696

§ 371 (c)(1),
(2) Date: Jul. 6, 2021

(87) PCT Pub. No.: WO2020/150362

PCT Pub. Date: Jul. 23, 2020

(65) Prior Publication Data

US 2022/0064684 A1 Mar. 3, 2022

Related U.S. Application Data

(60) Provisional application No. 62/794,497, filed on Jan. 18, 2019.

(51) Int. Cl.
*C12P 17/06* (2006.01)
*C12N 9/00* (2006.01)
*C12N 9/16* (2006.01)

(52) U.S. Cl.
CPC ................ *C12P 17/06* (2013.01); *C12N 9/16* (2013.01); *C12N 9/93* (2013.01); *C12Y 301/0202* (2013.01); *C12Y 602/01003* (2013.01)

(58) Field of Classification Search
CPC .. C12P 17/06; C12N 9/16; C12N 9/93; C12Y 301/0202; C12Y 602/01003
See application file for complete search history.

(56) References Cited

U.S. PATENT DOCUMENTS

| | | | |
|---|---|---|---|
| 2017/0029854 | A1 | 2/2017 | Del Cardayre et al. |
| 2017/0044551 | A1 | 2/2017 | Chokhawala |
| 2018/0135059 | A1 | 5/2018 | Gonzalez et al. |

FOREIGN PATENT DOCUMENTS

| | | | |
|---|---|---|---|
| WO | 2016168708 | A1 | 10/2016 |
| WO | WO-2016176347 | A1 | 11/2016 |

OTHER PUBLICATIONS

Kizer L et al. Application of Functional Genomics to Pathway Optimization for Increased Isoprenoid Production. 2008. Applied and Environmental Microbiology. p. 3229-3241. (Year: 2008).*

Prather KLJ et al. De novo biosynthetic pathways: rational design of microbial chemical factories. 2008. Current Opinion in Biotechnology. 19:468-474. (Year: 2008).*

Singh RK et al. Protein Engineering Approaches in the Post-Genomic Era. 2017. Current Protein and Peptide Science. 18, 1-11. (Year: 2017).*

Zhang M et al. Propagated Perturbations from a Peripheral Mutation Show Interactions Supporting WW Domain Thermostability. 2018. Structure. 26, 1474-1485. (Year: 2018).*

International Preliminary Report on Patentability from corresponding PCT Application No. PCT/US2020/013696 dated Jun. 16, 2021.

Extended European Search Report from corresponding European Application No. 20742120.7 dated Oct. 13, 2022.

International Search Report from corresponding PCT Application No. PCT/US2020/013696 dated Apr. 21, 2020.

Written Opinion from corresponding PCT Application No. PCT/US2020/013696 dated Apr. 21, 2020.

Zhuang, Z., et al., "The YbgC protein encoded by the ybgC gene of the tol-pal gene cluster of Haemophilus influenzae catalyzes acyl-coenzyme A thioester hydrolysis," FEBS Letters, 516: 161-163 (2002).

Kim, Y., et al., "Chain A, Protein Ybgc." National Center for Biotechnology Information, Genbank Entry (2004).

* cited by examiner

*Primary Examiner* — Paul J Holland
(74) *Attorney, Agent, or Firm* — Harness Dickey & Pierce P.L.C.

(57) ABSTRACT

The disclosure relates to methods for the production of natural lactones by bacteria under physiological conditions. The methods employ ybgC proteins having lactonizing activity.

18 Claims, 17 Drawing Sheets

Specification includes a Sequence Listing.

Oleochemical 12-hydroxyoctadecanonoic acid 12-hydroxyoctadecanoyl-CoA 10-hydroxyhexadecanoyl-CoA 8-hydroxytetradecanoyl-CoA 6-hydroxydodecanoyl-CoA 4-hydroxydecanoyl-CoA Natural γ-decalactone Non-natural γ-decalactone glucose decanoyl-acyl carrier protein decanoic acid 4-hydroxydecanoic acid 4-hydroxyacyl-CoA γ-decalactone glucose cis-9-hexadecenoyl-acyl carrier protein palmitoleic acid 10-hydroxyhexadecanoic acid 10-hydroxyhexadecanoyl-CoA 4-hydroxydecanoyl-CoA γ-decalactone

δ-decalactone standard

ENZYMATIC BIOSYNTHESIS OF LACTONES

CROSS REFERENCE TO RELATED PATENT APPLICATIONS

This application is a national stage application under 35 U.S.C. § 371 of International Application No. PCT/US2020/013696, which has an international filing date of 15 Jan. 2020 and claims the benefit of U.S. Provisional Application No. 62/794,497, filed on 18 Jan. 2019. The contents of each application recited above is incorporated herein by reference in its entirety.

FIELD

The disclosure relates to the field of specialty chemicals and methods for their synthesis. The disclosure provides bacteria engineered to produce lactones in vivo at neutral pH. Accordingly, the disclosure provides biochemical pathways, recombinant microorganisms and methods for the biological production of various lactones.

BACKGROUND

Lactones are cyclic esters and are components of many flavors and fragrances. Flavors and fragrances are integral components of a wide range of consumer goods.

There is an increasing demand for natural flavor and fragrance ingredients to satisfy increasing demand in e.g., the food, beverage, fragrance and cosmetics industries.

Increasing demand for natural flavors and fragrances, requires that new methods be developed to meet this increasing demand. To be natural, compounds have to result from the extraction of natural materials and/or to be transformed by natural means e.g., through the use of enzymes or whole cells (see e.g., EFFA Guidance Document for the Production of Natural Flavouring Substances and (Natural) Flavouring Preparations in the EU).

Thus, natural lactones containing 8 to 14 carbon atoms, such as e.g. γ-decalactone or δ-dodecalactone, can be extracted from their natural sources, e.g. from fruits like peach, strawberry or pineapple. Natural lactones can also be prepared from microbial cells e.g., from yeast see e.g., However, biotechnological processes that involve a chemical conversion step e.g. the bioconversion of ricinoleic acid or other oleochemcials using certain yeast strains (see e.g., Sushilkumar et al., 2008 Advanced Biotech, p. 20-30; Kourist and Hilterhaus 2015, p. 275-301, in Microorganisms in Biorefineries, B. Kamm (ed.), Springer Verlag), disqualifies the lactone product from being marketed and sold as natural flavor (see e.g., EFFA Guidance Document supra).

Therefore, what is needed in the art are processes for the production of natural lactones e.g., γ-, δ- and/or ε-lactones that meet strict requirements for manufacturing of natural flavors.

Fortunately, as will be clear from the detailed description that follows, the present disclosure provides for this and other needs.

SUMMARY

In one aspect the disclosure provides a method for enzymatically producing a lactone under physiological conditions, the method comprising: culturing a recombinant bacterium that heterologously expresses a YbgC protein and an acyl-CoA synthetase protein, in a culture medium having a neutral pH, wherein the heterologously expressed YbgC protein converts an hydroxy acyl-CoA substrate to a lactone, and wherein the hydroxyl acyl-CoA substrate is a member selected from: a 4-hydroxy acyl-CoA; a 5-hydroxy acyl-CoA and a 6-hydroxy acyl-CoA, and wherein the heterologously expressed YbgC protein converts the 4-hydroxy acyl-CoA to a γ-lactone; the heterologously expressed YbgC protein converts the 5-hydroxy acyl-CoA to a 8-lactone and the heterologously expressed YbgC protein converts the 6-hydroxy acyl-CoA, to an &-lactone.

In embodiments, the heterologously expressed YbgC protein is overexpressed.

In embodiments, the hydroxy acyl-CoA substrate is produced by the recombinant bacterium from a fatty acid derivative molecule exogenously added to the culture medium. In embodiments, the fatty acid derivative molecule exogenously added to the culture medium is a 4-hydroxy fatty acid derivative, a 5-hydroxyl fatty acid derivative or a 6-hydroxy fatty acid derivative. In embodiments, the fatty acid derivative molecule exogenously added to the culture medium is a 4-hydroxy fatty acid derivative and the recombinant bacterium produces the 4-hydroxy acyl-CoA from the 4-hydroxy fatty acid derivative. In embodiments, the 4-hydroxy fatty acid derivative is 4-hydroxy decanoic acid.

In embodiments, the recombinant bacterium produces the 5-hydroxy acyl-CoA from the 5-hydroxyl fatty acid derivative exogenously added to the culture medium. In embodiments, the 5-hydroxy fatty acid derivative exogenously added to the culture medium is 5-hydroxy decanoic acid.

In embodiments, the recombinant bacterium produces 6-hydroxy acyl-CoA from the 6-hydroxy fatty acid derivative exogenously added to the culture medium. In embodiments, the 6-hydroxy fatty acid derivative is 6-hydroxy hexanoic acid.

In embodiments, the heterologously expressed YbgC protein used in the method for enzymatically producing a lactone under physiological conditions wherein the fatty acid derivative molecule is exogenously added to the culture medium has at least 60% sequence identity to SEQ ID NO: 1 over the full length of the YbgC amino acid sequence.

In embodiments, the heterologously expressed YbgC protein used in the method for enzymatically producing a lactone under physiological conditions wherein the fatty acid derivative molecule is exogenously added to the culture medium has at least 70% sequence identity to SEQ ID NO:1 over the full length of the YbgC amino acid sequence.

In embodiments, the heterologously expressed YbgC protein used in the method for enzymatically producing a lactone under physiological conditions wherein the fatty acid derivative molecule is exogenously added to the culture medium has at least 75% sequence identity to SEQ ID NO: 1 over the full length of the YbgC amino acid sequence.

In embodiments, the heterologously expressed YbgC protein used in the method for enzymatically producing a lactone under physiological conditions wherein the fatty acid derivative molecule is exogenously added to the culture medium has at least 80% sequence identity to SEQ ID NO: 1 over the full length of the YbgC amino acid sequence.

In embodiments, the heterologously expressed YbgC protein used in the method for enzymatically producing a lactone under physiological conditions wherein a a fatty acid derivative molecule is exogenously added to the culture medium has at least 85% sequence identity to SEQ ID NO: 1 over the full length of the YbgC amino acid sequence.

In embodiments, the heterologously expressed YbgC protein used in the method for enzymatically producing a lactone under physiological conditions wherein the fatty acid derivative molecule is exogenously added to the culture medium has at least 90% sequence identity to SEQ ID NO: 1 over the full length of the YbgC amino acid sequence.

In embodiments, the heterologously expressed YbgC protein used in the method for enzymatically producing a lactone under physiological conditions wherein the fatty acid derivative molecule is exogenously added to the culture medium has at least 95% sequence identity to SEQ ID NO: 1 over the full length of the YbgC amino acid sequence.

In embodiments, the heterologously expressed YbgC protein used in the method for enzymatically producing a lactone under physiological conditions wherein the fatty acid derivative molecule is exogenously added to the culture medium is SEQ ID NO: 1.

In embodiments, the heterologously expressed YbgC protein that has at least 60% sequence identity to SEQ ID NO: 1 over the full length of the YbgC amino acid sequence that is used in the method for enzymatically producing a lactone under physiological conditions wherein the fatty acid derivative molecule is exogenously added to the culture medium is selected from the group consisting of: *Escherichia coli* ybgC (SEQ ID NO: 1); *Citrobacter koseri* ybgC (SEQ ID NO:2); *Enterobacter cloacae* ybg ((SEQ ID NO: 3); *Serratia fonticola* ybgC (SEQ ID NO:4); *Exiguobacterium mexicanum* ybgC (SEQ ID NO: 5) and *Plesiomonas shigelloides* ybgC (SEQ ID NO:6).

In one aspect the disclosure provides a method for enzymatically producing a lactone under physiological conditions, the method comprising: culturing a recombinant bacterium that heterologously expresses a YbgC protein, an acyl-CoA synthetase protein, a thioesterase and an hydroxylating enzyme, in a culture medium having a neutral pH, wherein the heterologously expressed YbgC protein converts an hydroxy acyl-CoA substrate to a lactone, and wherein the hydroxyl acyl-CoA substrate is a member selected from: a 4-hydroxy acyl-CoA; a 5-hydroxy acyl-CoA and a 6-hydroxy acyl-CoA, and wherein the heterologously expressed YbgC protein converts the 4-hydroxy acyl-CoA to a γ-lactone; the heterologously expressed YbgC protein converts the 5-hydroxy acyl-CoA to a δ-lactone and the heterologously expressed YbgC protein converts the 6-hydroxy acyl-CoA, to an ε-lactone.

In embodiments, the thioesterase is a member selected from SEQ ID NO: 16, SEQ ID NO:17, SEQ ID NO:18, SEQ ID NO:19, SEQ ID NO:20, SEQ ID NO:21, SEQ ID NO: 22, SEQ ID NO:23 and SEQ ID NO:24, and the hydroxylating enzyme is a member selected from SEQ ID NO:25, SEQ ID NO:26, SEQ ID NO:27, SEQ ID NO:28, SEQ ID NO: 29, SEQ ID NO:30 and SEQ ID NO:31.

In embodiments, the recombinant bacterium produces the lactone from a simple carbon source.

In embodiments, the heterologously expressed YbgC protein used in the method for enzymatically producing a lactone under physiological conditions from a simple carbon source, wherein the method comprises culturing a recombinant bacterium that heterologously expresses a YbgC protein, an acyl-CoA synthetase protein, a thioesterase and an hydroxylating enzyme, in a culture medium having a neutral pH, has at least 60% sequence identity to SEQ ID NO: 1 over the full length of the YbgC amino acid sequence.

In embodiments, the heterologously expressed YbgC protein used in the method for enzymatically producing a lactone under physiological conditions from a simple carbon source, wherein the method comprises culturing a recombinant bacterium that heterologously expresses a YbgC protein, an acyl-CoA synthetase protein, a thioesterase and an hydroxylating enzyme, in a culture medium having a neutral pH, has at least 70% sequence identity to SEQ ID NO: 1 over the full length of the YbgC amino acid sequence.

In embodiments, the heterologously expressed YbgC protein used in the method for enzymatically producing a lactone under physiological conditions from a simple carbon source, wherein the method comprises culturing a recombinant bacterium that heterologously expresses a YbgC protein, an acyl-CoA synthetase protein, a thioesterase and an hydroxylating enzyme, in a culture medium having a neutral pH, has at least 75% sequence identity to SEQ ID NO: 1 over the full length of the YbgC amino acid sequence.

In embodiments, the heterologously expressed YbgC protein used in the method for enzymatically producing a lactone under physiological conditions from a simple carbon source, wherein the method comprises culturing a recombinant bacterium that and an hydroxylating enzyme, in a culture medium having a neutral pH, has at least 80% sequence identity to SEQ ID NO: 1 over the full length of the YbgC amino acid sequence.

In embodiments, the heterologously expressed YbgC protein used in the method for enzymatically producing a lactone under physiological conditions from a simple carbon source, wherein the method comprises culturing a recombinant bacterium that heterologously expresses a YbgC protein, an acyl-CoA synthetase protein, a thioesterase and an hydroxylating enzyme, in a culture medium having a neutral pH, has at least 85% sequence identity to SEQ ID NO: 1 over the full length of the YbgC amino acid sequence.

In embodiments, the heterologously expressed YbgC protein used in the method for enzymatically producing a lactone under physiological conditions from a simple carbon source, wherein the method comprises culturing a recombinant bacterium that heterologously expresses a YbgC protein, an acyl-CoA synthetase protein, a thioesterase and an hydroxylating enzyme, in a culture medium having a neutral pH, has at least 90% sequence identity to SEQ ID NO:1 over the full length of the YbgC amino acid sequence.

In embodiments, the heterologously expressed YbgC protein used in the method for enzymatically producing a lactone under physiological conditions from a simple carbon source, wherein the method comprises culturing a recombinant bacterium that heterologously expresses a YbgC protein, an acyl-CoA synthetase protein, a thioesterase and an hydroxylating enzyme, in a culture medium having a neutral pH, has at least 95% sequence identity to SEQ ID NO: 1 over the full length of the YbgC amino acid sequence.

In embodiments, the heterologously expressed YbgC protein used in the method for enzymatically producing a lactone under physiological conditions from a simple carbon source, wherein the method comprises culturing a recombinant bacterium that heterologously expresses a YbgC protein, an acyl-CoA synthetase protein, a thioesterase and an hydroxylating enzyme, in a culture medium having a neutral pH, is SEQ ID NO:1.

In embodiments, the heterologously expressed YbgC protein used in the method for enzymatically producing a lactone under physiological conditions from a simple carbon source, wherein the method comprises culturing a recombinant bacterium that and an hydroxylating enzyme, in a culture medium having a neutral pH, that has at least 60% sequence identity to SEQ ID NO: 1 over the full length of the YbgC amino acid sequence is a member selected from the group consisting of: *Escherichia coli* ybgC (SEQ ID NO: 1); *Citrobacter koseri* ybgC (SEQ ID NO:2); *Enterobacter cloacae* ybgC (SEQ ID NO: 3); *Serratia fonticola* ybgC (SEQ ID NO:4); *Exiguobacterium mexicanum* ybgC (SEQ ID NO: 5) and *Plesiomonas shigelloides* ybgC (SEQ ID NO:6).

Other features, objects and advantages of the invention will be apparent from the detailed description which follows.

DETAILED DESCRIPTION

Definitions

Figure 1:
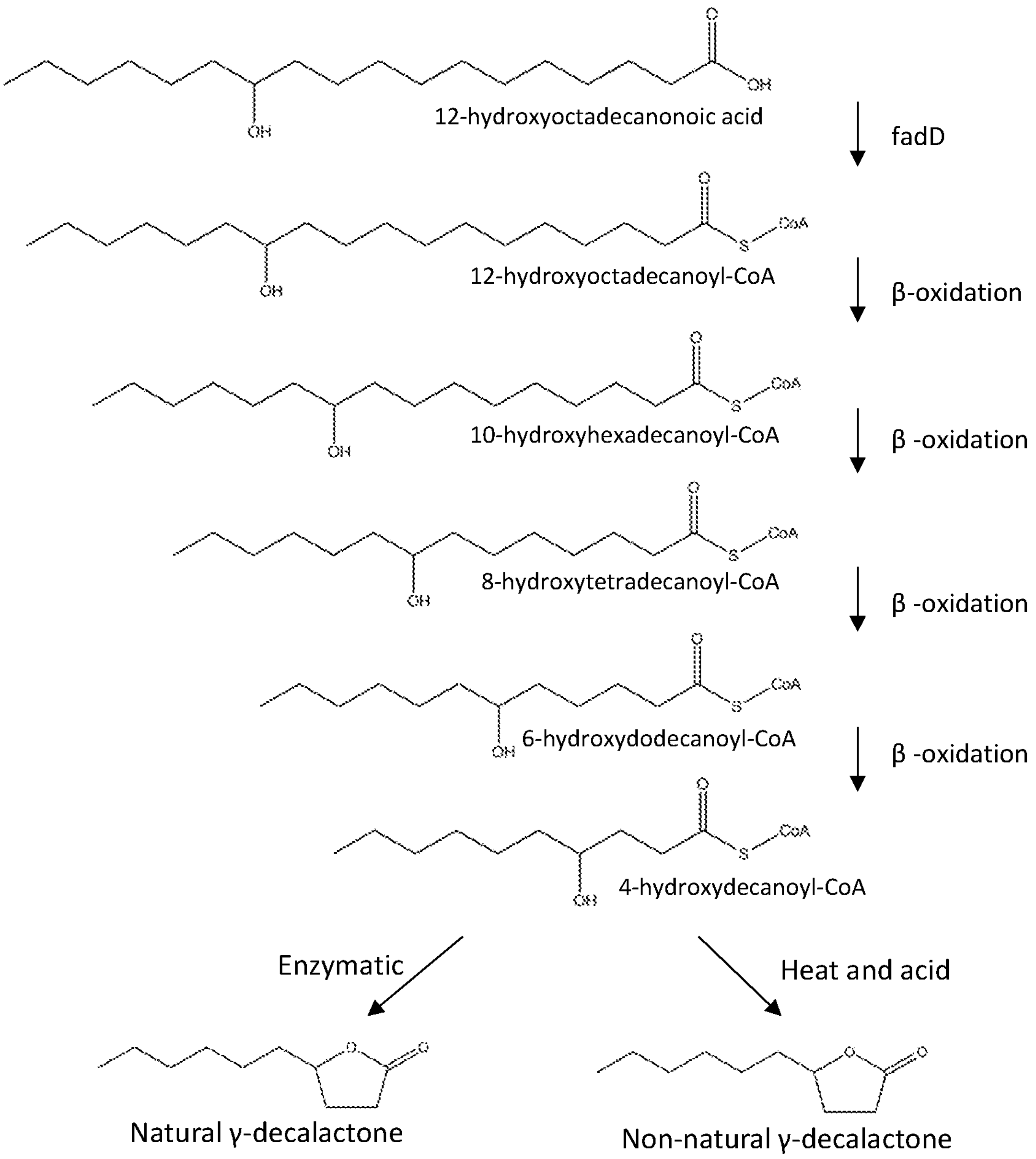
FIG. 1 Illustrates a biochemical pathway converting an oleochemcial to γ-decalactone. When the last step is carried out enzymatically, the product is natural γ-decalactone.
Figure 2:
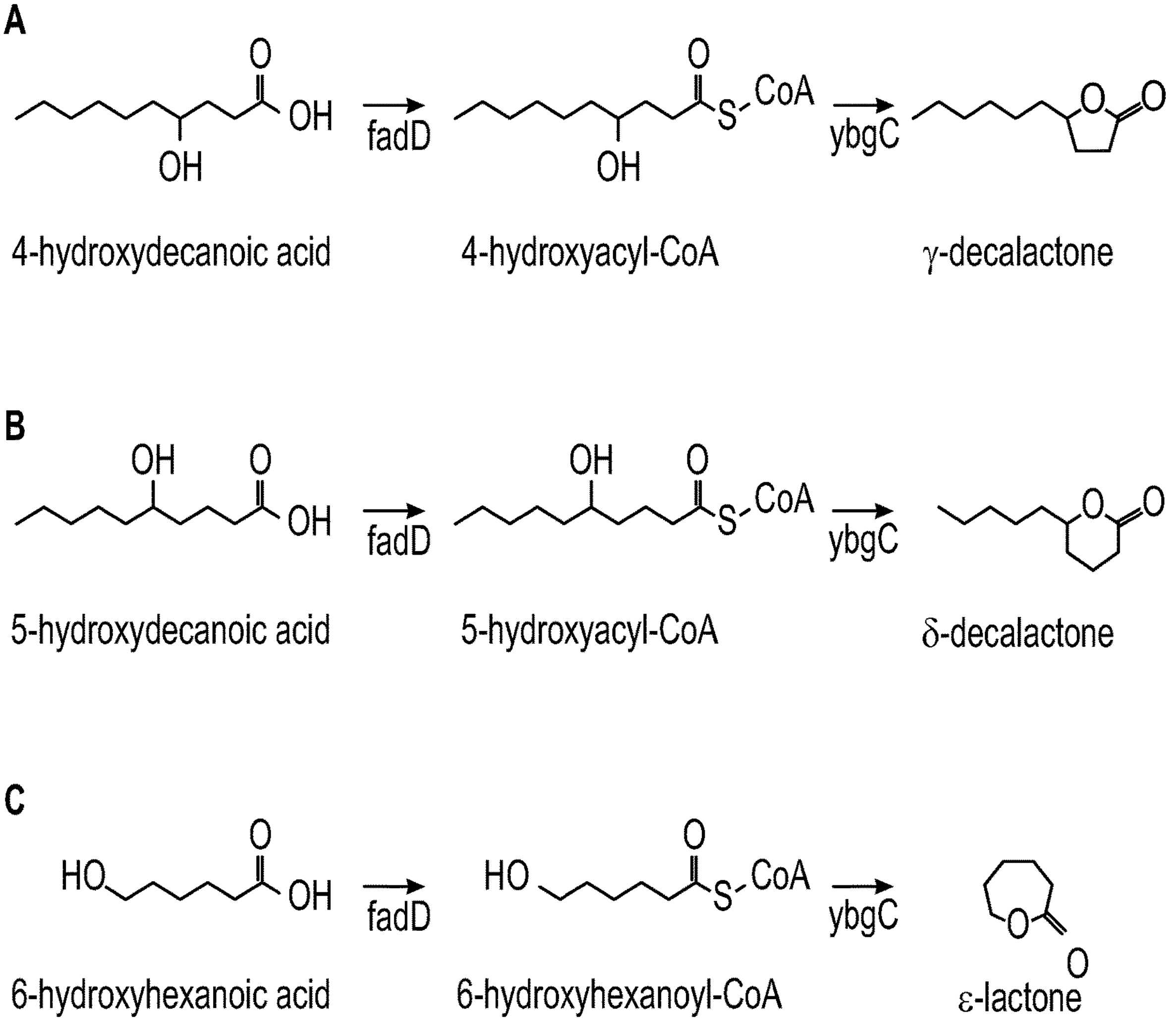
FIG. 2 Illustrates a a biochemical pathway converting 4-hydroxydecanoic acid to natural γ-decalactone (A) or 5-hydroxydecanoic acid to natural δ-decalactone (B), or 6-hydroxyhexanoic acid to natural ε-lactone.

As used herein and in the appended claims, singular articles such as "a" and "an" and "the" and similar referents in the context of describing the elements are to be construed to cover both the singular and the plural, unless otherwise indicated herein or clearly contradicted by context.

As used herein, "about" is understood by persons of ordinary skill in the art and may vary to some extent depending upon the context in which it is used. If there are uses of the term which are not clear to persons of ordinary skill in the art given the context in which the term "about" is used, "about" will mean up to plus or minus 10% of the particular term.

As will be understood by one skilled in the art, for any and all purposes, all ranges disclosed herein also encompass any and all possible subranges and combinations of subranges thereof. Furthermore, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Unless defined otherwise, technical and scientific terms used herein have the same meaning as commonly understood by a person of ordinary skill in the art. In particular, this disclosure utilizes routine techniques in the field of recombinant genetics, organic chemistry, fermentation and biochemistry. Basic texts disclosing the general terms in molecular biology and genetics include e.g., Lackie, *Dictionary of Cell and Molecular Biology*, Elsevier ($5^{th}$ ed. 2013). Basic texts disclosing methods in recombinant genetics and molecular biology include e.g., Sambrook et al., Molecular Cloning—A Laboratory Manual, Cold Spring Harbor Press $4^{th}$ Edition (Cold Spring Harbor, N.Y. 2012) and Current Protocols in Molecular Biology Volumes 1-3, John Wiley & Sons, Inc. (1994-1998) and Supplements 1-115 (1987-2016). Basic texts disclosing the general methods and terms in biochemistry include e.g., *Lehninger Principles of Biochemistry* sixth edition, David L. Nelson and Michael M. Cox eds. W.H. Freeman (2012). Basic texts disclosing the general methods and terminology of fermentation include e.g., *Principles of Fermentation Technology*, 3rd Edition by Peter F Stanbury, Allan Whitaker and Stephen J Hall. Butterworth-Heinemann (2016). Basic texts disclosing the general methods and terms organic chemistry include e.g., Favre, Henri A. and Powell, Warren H. *Nomenclature of Organic Chemistry. IUPAC Recommendations and Preferred Name* 2013. Cambridge, UK: The Royal Society of Chemistry, 2013; *Practical Synthetic Organic Chemistry: Reactions, Principles, and Techniques*, Stephane Caron ed., John Wiley and Sons Inc. (2011); *Organic Chemistry*, 9th Edition—Francis Carey and Robert Giuliano, McGraw Hill (2013).

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as a mixture of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

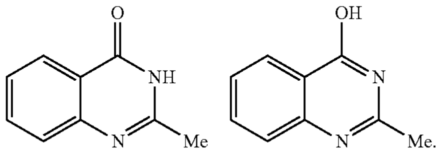

As another example, guanidines may exhibit the following isomeric forms in protic organic solution, also referred to as tautomers of each other:

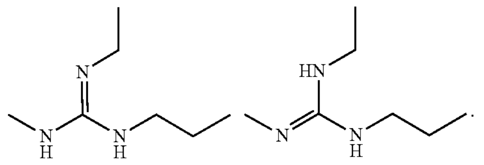

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

Geometric isomers can be represented by the symbol which denotes a bond that can be a single, double or triple bond as described herein. Provided herein are various geometric isomers and mixtures thereof resulting from the arrangement of substituents around a carbon-carbon double bond. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The term "cis" represents substituents on the same side of the plane of the ring, and the term "trans" represents substituents on opposite sides of the plane of the ring. Mixtures of compounds wherein the substituents are disposed on both the same and opposite sides of plane of the ring are designated "cis/trans."

In certain embodiments, the pharmaceutically acceptable form thereof is an isomer. "Isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include cis- and trans-isomers, E- and Z-isomers, R- and S-enantiomers, diastereomers, (d)-isomers, (l)-isomers, racemic mixtures thereof, and other mixtures thereof, as falling within the scope of this disclosure.

"Enantiomers" are a pair of stereoisomers that are non-superimposable mirror images of each other. A mixture of a pair of enantiomers in any proportion can be known as a "racemic" mixture. The term "(+−)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms and intermediate mixtures. Optically active (R)- and (S)-isomers can be prepared, for example, using chiral synthons or chiral reagents, or resolved using conventional techniques. The optical activity of a compound can be analyzed via any suitable method, including but not limited to chiral chromatography and polarimetry, and the degree of predominance of one stereoisomer over the other isomer can be determined.

The term "fatty acid" as used herein, refers to an aliphatic carboxylic acid having the formula RCOOH wherein R is an aliphatic group having at least 4 carbons, typically between about 4 and about 28 carbon atoms. The aliphatic R group can be saturated or unsaturated, branched or unbranched. Unsaturated "fatty acids" may be monounsaturated or polyunsaturated.

A "fatty acid" or "fatty acids", as used herein, can be produced within a cell through the process of fatty acid biosynthesis, through the reverse of fatty acid degradation or beta-oxidation, or they can be fed to a cell. As is well known in the art, fatty acid biosynthesis is generally a malonyl-CoA dependent synthesis of acyl-ACPs or acyl CoAs, while the reverse of beta-oxidation results is acetyl-CoA dependent and results in the synthesis of acyl-CoAs. Fatty acids fed to cell are converted to acyl-CoAs and can be converted to acyl-ACPs. Fatty acids can be synthesized in a cell by natural fatty acid biosynthetic pathways or can be synthesized from heterologous fatty acid biosynthetic pathways that comprise a combination of fatty acid biosynthetic and/or degradation enzymes that result in the synthesis of acyl-CoAs and/or Acyl-ACPs.

Fatty acid biosynthesis and degradation occur in all life forms, including prokaryotes, single cell eukaryotes, higher eukaryotes, and Archaea. The tools and methods disclosed herein are useful in the production of fatty acid derivatives that are derived through any one or more of fatty acid synthesis, degradation, or feeding in any organism that naturally produces alkyl thioesters.

The term "fatty acid derivative" as used herein, refers to a product derived from a fatty acid. Thus, a "fatty acid derivative" includes "fatty acids" as defined above. In general, "fatty acid derivatives" include malonyl-CoA derived compounds including acyl-ACP or acyl-ACP derivatives. "Fatty acid derivatives" also include malonyl-CoA derived compounds such as acyl-CoA or acyl-CoA derivatives. "Fatty acid derivatives" also include acetyl-CoA derived compounds such as acyl-CoA or acyl-CoA derivatives. Thus, a "fatty acid derivatives" include alkyl-thioesters and acyl-thioesters. Further, a "fatty acid derivative" includes a molecule/compound that is derived from a metabolic pathway that includes a fatty acid derivative enzyme. Exemplary fatty acid derivatives include e.g., natural lactones such as e.g., γ-, δ-, and/or ε-lactones as disclosed herein, fatty acids, fatty acid esters (e.g., waxes, fatty acid esters, fatty acid methyl esters (FAME), fatty acid ethyl esters (FAEE)), fatty alcohol acetate esters (FACE), fatty amines, fatty aldehydes, fatty alcohols, hydrocarbons e.g., alkanes, alkenes, etc, ketones, terminal olefins, internal olefins, 3-hydroxy fatty acid derivatives, bifunctional fatty acid derivatives (e.g., ω-hydroxy fatty acids, (ω-1)-hydroxy fatty acids, (ω-2)-hydroxy fatty acids, (ω-3)-hydroxy fatty acids, 10-hydroxy fatty acids, 1,3 fatty-diols, α,ω-diols, α,ω-3-hydroxy triols, ω-hydroxy FAME, ω-OH FAEE, etc.), unsaturated fatty acid derivatives, including unsaturated compounds of each of the above mentioned fatty acid derivatives, etc.

The expression "natural lactone" as used herein, refers to a lactone produced in its entirety by an organism under physiological conditions. A natural lactone is produced in its final form by an organism, without any need for chemical processing (such as e.g, acidic conditions and/or increased temperatures) to produce the lactone. Thus, in embodiments, "natural lactones" are lactones produced by recombinant bacteria that heterologously express a ybgC protein. Such "natural lactones" are isolated from the recombinant bacteria in their final form and require no chemical processing to make. Thus, "natural lactones" are "enzymatically produced lactones" since such "natural lactones" are produced enzymatically by an organism without any need for chemical processing.

The expression "fatty acid derivative composition" as used herein, refers to a composition of fatty acid derivatives, as disclosed herein. A "fatty acid derivative composition" may comprise a single fatty acid derivative species or may comprise a mixture of fatty acid derivative species. In some embodiments, the mixture of fatty acid derivatives includes more than one type of fatty acid derivative product (e.g., natural lactones, fatty acids, fatty acid esters, fatty alcohols, fatty alcohol acetates, fatty aldehydes, fatty amine, bifunctional fatty acid derivatives, and non-native monounsaturated fatty acid derivatives, etc.). In other exemplary embodiments, the mixture of fatty acid derivatives includes fatty acid derivatives with different chain lengths, saturation and/or branching characteristics. In other exemplary embodiments, the mixture of fatty acid derivatives comprises predominantly one type of fatty acid derivative e.g., a composition of natural lactones e.g., γ-lactones, δ-lactones and/or ε-lactones. In still other exemplary embodiments, a "fatty acid derivative composition" comprises a mixture of more than one type of fatty acid derivative product e.g., fatty acid derivatives with different chain lengths, saturation and/or branching characteristics. In still other exemplary embodiments, a "fatty acid derivative composition" comprises a mixture of fatty esters and 3-hydroxy esters. In still other exemplary embodiments, a fatty acid derivative composition comprises a mixture of fatty alcohols and fatty aldehydes. In still other exemplary embodiments, a fatty acid derivative composition comprises a mixture of FAME and/or FAEE. In still other exemplary embodiments, a fatty acid derivative composition comprises a mixture of fatty alcohol acetate esters (FACE), for example a mixture of non-native monounsaturated fatty alcohol acetate esters (FACE).

The term "malonyl-CoA derived compound" as used herein refers to any compound or chemical entity (i.e., intermediate or end product) that is made via a biochemical pathway wherein malonyl-CoA functions as intermediate and/or is made upstream of the compound or chemical entity. For example, a malonyl-CoA derived compound may include, but is not limited to, a fatty acid derivative such as, for example, natural lactone e.g., a natural γ-, δ-, and/or ε-lactone, a fatty acid; a fatty ester including, but not limited to a fatty acid methyl ester (FAME) and/or a fatty acid ethyl ester (FAEE); a fatty alcohol; a fatty aldehyde; a fatty amine; an alkane; an olefin or alkene; a hydrocarbon; a beta hydroxy fatty acid derivative, a bifunctional fatty acid derivative, a multifunctional fatty acid derivative, a native or non-native unsaturated fatty acid derivative, etc.

As used herein "alkyl-thioester" or equivalently an "acyl thioester" is a compound in which the carbonyl carbon of an acyl chain and the sulfydryl group of an organic thiol are joined through a thioester bond. Representative organic thiols include e.g., Cystein, beta-cysteine, glutathione, mycothiol, pantetheine, Coenzyme A (CoA) and the acyl carrier protein (ACP). An "acyl-ACP" refers to an "alkyl-thioester" formed between the carbonyl carbon of an acyl chain and the sulfhydryl group of the phosphopantetheinyl moiety of an ACP. An "Acyl-CoA" refers to an "alkyl-thioester" formed between the carbonyl carbon of an acyl chain and the sulfhydryl group of the phosphopantetheinyl moiety of CoA. In some embodiments an "alkyl-thioester", such as acyl-ACP or acyl CoA, is an intermediate in the synthesis of fully saturated acyl-thioesters. In other embodiments an "alkyl-thioester", such as acyl-ACP or acyl-CoA, is an intermediate in the synthesis of unsaturated acyl thioesters. In some embodiments, the carbon chain of the acyl group of an acyl thioester has 5, 6, 7, 8, 9, 10, 11, 12, 13, 14, 15, 16, 17, 18, 19, 20, 21, 22, 23, 24, 25, 26, 27 or 28 carbons. In other embodiments, the carbon chain of the acyl group of acyl-thioester is a medium-chain and has 6, 7, 8, 9, 10, 11, 12, 13, 14, 15, 16 or 18 carbons. In other exemplary embodiments the carbon chain of the acyl group of acyl-thioester is 8 carbons in length. In other exemplary embodiments the carbon chain of the acyl group of acyl-thioester is 10 carbons in length. In still other exemplary embodiments, the carbon chain of the acyl group of acyl-thioester is 12 carbons in length. In still other exemplary embodiments, the carbon chain of the acyl group of acyl-thioester is 14 carbons in length. In still other exemplary embodiments, the carbon chain of the acyl group of acyl-thioester is 16 carbons in length. "alkyl-thioesters" are substrates for fatty acid derivative enzymes such as e.g., lactonizing enzymes e.g., YbgC, thioesterases, acyl ACP reductases, ester synthases and their engineered variants that convert the acyl-thioester to fatty acid derivatives such as e.g., natural lactones.

As used herein, the expression "fatty acid derivative biosynthetic pathway" refers to a biochemical pathway that produces fatty acid derivatives. The enzymes that comprise a "fatty acid derivative biosynthetic pathway" are thus referred to herein as "fatty acid derivative biosynthetic polypeptides" or equivalently "fatty acid derivative enzymes". As discussed supra, the term "fatty acid derivative," includes a molecule/compound derived from a biochemical pathway that includes a fatty acid derivative enzyme. Thus, a lactonizing enzyme such as e.g., *E. coli* ybgC, is a "fatty acid derivative biosynthetic peptide" or equivalently a "fatty acid derivative enzyme". Similarly, a thioesterase enzyme (e.g., an enzyme having thioesterase activity EC 3.2.1.14) is a "fatty acid derivative biosynthetic peptide" or equivalently a "fatty acid derivative enzyme." Thus the term "fatty acid derivative enzymes" or equivalently "fatty acid derivative biosynthetic polypeptides" refers to, collectively and individually, enzymes that may be expressed or overexpressed to produce fatty acid derivatives such as e.g., natural lactones. Non-limiting examples of "fatty acid derivative enzymes" or equivalently "fatty acid derivative biosynthetic polypeptides" include e.g., fatty acid synthases, lactonizing enzymes, thioesterases, acyl-CoA synthetases, acyl-CoA reductases, acyl ACP reductases, alcohol dehydrogenases, alcohol oxidases, aldehyde dehydrogenases, alcohol O-acyltransferases, fatty alcohol-forming acyl-CoA reductases, fatty acid decarboxylases, fatty aldehyde decarbonylases and/or oxidative deformylases, carboxylic acid reductases, fatty alcohol O-acetyl transferases, hydroxylating enzymes, ester synthases, etc. "Fatty acid derivative enzymes" or equivalently "fatty acid derivative biosynthetic polypeptides" convert substrates into fatty acid derivatives. In exemplary embodiments, a suitable substrate for a fatty acid derivative enzyme is a first fatty acid derivative, e.g. a 5-hydroxy fatty acid, which is converted by the fatty acid derivative enzyme into a different, second fatty acid derivative e.g., a natural δ-lactone.

The term "YbgC protein" or YbgC enzyme" as used herein, refers to a protein/enzyme having lactonizing activity and having at least about 60% sequence identity to SEQ ID NO:1 over the full length of the protein The expression "lactonizing activity" as used herein, refers to the ability of an enzyme/protein to convert a hydroxy-fatty acid substrate to a lactone under physiological conditions. Thus, "lactonizing enzymes" have "lactonizing activity". In an embodiment, a lactonizing enzyme converts a 4-hydroxy fatty acid to a γ-lactone. In an embodiment, a lactonizing enzyme converts a 5-hydroxy fatty acid to a δ-lactone. In an embodiment, a lactonizing enzyme converts a 6-hydroxy fatty acid to an ε-lactone.

In embodiments, "lactonizing activity" is measured by measuring the amount e.g., volume, weight, titer, etc of a substrate e.g., a hydroxyl fatty acid substrate, that is converted to a particular lactone or lactones by a recombinant bacterium that expresses a putative "lactonizing enzyme" and comparing the measured amount to the amount of the same lactone produced by an isogenic bacterial strain that does not express the putative "lactonizing enzyme".

For example, the amount of hydroxyl fatty acid substrate that is converted to a particular lactone or lactones by a wild type *E. coli* strain is measured and compared to the amount hydroxyl fatty acid substrate that is converted to a particular lactone or lactones by an isogenic *E. coli* strain that heterologously expresses an enzyme with potential lactonizing activity. Typically, enzyme with potential lactonizing activity is said to have "lactonizing activity" when the strain that expresses an enzyme with potential lactonizing activity produces an amount of lactone that is at least 3% more than that of the control strain. In some embodiments, a strain expressing an enzyme having "lactonizing activity" produces an amount of lactone that is 5% more, 6% more, 7% more, 8% more, 9% more, 10% more, 20% more, 30% more, 40% more, 50% more, 60% more, 70% more, 75% more, 80% more, 90% more, 95% more, 100% more or more than 100% more than that of the control strain.

Alternatively, if a bacterium expresses an enzyme suspected of having lactonizing activity, then the gene encoding the enzyme with suspected of having lactonizing activity can be deleted and the amount of hydroxyl fatty acid substrate that is converted to a particular lactone or lactones by the strain carrying the deletion is measured and compared to the amount hydroxyl fatty acid substrate that is converted to the particular lactone or lactones by an isogenic strain that does not carry deletion of the enzyme suspected of having lactonizing activity. As above, the deleted enzyme would be said to have "lactonizing activity" when the strain that expresses an enzyme with potential lactonizing activity produces an amount of lactone that is at least 3% more than that of the control strain. In some embodiments, a strain expressing an enzyme having "lactonizing activity" produces an amount of lactone that is 5% more, 6% more, 7% more, 8% more, 9% more, 10% more, 20% more, 30% more, 40% more, 50% more, 60% more, 70% more, 75% more, 80% more, 90% more, 95% more, 100% more or more than 100% more than that of the strain from which the enzyme is deleted.

In some embodiments, "lactonizing activity" is measured by measuring the amount e.g., volume, weight, titer, etc of a substrate e.g., a hydroxyl fatty acid substrate, that is converted to a particular lactone or lactones by a recombinant bacterium that expresses a putative "lactonizing enzyme" and an acyl-CoA synthetase. Laconizing activity is determined as discussed above. The production of the lactone is measured using any convenient method known in the art e.g., using GC-MS. The lactone can be made either in vivo or using an in vitro system.

The expression "physiological conditions" as used herein, refers to typical culture conditions for growing bacteria, e.g., *E. coli*. Such conditions are well known in the art see e.g., Sambrook et al., and Current Protocols in Molecular Biology Volumes 1-3, John Wiley & Sons, Inc. (1994-1998) and Supplements 1-115 (1987-2016) supra. For example, typically bacterial cultures are grown at neutral pH and at a temperature of between about 25° C. to 42° C., typically at about 37° C. Although bacteria exist which are able to grow under acidic conditions i.e. acidophiles, as used herein, the expression "physiological conditions" specifically excludes acidic conditions and refers particularly to conditions of neutral pH.

The expression "hydroxy acyl-CoA substrate" as used herein refers to a natural lactone precursor which comprises hydroxy fatty acid and coenzyme A linked together through an hydroxy acyl-CoA thioester bond. Typically, a "hydroxy acyl-CoA substrate" is formed by the activity of an acyl-CoA synthetase acting on a hydroxy fatty acid and coenzyme A to form the hydroxy acyl-CoA thioester bond and thereby to produce an hydroxy acyl-CoA molecule.

Sequence Accession numbers throughout this description were obtained from databases provided by the NCBI (National Center for Biotechnology Information) maintained by the National Institutes of Health, U.S.A. (which are identified herein as "NCBI Accession Numbers" or alternatively as "GenBank Accession Numbers" or alternatively a simply "Accession Numbers"), and from the UniProt Knowledgebase (UniProtKB) and Swiss-Prot databases provided by the Swiss Institute of Bioinformatics (which are identified herein as "UniProtKB Accession Numbers").

The term "enzyme classification (EC) number" refers to a number that denotes a specific polypeptide sequence or enzyme. EC numbers classify enzymes according to the reaction they catalyze. EC numbers are established by the nomenclature committee of the international union of biochemistry and molecular biology (IUBMB), a description of which is available on the IUBMB enzyme nomenclature website on the world wide web.

As used herein, the term "isolated," with respect to products (such as enzymatically produced lactones as disclosed herein) refers to products that are separated from cellular components, cell culture media, or chemical or synthetic precursors. The enzymatically produced lactones disclosed herein produced by the methods disclosed herein can be relatively immiscible in the fermentation broth, as well as in the cytoplasm. Therefore, in exemplary embodiments, the enzymatically produced lactones disclosed herein collect in an organic phase extracellularly and are thereby "isolated".

As used herein, the terms "polypeptide" and "protein" are used interchangeably to refer to a polymer of amino acid residues that is typically 12 or more amino acids in length. Polypeptides less than 12 amino acids in length are referred to herein as "peptides". The terms apply to amino acid polymers in which one or more amino acid residue is an artificial chemical mimetic of a corresponding naturally occurring amino acid, as well as to naturally occurring amino acid polymers and non-naturally occurring amino acid polymers. The term "recombinant polypeptide" refers to a polypeptide that is produced by recombinant techniques, wherein generally DNA or RNA encoding the expressed protein is inserted into a suitable expression vector that is in turn used to transform a host cell to produce the polypeptide. In some exemplary embodiments, DNA or RNA encoding an expressed peptide, polypeptide or protein is inserted into the host chromosome via homologous recombination or other means well known in the art, and is so used to transform a host cell to produce the peptide or polypeptide. Similarly, the terms "recombinant polynucleotide" or "recombinant nucleic acid" or "recombinant DNA" are produced by recombinant techniques that are known to those of skill in the art (see e.g., methods described in Sambrook et al. (supra) and/or Current Protocols in Molecular Biology (supra).

When referring to two nucleotide or polypeptide sequences, the "percentage of sequence identity" between the two sequences is determined by comparing the two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The "percentage of sequence identity" is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Thus, the expression "percent identity," or equivalently "percent sequence identity" in the context of two or more nucleic acid sequences or peptides or polypeptides, refers to two or more sequences or subsequences that are the same or have a specified percentage of nucleotides or amino acids that are the same (e.g., about 50% identity, preferably 55%, 60%, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured e.g., using a BLAST or BLAST 2.0 sequence comparison algorithm with default parameters (see e.g., Altschul et al. (1990) *J. Mol. Biol.* 215 (3): 403-410) and/or the NCBI web site at ncbi.nlm.nih.gov/BLAST/) or by manual alignment and visual inspection. Percent sequence identity between two nucleic acid or amino acid sequences also can be determined using e.g., the Needleman and Wunsch algorithm that has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6 (Needleman and Wunsch (1970) *J. Mol. Biol.* 48:444-453). The percent sequence identity between two nucleotide sequences also can be determined using the GAP program in the GCG software package, using a NWSgapdna.CMP matrix and a gap weight of 40, 50, 60, 70, or 80 and a length weight of 1, 2, 3, 4, 5, or 6. One of ordinary skill in the art can perform initial sequence identity calculations and adjust the algorithm parameters accordingly. A set of parameters that may be used if a practitioner is uncertain about which parameters should be applied to determine if a molecule is within a sequence identity limitation of the claims, are a Blossum 62 scoring matrix with a gap penalty of 12, a gap extend penalty of 4, and a frameshift gap penalty of 5. Additional methods of sequence alignment are known in the biotechnology arts (see, e.g., Rosenberg (2005) *BMC Bioinformatics* 6:278; Altschul et al. (2005) *FEBS J.* 272 (20): 5101-5109).

Two or more nucleic acid or amino acid sequences are said to be "substantially identical," when they are aligned and analyzed as discussed above and are found to share about 50% identity, preferably 55%, 60%, 65%, 70%, 75%, 80%, 85%, 90%, 91%, 92%, 93%, 94%, 95%, 96%, 97%, 98%, 99%, or higher identity over a specified region. Two nucleic acid sequences or polypeptide sequences are said to be "identical" if the sequence of nucleotides or amino acid residues, respectively, in the two sequences are the same when aligned for maximum correspondence as described above. This definition also refers to, or may be applied to, the compliment of a test sequence. Identity is typically calculated over a region that is at least about 25 amino acids or nucleotides in length, or more preferably over a region that is 50-100 amino acids or nucleotides in length, or over the entire length of a given sequence.

The expressions "hybridizes under low stringency, medium stringency, high stringency, or very high stringency conditions" describe conditions for hybridization and washing. Guidance for performing hybridization reactions can be found e.g., in Current Protocols in Molecular Biology, John Wiley & Sons, N.Y. (1989), 6.3.1-6.3.6. Aqueous and non-aqueous methods are described in the cited reference and either method can be used. Specific hybridization conditions referred to herein are as follows: (1) low stringency hybridization conditions—6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions—6×SSC at about 45° C., followed by one or more washes in 0.2×SSC, 0.1% SDS at 60° C.; (3) high stringency hybridization conditions—6×SSC at about 45° C., followed by one or more washes in 0.2.×SSC, 0.1% SDS at 65° C.; and (4) very high stringency hybridization conditions—0.5M sodium phosphate, 7% SDS at 65° C., followed by one or more washes at 0.2×SSC, 1% SDS at 65° C. Very high stringency conditions (4) are the preferred conditions unless otherwise specified.

The term "endogenous" as used herein refers to a substance e.g., a nucleic acid, protein, etc. that is produced from within a cell. Thus, an "endogenous" polynucleotide or polypeptide refers to a polynucleotide or polypeptide produced by the cell. In some exemplary embodiments an "endogenous" polypeptide or polynucleotide is encoded by the genome of the parental cell (or host cell). In other exemplary embodiments, an "endogenous" polypeptide or polynucleotide is encoded by an autonomously replicating plasmid carried by the parental cell (or host cell). In some exemplary embodiments, an "endogenous" gene is a gene that was present in the cell when the cell was originally isolated from nature i.e., the gene is "native to the cell". In other exemplary embodiments, an "endogenous" gene has been altered through recombinant techniques e.g., by altering the relationship of control and coding sequences. Thus, a "heterologous" gene may, in some exemplary embodiments, be "endogenous" to a host cell.

In contrast, an "exogenous" polynucleotide or polypeptide, or other substance (e.g., fatty acid derivative or oleochemical, small molecule compound, etc.) refers to a polynucleotide or polypeptide or other substance that is not produced by the parental cell and which is therefore added to a cell, a cell culture or assay from outside of the cell. Thus, a molecule or compound As used herein the term "native" refers to the form of a nucleic acid, protein, polypeptide or a fragment thereof that is isolated from nature or a nucleic acid, protein, polypeptide or a fragment thereof that is in its natural state without intentionally introduced mutations in the structural sequence and/or without any engineered changes in expression such as e.g., changing adevelopmentally regulated gene to aconstitutively expressed gene.

As used herein, the term "fragment" of a polypeptide refers to a shorter portion of a full-length polypeptide or protein ranging in size from two amino acid residues to the entire amino acid sequence minus one amino acid residue. In certain embodiments of the disclosure, a fragment refers to the entire amino acid sequence of a domain of a polypeptide or protein (e.g., a substrate binding domain or a catalytic domain).

The term "gene" as used herein, refers to nucleic acid sequences e.g., DNA sequences, which encode either an RNA product or a protein product, as well as operably-linked nucleic acid sequences that affect expression of the RNA or protein product (e.g., expression control sequences such as e.g., promoters, enhancers, ribosome binding sites, translational control sequences, etc). The term "gene product" refers to either the RNA e.g., tRNA, mRNA and/or protein expressed from a particular gene.

The term "expression" or "expressed" as used herein in reference to a gene, refers to the production of one or more transcriptional and/or translational product(s) of a gene. In exemplary embodiments, the level of expression of a DNA molecule in a cell is determined on the basis of either the amount of corresponding mRNA that is present within the cell or the amount of protein encoded by that DNA produced by the cell. The term "expressed genes" refers to genes that are transcribed into messenger RNA (mRNA) and then translated into protein, as well as genes that are transcribed into other types of RNA, such as e.g., transfer RNA (tRNA), ribosomal RNA (rRNA), and regulatory RNA, which are not translated into protein.

The level of expression of a nucleic acid molecule in a cell or cell free system is influenced by "expression control sequences" or equivalently "regulatory sequences". "Expression control sequences" or "regulatory sequences" are known in the art and include, for example, promoters, enhancers, polyadenylation signals, transcription terminators, nucleotide sequences that affect RNA stability, internal ribosome entry sites (IRES), and the like, that provide for the expression of the polynucleotide sequence in a host cell. In exemplary embodiments, "expression control sequences" interact specifically with cellular proteins involved in transcription (see e.g., Maniatis et al., *Science,* 236:1237-1245 (1987); Goeddel, Gene Expression Technology: Methods in Enzymology, Vol. 185, Academic Press, San Diego, Calif. (1990)). In exemplary methods, an expression control sequence is operably linked to a polynucleotide sequence. By "operably linked" is meant that a polynucleotide sequence and an expression control sequence(s) are functionally connected so as to permit expression of the polynucleotide sequence when the appropriate molecules (e.g., transcriptional activator proteins) contact the expression control sequence(s). In exemplary embodiments, operably linked promoters are located upstream of the selected polynucleotide sequence in terms of the direction of transcription and translation. In some exemplary embodiments, operably linked enhancers can be located upstream, within, or downstream of the selected polynucleotide.

As used herein, the phrase "the expression of said nucleotide sequence is modified relative to the wild type nucleotide sequence", refers to a change e.g., an increase or decrease in the level of expression of an native nucleotide sequence or a change e.g., an increase or decrease in the level of the expression of a heterologous or non-native polypeptide-encoding nucleotide sequence as compared to a control nucleotide sequence e.g., wild-type control. In some exemplary embodiments, the phrase "the expression of said nucleotide sequence is modified relative to the wild type nucleotide sequence," refers to a change in the pattern of expression of a nucleotide sequence as compared to a control pattern of expression e.g., constitutive expression as compared to developmentally timed expression.

In other embodiments, the polypeptide, polynucleotide, or hydrocarbon having an altered level of expression is "attenuated" or has a "decreased level of expression." As used herein, "attenuate" and "decreasing the level of expression" mean to express or cause to be expressed a polynucleotide, polypeptide, or hydrocarbon in a cell at a lesser concentration than is normally expressed in a corresponding control cell (e.g., wild type cell) under the same conditions.

A polynucleotide or polypeptide can be attenuated using any method known in the art. For example, in some exemplary embodiments, the expression of a gene or polypeptide encoded by the gene is attenuated by mutating the regulatory polynucleotide sequences which control expression of the gene. In other exemplary embodiments, the expression of a gene or polypeptide encoded by the gene is attenuated by overexpressing a repressor protein, or by providing an exogenous regulatory element that activates a repressor protein. In still other exemplary embodiments, DNA- or RNA-based gene silencing methods are used to attenuate the expression of a gene or polynucleotide. In some embodiments, the expression of a gene or polypeptide is completely attenuated, e.g., by deleting all or a portion of the polynucleotide sequence of a gene.

The degree of overexpression or attenuation can be 1.5-fold or more, e.g., 2-fold or more, 3-fold or more, 5-fold or more, 10-fold or more, or 15-fold or more. Alternatively, or in addition, the degree of overexpression or attenuation can be 500-fold or less, e.g., 100-fold or less, 50-fold or less, 25-fold or less, or 20-fold or less. Thus, the degree of overexpression or attenuation can be bounded by any two of the above endpoints. For example, the degree of overexpression or attenuation can be 1.5-500-fold, 2-50-fold, 10-25-fold, or 15-20-fold.

As used herein, "modified activity" or an "altered level of activity" of a protein/polypeptide in a recombinant host cell refers to a difference in one or more characteristics in the activity the protein/polypeptide as compared to the characteristics of an appropriate control protein e.g., the corresponding parent protein or corresponding wild type protein. Thus, in exemplary embodiments, a difference in activity of a protein having "modified activity" as compared to a corresponding control protein is determined by measuring the activity of the modified protein in a recombinant host cell and comparing that to a measure of the same activity of a corresponding control protein in an otherwise isogenic host cell. Modified activities can be the result of, for example, changes in the structure of the protein (e.g., changes to the primary structure, such as e.g., changes to the protein's nucleotide coding sequence that result in changes in substrate specificity, changes in observed kinetic parameters, changes in solubility, etc.); changes in protein stability (e.g., increased or decreased degradation of the protein) etc.

A "control" sample e.g., a "control" nucleotide sequence, a "control" polypeptide sequence, a "control" cell, etc., or value refers to a sample that serves as a reference, usually a known reference, for comparison to a test sample. For example, in an exemplary embodiment, a test sample comprises an enzymatically produced lactone composition produced by a recombinant bacterium that heterologously expresses a YbgC protein as disclosed herein, while the control sample comprises an enzymatically produced lactone composition made by the corresponding or designated bacterium that does not heterologously express a YbgC protein. One of skill will recognize that controls can be designed for assessment of any number of parameters. Furthermore, one of skill in the art will understand which controls are valuable in a given situation and will be able to analyze data based on comparisons to control values.

The term "overexpressed" as used herein, refers to a gene whose expression is elevated in comparison to a "control" level of expression. In exemplary embodiments, "overexpression" of a gene is caused by an elevated rate of transcription as compared to the native transcription rate for that gene. Since "overexpression" is by definition a non-native form of expression of a gene, "a gene that is "overexpressed" is a gene that is "heterologously expressed" (see below). In other exemplary embodiments, overexpression is caused by an elevated rate of translation of the gene compared to the native translation rate for that gene. Methods of testing for overexpression are well known in the art, for example transcribed RNA levels can be assessed using rtPCR and protein levels can be assessed using SDS page gel analysis.

The term "heterologous" as used herein refers to a polypeptide or polynucleotide which is in a non-native state. In the context of a cell and a protein or cell and a polynucleotide the term "heterologous" refers to a polypeptide or a polynucleotide that is not native to the cell in which it is expressed/produced. Thus, a polynucleotide or a polypeptide is "heterologous" to a cell when the polynucleotide and/or the polypeptide and the cell are not found in the same relationship to each other in nature. Therefore, a polynucleotide or polypeptide sequence is "heterologous" to an organism or a second sequence if it originates from a different organism, different cell type, or different species, or, if from the same species, it is modified from its original form. Thus, in an exemplary embodiment, a polynucleotide or polypeptide is "heterologous" when it is not naturally present in a given organism. For example, a polynucleotide sequence that is native to cyanobacteria can be introduced into a host cell of *E. coli* by recombinant methods, and the polynucleotide from cyanobacteria is then heterologous to the *E. coli* cell (i.e., the now recombinant *E. coli* cell).

Similarly, a polynucleotide or polypeptide is "heterologous" when it is modified from its native form or from its relationship with other polynucleotide sequences or is present in a recombinant host cell in a non-native state. Thus, in an exemplary embodiment, a 'heterologous" polynucleotide or polypeptide comprises two or more subsequences that are not found in the same relationship to each other in nature. For example, a promoter operably linked to a nucleotide coding sequence derived from a species different from that from which the promoter was derived. Alternatively, in another example, if a promoter is operably linked to a nucleotide coding sequence derived from a species that is the same as that from which the promoter was derived, then the operably-linked promoter and coding sequence are "heterologous" if the coding sequence is not naturally associated with the promoter (e.g. a constitutive promoter operably linked to a developmentally regulated coding sequence that is derived from the same species as the promoter). In other exemplary embodiments, a "heterologous" polynucleotide or polypeptide is modified relative to the wild type sequence naturally present in the corresponding wild type host cell, e.g., an intentional modification e.g., an intentional mutation in the sequence of a polynucleotide or polypeptide or a modification in the level of expression of the polynucleotide or polypeptide. Typically, a heterologous nucleic acid or polynucleotide is recombinantly produced.

The term "recombinant" as used herein, refers to a genetically modified polynucleotide, polypeptide, cell, tissue, or organism. When used with reference to a cell, the term "recombinant" indicates that the cell has been modified by the introduction of a heterologous nucleic acid or protein or has been modified by alteration of a native nucleic acid or protein, or that the cell is derived from a cell so modified and that the derived cell comprises the modification. Thus, for example, "recombinant cells" or equivalently "recombinant host cells" may be modified to express genes that are not found within the native (non-recombinant) form of the cell or may be modified to abnormally express native genes e.g., heterologously expressed native genes may be overexpressed, underexpressed or not expressed at all. In exemplary embodiments, a "recombinant cell" or "recombinant host cell" is engineered to heterologously express a heterologous enzyme pathway capable of enzymatically producing a lactone under physiological conditions e.g., without acidification of the culture medium. A recombinant cell can be derived from a microorganism such as a bacterium, a virus or a fungus. However, typically, as used herein a "recombinant cell" is a "recombinant bacterium".

In exemplary embodiments, a "recombinant host cell" or "recombinant cell" is used to enzymatically producing one or more natural lactones e.g., γ-lactones, δ-lactone and/or ε-lactones under physiological conditions e.g., without acidification of the culture medium including, but not limited to. Therefore, in some exemplary embodiments a "recombinant host cell" is a "production host" or equivalently, a "production host cell". In some embodiments, the recombinant cell includes one or more polynucleotides, wherein the polynucleotides encode a polypeptides having fatty acid biosynthetic enzyme activity e.g., a thioesterase, a fatty acid hydoxylating enzyme, an acyl-CoA synthetase, wherein the recombinant cell produces an hydroxy acyl-CoA substrate that is converted to a lactone by virtue of the activity of a lactonizing enzyme e.g., a ybgC protein, when cultured in the presence of a (simple) carbon source at neutral pH, under conditions effective to express the polynucleotides.

When used with reference to a polynucleotide, the term "recombinant" indicates that the polynucleotide has been modified by comparison to the native or naturally occurring form of the polynucleotide or has been modified by comparison to a naturally occurring variant of the polynucleotide. In an exemplary embodiment, a recombinant polynucleotide (or a copy or complement of a recombinant polynucleotide) is one that has been manipulated by the hand of man to be different from its naturally occurring form. Thus, in an exemplary embodiment, a recombinant polynucleotide is a mutant form of a native gene or a mutant form of a naturally occurring variant of a native gene wherein the mutation is made by intentional human manipulation e.g., made by saturation mutagenesis using mutagenic oligonucleotides, through the use of UV radiation, mutagenic chemicals, chemical synthesis etc. Such a recombinant polynucleotide might comprise one or more point mutations, deletions and/or insertions relative to the native or naturally occurring variant form of the gene. Similarly, a polynucleotide comprising a promoter operably linked to a second polynucleotide (e.g., a coding sequence) is a "recombinant" polynucleotide. Accordingly, in an embodiment, a "recombinant" polynucleotide comprises a native enzyme under the control of a heterologous or synthetic promoter. Thus, a recombinant polynucleotide comprises polynucleotide combinations that are not found in nature. A recombinant protein (discussed supra) is typically one that is expressed from a recombinant polynucleotide, and recombinant cells, tissues, and organisms are those that comprise recombinant sequences (polynucleotide and/or polypeptide).

The expression "heterologously expresses" or "heterologously expressed" as used herein, refers to a recombinant bacterium that expresses a recombinant polynucleotide or recombinant polypeptide/protien.

A "production host" or equivalently a "production host cell" is a cell used to produce products. As disclosed herein, a "production host" is typically modified to express or overexpress selected genes, or to have attenuated expression of selected genes. Thus, a "production host" or a "production host cell" is a "recombinant host" or equivalently a "recombinant host cell". As an example, a "production host" heterologously expresses a ybgC protein. As another example, a "production host" heterologously expresses a ybgC protein and heterologously expresses an acyl CoA synthetase.

The term "acetyl-CoA derived compound" refers to any compound or chemical entity (i.e., intermediate or end product) that is made via a biochemical pathway wherein acetyl-CoA functions as intermediate and/or is made upstream of the compound or chemical entity. For example, a acetyl-CoA derived compound may include, but is not limited to, a fatty acid derivative such as, for example, a fatty acid; a fatty ester including, but not limited to a fatty acid methyl ester (FAME) and/or a fatty acid ethyl ester (FAEE); a fatty alcohol; a fatty aldehyde; a fatty amine; an alkane; an olefin or alkene; a hydrocarbon; a 3-hydroxy fatty acid derivative, a bifunctional fatty acid derivative, a non-native monounsaturated fatty acid derivative, an unsaturated fatty acid derivative, a natural lactone, etc.

As used herein, the terms "purify," "purified," or "purification" mean the removal or isolation of a molecule from its environment by, for example, isolation or separation. "Substantially purified" molecules are at least about 60% free (e.g., at least about 65% free, at least about 70% free, at least about 75% free, at least about 80% free, at least about 85% free, at least about 90% free, at least about 95% free, at least about 96% free, at least about 97% free, at least about 98% free, at least about 99% free) from other components with which they are associated. As used herein, these terms also refer to the removal of contaminants from a sample. For example, the removal of contaminants can result in an increase in the percentage of enzymatically produced lactones or other compounds in a sample. For example, when an enzymatically produced lactones or other compound is produced in a recombinant host cell, the enzymatically produced lactone or other compound can be purified by the removal of host cell proteins. After purification, the percentage of enzymatically produced lactone or other compounds in the sample is increased. The terms "purify," "purified," and "purification" are relative terms which do not require absolute purity. Thus, for example, when an enzymatically produced lactone is produced in recombinant host cells, an enzymatically produced lactones that is substantially separated from other cellular components (e.g., nucleic acids, polypeptides, lipids, carbohydrates, or other hydrocarbons).

As used herein, the term "attenuate" means to weaken, reduce, or diminish. For example, a polypeptide can be attenuated by modifying the polypeptide to reduce its activity (e.g., by modifying a nucleotide sequence that encodes the polypeptide).

As used herein, the term "carbon source" refers to a substrate or compound suitable to be used as a source of carbon for prokaryotic or simple eukaryotic cell growth. Carbon sources can be in various forms, including, but not limited to polymers, carbohydrates, acids, alcohols, aldehydes, ketones, amino acids, peptides, and gases (e.g., CO and $CO_2$). Exemplary carbon sources include, but are not limited to, monosaccharides, such as glucose, fructose, mannose, galactose, xylose, and arabinose; oligosaccharides, such as fructo-oligosaccharide and galacto-oligosaccharide; polysaccharides such as starch, cellulose, pectin, and xylan; disaccharides, such as sucrose, maltose, cellobiose, and turanose; cellulosic material and variants such as hemicelluloses, methyl cellulose and sodium carboxymethyl cellulose; succinate, lactate, and acetate; alcohols, such as ethanol, methanol, and glycerol, or mixtures thereof. The carbon source can also be a product of photosynthesis, such as glucose. In certain embodiments, the carbon source is biomass. In other embodiments, the carbon source is glucose. In other embodiments the carbon source is sucrose. In other embodiments the carbon source is glycerol. In other embodiments, the carbon source is a simple carbon source such as e.g., glucose. In other embodiments, the carbon source is a renewable carbon source. In other embodiment, the carbon source is natural gas. In other embodiments the carbon source comprises one or more components of natural gas, such as methane, ethane, or propane. In other embodiments, the carbon source is flu gas or synthesis gas. In still other embodiments, the carbon source comprises one or more components of flu or synthesis gas such as carbon monoxide, carbon dioxide, hydrogen, etc. As used herein, the term "carbon source" or "simple carbon source" specifically excludes oleochemicals such as e.g., saturated or unsaturated fatty acids.

As used herein, the term "biomass" refers to any biological material from which a carbon source is derived. In some embodiments, a biomass is processed into a carbon source which is suitable for bioconversion. In other embodiments, the biomass does not require further processing into a carbon source. The carbon source can be converted into a composition comprising enzymatically produced lactones.

An exemplary source of biomass is plant matter or vegetation, such as corn, sugar cane, or switchgrass. Another exemplary source of biomass is metabolic waste products, such as animal matter (e.g., cow manure). Further exemplary sources of biomass include algae and other marine plants. Biomass also includes waste products from industry, agriculture, forestry, and households, including, but not limited to, glycerol, fermentation waste, ensilage, straw, lumber, sewage, garbage, cellulosic urban waste, and food leftovers (e.g., soaps, oils and fatty acids). The term "biomass" also can refer to sources of carbon, such as carbohydrates (e.g., monosaccharides, disaccharides, or polysaccharides).

I. Introduction

As discussed above, there is an increasing demand for natural flavor and fragrance ingredients to satisfy the needs of e.g., the food, beverage, fragrance and cosmetics industries.

Typically, flavors and fragrance molecules are extracted from their natural sources, or are prepared using biotechnological processes that involve a chemical conversion step. The extraction of flavors and fragrances from natural sources is laborious process and unfortunately, because many known biotechnological processes require a chemical conversion step, in many countries flavors and fragrances produced by biotechnological processes are disqualified from being marketed and sold as natural flavor (see e.g., EFFA Guidance Document for the Production of Natural Flavouring Substances and (Natural) Flavouring Preparations in the EU).

Therefore, to meet the needs of industry, new methods for the production of natural flavors and fragrances, e.g. lactones, are needed.
Accordingly, the present disclosure provides methods for the biological/enzymatic production of natural lactones without a chemical conversion step. As will be disclosed in detail below, the disclosure provides methods for the enzymatic production of lactones under physiological conditions via a hydroxyacyl-CoA intermediate, in recombinant cells (in vivo) or cell lysates (in vitro).

II. Bacteria that Enzymatically Produce Lactones

A. General Methods

This disclosure utilizes routine techniques in the field of recombinant genetics. Basic texts disclosing the general methods and terms in molecular biology and genetics include e.g., Sambrook et al., *Molecular Cloning, a Laboratory Manual*, Cold Spring Harbor Press 4th edition (Cold Spring Harbor, N.Y. 2012); Current Protocols in Molecular Biology Volumes 1-3, John Wiley & Sons, Inc. (1994-1998). This disclosure also utilizes routine techniques in the field of biochemistry. Basic texts disclosing the general methods and terms in biochemistry include e.g., *Lehninger Principles of Biochemistry* sixth edition, David L. Nelson and Michael M. Cox eds. W.H. Freeman (2012). This disclosure also utilizes routine techniques in industrial fermentation. Basic texts disclosing the general methods and terms in fermentation include e.g., *Principles of Fermentation Technology,* 3rd Edition by Peter F. Stanbury, Allan Whitaker and Stephen J. Hall. Butterworth-Heinemann (2016); *Fermentation Microbiology and Biotechnology,* 2nd Edition, E. M. T. El-Mansi, C. F. A. Bryce, Arnold L. Demain and A. R. Allman eds. CRC Press (2007). This disclosure also utilizes routine techniques in the field of organic chemistry. Basic texts disclosing the general methods and terms in organic chemistry include e.g., *Practical Synthetic Organic Chemistry: Reactions, Principles, and Techniques*, Stephane Caron ed., John Wiley and Sons Inc. (2011); *The Synthetic Organic Chemist's Companion*, Michael C. Pirrung, John Wiley and Sons Inc. (2007); *Organic Chemistry,* 9th Edition—Francis Carey and Robert Giuliano, McGraw Hill (2013).

For nucleic acids, sizes are given in either kilobases (kb) or base pairs (bp). Estimates are typically derived from agarose or acrylamide gel electrophoresis, from sequenced nucleic acids, or from published DNA sequences. For proteins, sizes are given in kilodaltons (kDa) or amino acid residue numbers. Protein sizes may be estimated from gel electrophoresis, from sequenced proteins, from derived amino acid sequences, or from published protein sequences.

Oligonucleotides that are not commercially available can be chemically synthesized e.g., according to the solid phase phosphoramidite triester method first described by Beaucage & Caruthers, Tetrahedron Letts. 22:1859-1862 (1981), using an automated synthesizer, as described in Van Devanter et al., Nucleic Acids Res. 12:6159-6168 (1984). Purification of oligonucleotides is e.g., by either native acrylamide gel electrophoresis or by anion-exchange HPLC as described in Pearson & Reanier, J. Chrom. 255:137-149 (1983).

The sequence of cloned genes and synthetic oligonucleotides can be verified after cloning using, e.g., the chain termination method for sequencing double-stranded templates of Wallace et al., Gene 16:21-26 (1981).

B. *E. coli* YbgC Thioesterase and Related YbgC-Like Thioesterase Enzymes

1. YbgC Protein structure and Lactonizing Activity

The sequence of wild type *E. coli* ybgC is provided below as SEQ ID NO:1. The *E. coli* ybgC protein also has Uniprot Accession No.: P0A8Z3

MNTTLFRWPVRVYYEDTDAGGVVYHASYVAFYERARTEMLRHHHFSQ QALMAERVAFVVRKMTVEYYAPARLDDMLEIQTEITSMRGTSLVFTQRIVNAENT LLNEAEVLVVCVDPLKMKPRALPKSIVAEFKQ (SEQ ID NO:1)

The wild type *E. coli* ybgC thioesterase SEQ ID NO:1, is generally accepted to function as a acyl-CoA thioestarase (see e.g., Kuznetsova E., et al.; FEMS Microbiol Rev. 2005 April; 29 (2): 263-79).

*E. coli* ybgC is a 134 amino acid protein that is known to function as a thioesterase (E.C 3.1.2.-). The linear protein sequence has been analyzed and the 3-dimensional structure of *E. coli* ybgC has been inferred from sequence information (see e.g., Angelini, A., et al. (2008) Proteins 72:1212-1221; PDB ID code 1S5U).

As disclosed in detail herein, it is shown that in addition to functioning as thioesterases, the family of ybgC enzymes such as e.g., *E. coli* ybgC, also function in the production of lactones. Thus, as disclosed herein, ybgC enzymes can be used in methods for the preparation of lactones. The role of ybgC in the production of lactones has not been appreciated before.

The linear ybgC protein comprises five (5) beta-strand structures (residues 6-11 (β1), 21-23 (β1'), 56-66 (β2), 75-85 (β3), 87-97 (β4) and 103-115 (β35)) and four (4) alpha helical structures (residues 14-16 (α1), 25-42 (α2), 47-52 (α2') and 126-131 (α3)). The monomeric protein folds into a classic hot-dog fold structure wherein the long α2 helix (residues 25-42) is surrounded by four antiparallel β-sheets (β2-β5)) see e.g., Angelini, A., et al. (2008) supra.

The active site residues include Y14, D18, H25, F57 and V58 (see e.g., Angelini, A., et al. (2008) supra). As shown in Example 7 herein below, mutation of the active site residue D18 to A18 (D18A) severely reduces lactone forming activity of the ybgC enzyme. Similarly, mutations at Y14, H25, F57 and V58 to non-conservative amino acid(s) are expected to severely reduce or eliminate lactone forming activity.

Figure 9:
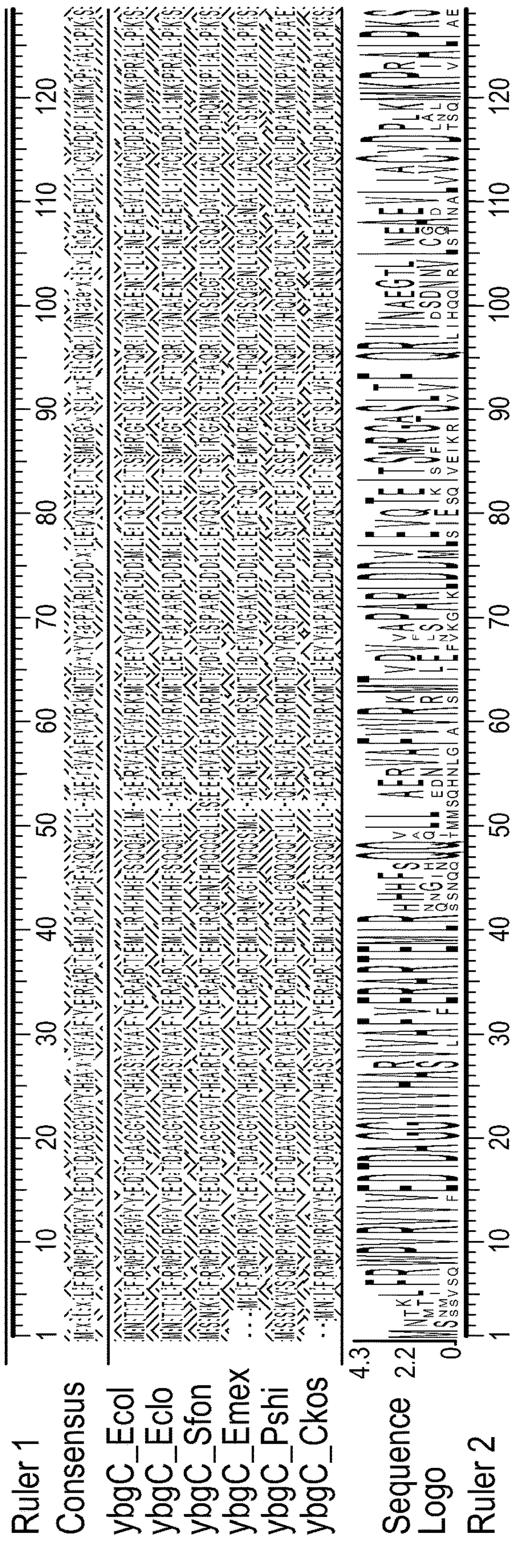
FIG. 9 Illustrates an alignment of six ybgC protiens (SEQ ID NO:1-SEQ ID NO: 6) which have lactonizing activity.

Some residues of ybgC proteins are highly conserved. Non-conservative substitution mutations at these residues are likely to reduce or abolish lactone forming activity. For example, with reference to the *E. coli* sequence, SEQ ID NO: 1 and as shown in FIG. 9, the amino acids corresponding to R11, V12, Y13, Y14, E15, D16, T17, D18, G21, V22, V23, Y24, H25, A26, Y28, V29, F31, E33, R34, A35, R36, T37, E38, F57, V58, V59, Y66, A70, L72, L76, 178, M85, R86, L90, Q94, 196, L104, V109, V112, L124 are highly conserved among the ybgC proteins. Therefore, non-conservative substitution mutations or deletion mutations at these sites are likely to have an effect on lactone forming activity and may reduce lactone forming activity significantly.

Other functional regions include regions having helical domains such as the region encompassing the α2' helical region which is thought to form part of the substrate binding pocket V58 (see e.g., Angelini, A., et al. (2008) supra). Mutations in this region which affect the helical structure or alter the charge profile may affect substrate specificity but are not expected to eliminate lactone forming activity.

Furthermore generally, as to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Such "conservatively modified variants" are likely to have minimal to no effect on protein function especially if they occur in regions that are less highly conserved and are outside of the active site and outside of the regions of helical and/or beta-strand structures.

Conservative substitution tables providing functionally similar amino acids are well known in the art. Such conservatively modified variants are in addition to and do not exclude polymorphic variants, interspecies homologs, and alleles of the invention. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Thomas E. (1992) Proteins: Structures and Molecular Properties).

Thus, in embodiments, the disclosure provides recombinant bacteria that heterologously express a ybgC protein which are useful in methods for the enzymatic production of lactones e.g., γ-, δ- or ε-lactones, under physiological conditions without the need for a chemical conversion step.

2. Assaying for Lactonizing Activity of ybgC and Related ybgC-Like Proteins

In embodiments, lactonizing activity of ybgC and ybgC-like proteins is measured as disclosed e.g., in Examples 1-7 herein below.

In some embodiments, lactonizing activity of ybgC and ybgC-like proteins is measured by measuring the titer of γ-, δ- or ε-lactones produced by a bacterial strain comprising a heterologously expressed ybgC protein (i.e., a test strain) and comparing that value to the titer of the corresponding lactones produced by an appropriate control strain that is isogenic to the test strain except for the YbgC protein that it comprises. Recombinant bacterial strains comprising a heterologously expressed YbgC protein will produce more γ-, δ- or ε-lactones than the control strain when the strains are cultured at a neutral pH.

In some embodiments, the total titer of γ-, δ- or ε-lactones produced are measured and compared between the test and the control strain. In other embodiments, the percent of the total titer of γ-, δ- or ε-lactone produced by a test strain is measured and compared to the percent of the total titer of γ-, δ- or ε-lactone produced by an appropriate control strain that is isogenic to the test strain except for the heterologously expressed YbgC protein.

In exemplary embodiments, Gas-Chromatography with Flame-Ionization Detection (GC-FID) is used to assay the γ-, δ- or &-lactone. GC-FID is known in the art (see e.g., Adlard, E. R.; Handley, Alan J. (2001). *Gas chromatographic techniques and applications*. London: Sheffield Academic). However, any appropriate method for quantitation and analysis may be used e.g., mass spectrometry (MS), Gas Chromatography-mass spectrometry (GC-MS), liquid chromatography-mass spectrometry (LC-MS), thin layer chromatography (TLC), etc.

The lactone can be confirmed e.g., either by using authentic standards or by GC/MS of their dimethyl disulphide (DMDS) adducts (see e.g., Nichols et al. 1986, J. Microbiol. Methods 5:49-55).

3. Bacteria that Enzymatically Produce δ, γ and ε-Lactones

In an exemplary embodiment, the disclosure provides recombinant bacteria that enzymatically produce δ, γ and ε-lactones under physiological conditions e.g., at neutral pH and without raising the temperature of the culture.

In embodiments, an enzymatic pathway for biological/enzymatic production of lactones as disclosed herein comprises an acyl-CoA synthetase (also known as acyl-CoA synthase or acyl-CoA ligase (EC 6.2.1.3)) and a lactone forming or lactonizing enzyme/ybgC protein such as e.g., ybgC from *Escherichia coli* (SEQ ID NO:1).

One example of an acyl-CoA synthetase suitable for use in a recombinant bacterium for the enzymatic production of lactones is e.g., SEQ ID NO:10 (Uniprot accession Q88PT5), herein referred to as fadD3, from *Pseudomonas putida*. Other examples of suitable acyl-CoA synthetases include, but are not limited to acyl-CoA synthetases provided below in Table 1.

TABLE 1

Examples of acyl-CoA synthetases EC 6.2.1.3

| Gene | Uniprot Accession | Organism |
|---|---|---|
| fadD | P69451 | *Escherichia coli* |
| fadD-I | Q88EB7 | *Pseudomonas putida* |
| fadD-II | Q88EB6 | *Pseudomonas putida* |
| PP_0763 "fadD3" | Q88PT5 | *Pseudomonas putida* |
| fatty acid-CoA ligase | A0A069Q372 | *Pseudomonas aeruginosa* |
| fatty acid-CoA ligase | A0A111GPT1 | *Pseudomonas citronellolis* |
| fatty acid-CoA ligase | A4XYJ3 | *Pseudomonas mendocina* |
| IcfB | O07610 | *Bacillus subtilis* |
| FAA1 | P30624 | *Saccharomyces cerevisiae* |

Examples of YbgC proteins (lactonizing enzymes) include, but are not limited to YbgC proteins provided in Table 2 and an alignment of these protein sequences is shown in FIG. 9. Typically, YbgC proteins suitable for use in the methods disclosed herein have at at least 60% sequence identity to SEQ ID NO:1 and have lactonizing activity.

TABLE 2

Examples of ybgC homologs (YbgC proteins)

| Gene | Uniprot Accession | Organism | Conserved amino acids/sequence identity |
|---|---|---|---|
| ybgC | (P0A8Z3) | *Escherichia coli* | 100% |
| ybgC | A0A078LJN7 | *Citrobacter koseri* | 93% |
| ybgC | A0A157YV01 | *Enterobacter cloacae* | 94% |
| Acyl-CoA thioesterase | A0A0F7D2B7 | *Serratia fonticola* | 71% |

TABLE 2-continued

| Examples of ybgC homologs (YbgC proteins) | | | |
|---|---|---|---|
| Gene | Uniprot Accession | Organism | Conserved amino acids/sequence identity |
| Acyl-CoA thioesterase | A0A099DCT9 | *Exiguobacterium mexicanum* | 68% |
| ybgC | A0A1A9AWY4 | *Plesiomonas shigelloides* | 62% |

A recombinant microbe that heterologously expresses a biological pathway comprising a heterologously expressed ybgC protein and a heterologously expressed acyl-CoA synthetase converts 4-hydroxy fatty acids, e.g. 4-hydroxydecanoic acid, 5-hydroxy fatty acids, e.g. 5-hydroxydecanoic acid, and 6-hydroxy fatty acids, e.g. 6-hydroxyhexanoic acid, to the corresponding γ-, δ-, and ε-lactones, respectively, without the need of a chemical step for lactonization, e.g. a chemical step characterized by lowering the pH of the fermentation broth and raising the temperature of the culture.

The 4-, 5-, or 6-hydroxy fatty acid can be provided to the recombinant microbe by (i) adding the 4-, 5-, or 6-hydroxy fatty acid directly to the fermentation medium or (ii) by adding an oleochemical that contains a longer chain hydroxylated fatty acid such as e.g., ricinoleic acid to the fermentation medium or (iii) by having the recombinant microbe endogenously producing 4-, 5-, or 6-hydroxy fatty acids from a simple carbon source.

1. 4-, 5-, or 6-Hydroxy Fatty Acid as Substrates:

In embodiments, the disclosure provides methods for enzymatically producing a lactone under physiological conditions. The method comprises culturing a recombinant bacterium that heterologously expresses a YbgC protein and an acyl-CoA synthetase protein, in a culture medium having a neutral pH. To prepare lactones, the culture of recombinant bacteria is fed an exogenous source of hydroxyl-fatty acids. In one embodiment, the culture of recombinant bacteria is fed an exogenous 4-hydroxy fatty acid and as a result produces a γ-lactone. In one embodiment, the culture of recombinant bacteria is fed an exogenous 5-hydroxy fatty acid and as a result produces a δ-lactone. In one embodiment, the culture of recombinant bacteria is fed an exogenous 6-hydroxy fatty acid and as a result produces an ε-lactone.

In one embodiment, recombinant microbe heterologously expressing an acyl-CoA synthetase, e.g. FadD3 from *P. putida*, and a lactonizing enzyme, e.g. ybgC from *E. coli*, converts exogenously added 4-hydroxydodecanoic acid to γ-dodecalactone without acidification.

In one embodiment, a recombinant microbe heterologously expressing an acyl-CoA synthetase, e.g. FadD3 from *P. putida*, and a lactonizing enzyme, e.g. ybgC from *E. coli*, converts exogenously added 4-hydroxydecanoic acid to γ-decalactone without acidification.

In one embodiment, a recombinant microbe heterologously expressing an acyl-CoA synthetase, e.g. FadD3 from *P. putida*, and a lactonizing enzyme, e.g. ybgC from *E. coli*, converts exogenously added 4-hydroxyoctanoic acid to γ-octalactone without acidification.

In one embodiment, a recombinant microbe heterologously expressing an acyl-CoA synthetase, e.g. FadD3 from *P. putida*, and a lactonizing enzyme, e.g. ybgC from *E. coli*, converts exogenously added 4-hydroxytetradecanoic acid to γ-tetradecalactone without acidification.

In one embodiment, a recombinant microbe heterologously expressing an acyl-CoA synthetase, e.g. FadD3 from *P. putida*, and a lactonizing enzyme, e.g. ybgC from *E. coli*, converts exogenously added 5-hydroxydecanoic acid to 8-decanolactone without acidification.

In one embodiment, a recombinant microbe heterologously expressing an acyl-CoA synthetase, e.g. FadD3 from *P. putida*, and a lactonizing enzyme, e.g. ybgC from *E. coli*, converts exogenously added 6-hydroxydecanoic acid to ε-decanolactone without acidification.

In one embodiment, a recombinant microbe heterologously expressing an acyl-CoA synthetase, e.g. FadD3 from *P. putida*, and a lactonizing enzyme, e.g. ybgC from *E. coli*, converts exogenously added 6-hydroxyhexanoic acid to ε-caprolactone without acidification.

1. Oleochemicals as Substrates:

In embodiments, the disclosure provides methods for enzymatically producing a lactone under physiological conditions. The method comprises culturing a recombinant bacterium that heterologously expresses a YbgC protein and an acyl-CoA synthetase protein, in a culture medium having a neutral pH. To prepare lactones, the culture of recombinant bacteria is fed an exogenous source oleochemicals such as e.g., castor oil, ricinoleic acid ((9z)-12-hydroxy-9-octadecenoic acid), coriolic acid ((9z,11e)-13-hydroxy-9,11-octadecadienoic acid), lesquerolic acid ((11z)-14-hydroxy-11-icosenoic acid), 11-hydroxy palmitic acid, 10-hydroxy stearic acid or 12-hydroxy stearic acid, via fatty acyl chain shortening by β-oxidation. β-oxidation is well known in the art (see e.g., U.S. Pat. No. 9,017,984). β-oxidation of the recombinant microbe may or may not be attenuated or otherwise altered. Except for ricinoleic acid, which is a major component of the oil of castor beans, all other hydroxy fatty acids are not abundant in nature.

Therefore, in an embodiment, a recombinant bacterium is constructed which heterologously expresses a YbgC protein and an acyl-CoA synthetase protein and which also bears either an attenuated or deleted endogenous acyl-CoA dehydrogenase (EC 1.3.99.3). Optionally in an embodiment, a heterologous acyl-CoA dehydrogenase with low activity towards medium-chain acyl-CoAs, e.g. PpACXI from *Prunus persica* (see e.g., Zhang et al., Plant Cell Rep (2017) 36:829-842) or Aox2 from *Yarrowia lipolytica* (see e.g., Wache et al., Appl Microbiol Biotechnol (2003) 61:393-404) can be expressed in place of attenuated or deleted endogenous acyl-CoA dehydrogenase (EC 1.3.99.3)

In an embodiment, a recombinant bacterium is constructed which heterologously expresses a YbgC protein (e.g., SEQ ID NO:1) and an acyl-CoA synthetase protein (e.g., FadD3 from *P. putida*) and also has the acyl-CoA dehydrogenase (fadE, EC 1.3.99.3) deleted, the acetyl-CoA C-acyltransferase (also known as acyl-CoA thiolase, fadA, EC 2.3.1.16) and 3-ketoacyl-CoA reductase/3-hydroxyacyl-CoA dehydrogenase (fadB, 1.1.1.35 3) constitutively expressed or overexpressed and a long-chain acyl-CoA dehydrogenase e.g., Aox2 from *Y. lipolytica* overexpressed, converts exogenously added ricinoleic acid or 12-hydroxystearic to γ-decalactone without acidification.

In an embodiment, a recombinant bacterium is constructed which heterologously expresses a YbgC protein (e.g., SEQ ID NO:1) and an acyl-CoA synthetase protein (e.g., FadD3 from *P. putida*). The recombinant bacterium further has the acyl-CoA dehydrogenase (fadE, EC 1.3.99.3) deleted, the acetyl-CoA C-acyltransferase (also known as acyl-CoA thiolase) (fadA, EC 2.3.1.16) and 3-ketoacyl-CoA reductase/3-hydroxyacyl-CoA dehydrogenase (fadB, 1.1.1.35 3) is either constitutively expressed or over expressed and a long-chain acyl-CoA dehydrogenase such as e.g., Aox2 from *Y. lipolytica* overexpressed, converts exogenously added 10-hydroxystearic acid to γ-dodecalactone without acidification.

3. Simple Carbon Source as Substrate

In further embodiments, the disclosure provides methods for enzymatically producing a lactone under physiological conditions from a simple carbon source. In these embodiments, fatty acid and/or oleochemical feedstocks are not required, as the disclosed recombinant bacteria use simple carbon sources to produce hydroxyl acyl-CoA substrates that are converted to lactones by the recombinant bacterium.

Therefore, the disclosure provides methods for enzymatically producing a lactone under physiological conditions from a simple carbon source wherein the method comprises culturing a recombinant bacterium that heterologously expresses a lactonizing enzyme (e.g., a YbgC protein e.g., SEQ ID NO:1) and an acyl-CoA synthetase protein (e.g., FadD3 from *P. putida*). The recombinant bacterium further comprises a heterologously expressed thioesterase and a fatty acid-hydroxylating enzyme (see e.g., WO 2014/201474 A1), in a culture medium having a neutral pH.

Figure 3:
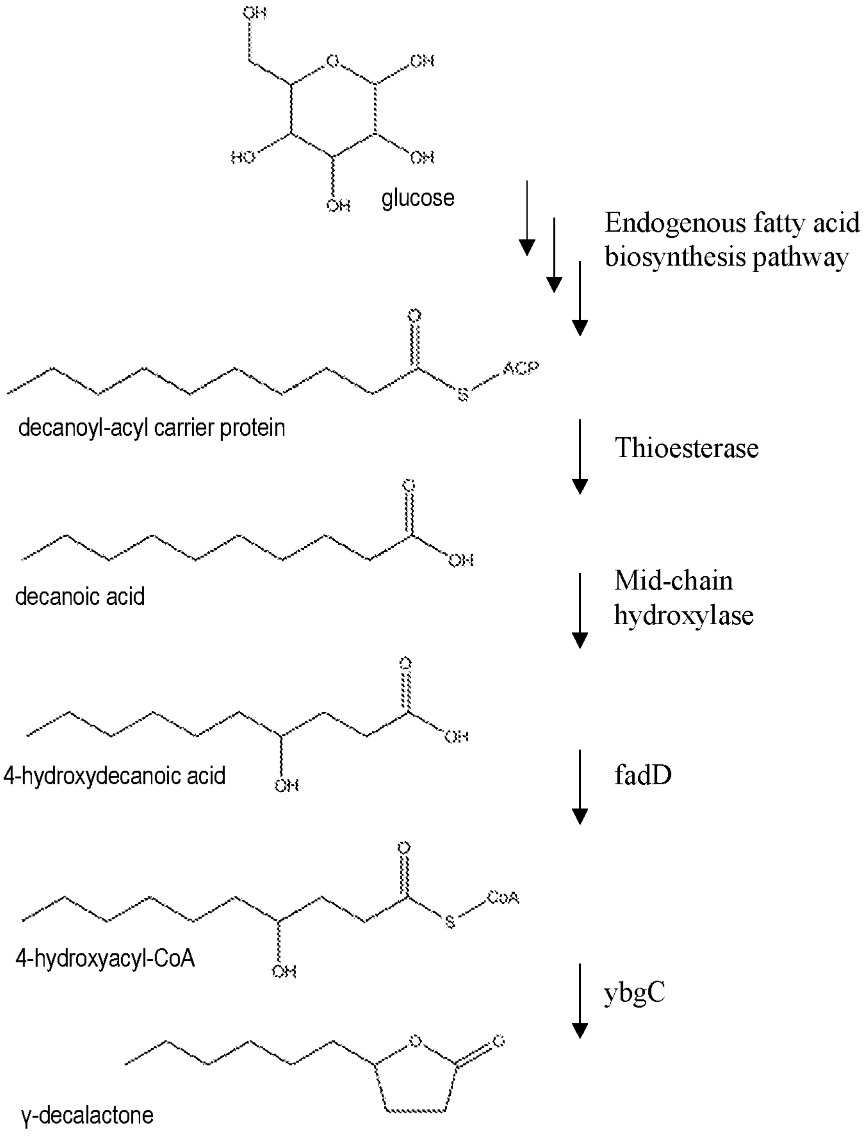
FIG. 3 Illustrates a biochemical pathway converting a simple carbon source to natural γ-decalactone via a medium chain thioester (decanoyl-ACP).
Figure 4:
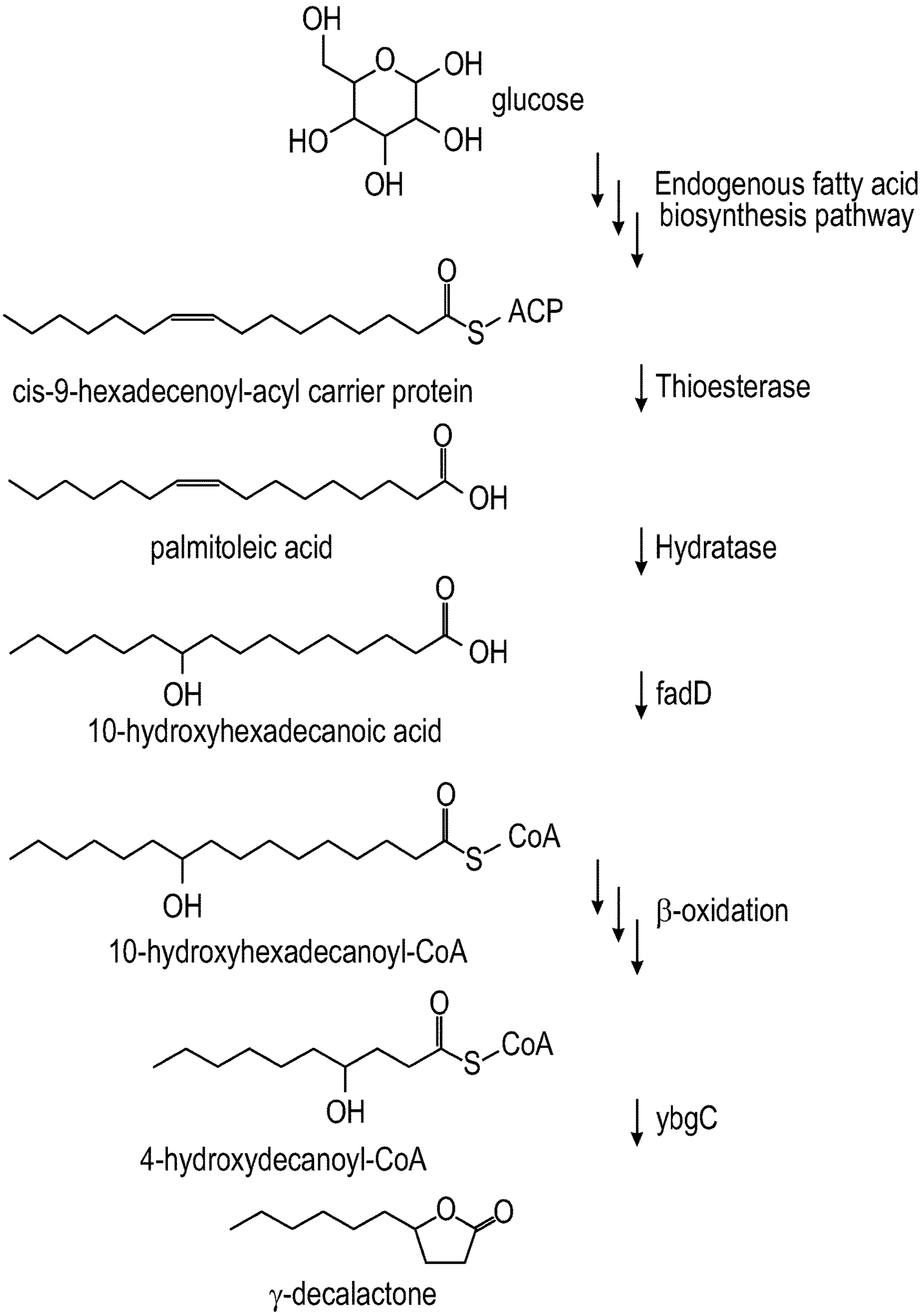
FIG. 4 Illustrates a Illustrates a biochemical pathway converting a simple carbon source to natural γ-decalactone via a long-chain acyl-thioester (palmitoleyl-ACP).
Figure 5A:
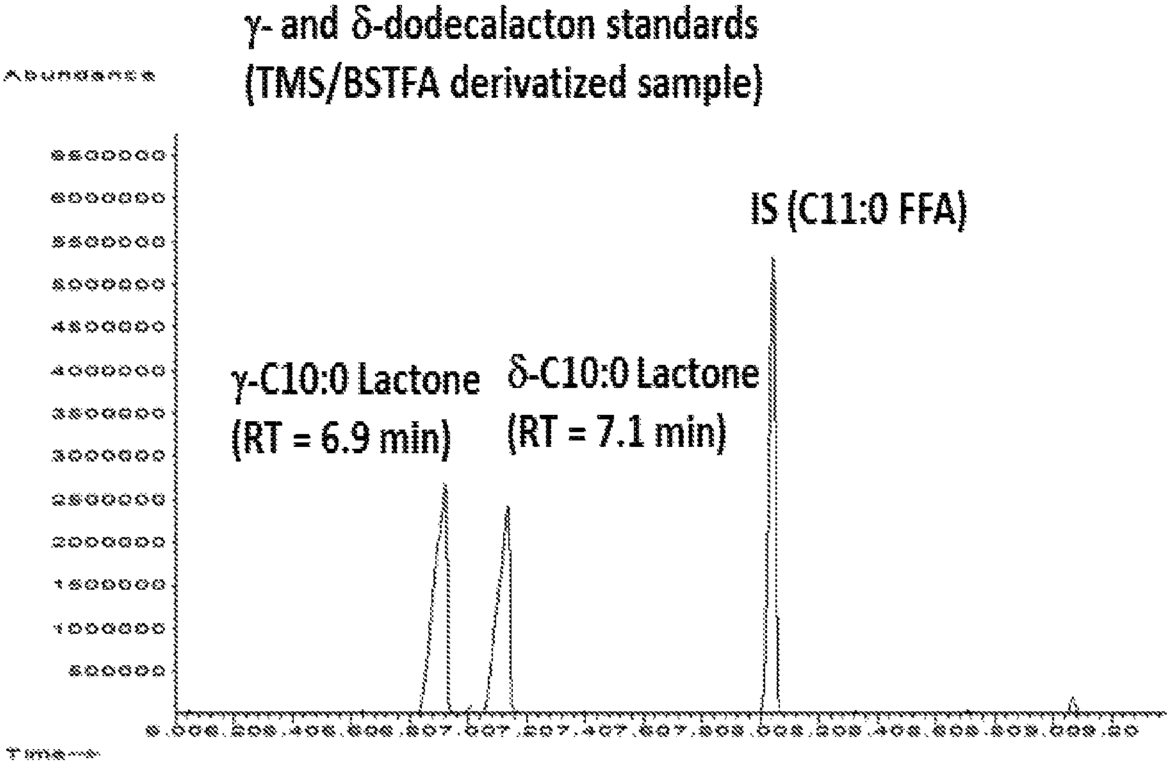
FIG. 5 Illustrates a GC/MS chromatograph of extracts from recombinant *E. coli* strains (B-D) when fed with 4-hydroxy decanoic acid, which was efficiently converted to γ-decalactone by strain sKM.529 expressing FadD3 from *P. putida* and YbgC from *E. coli*. Authentic external and internal standards are shown in (A).
Figure 5B:
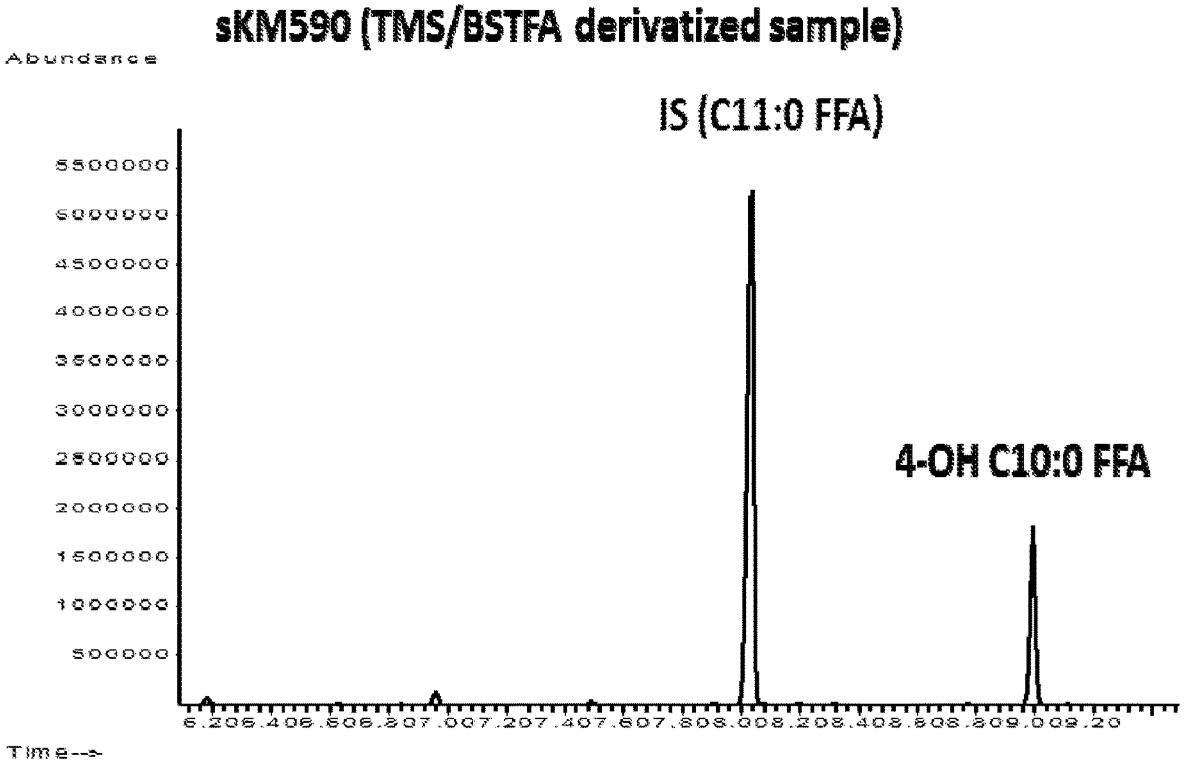
Figure 5C:
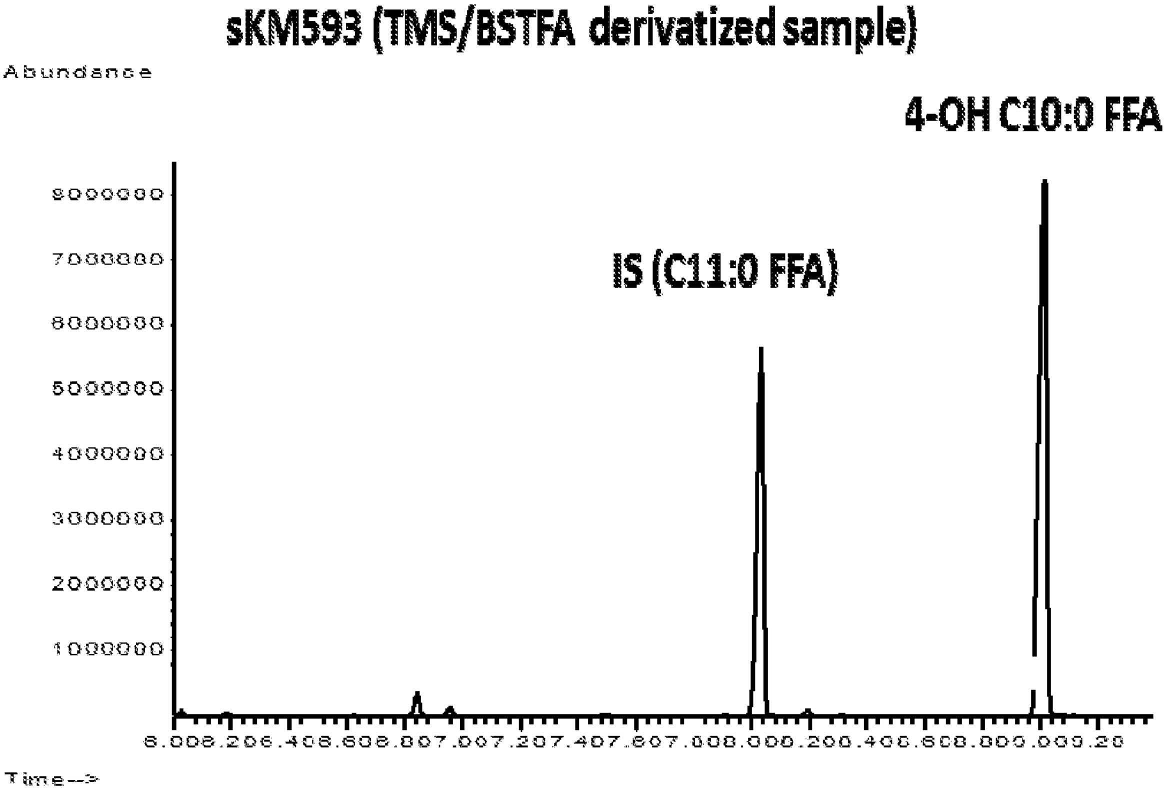
Figure 5D:
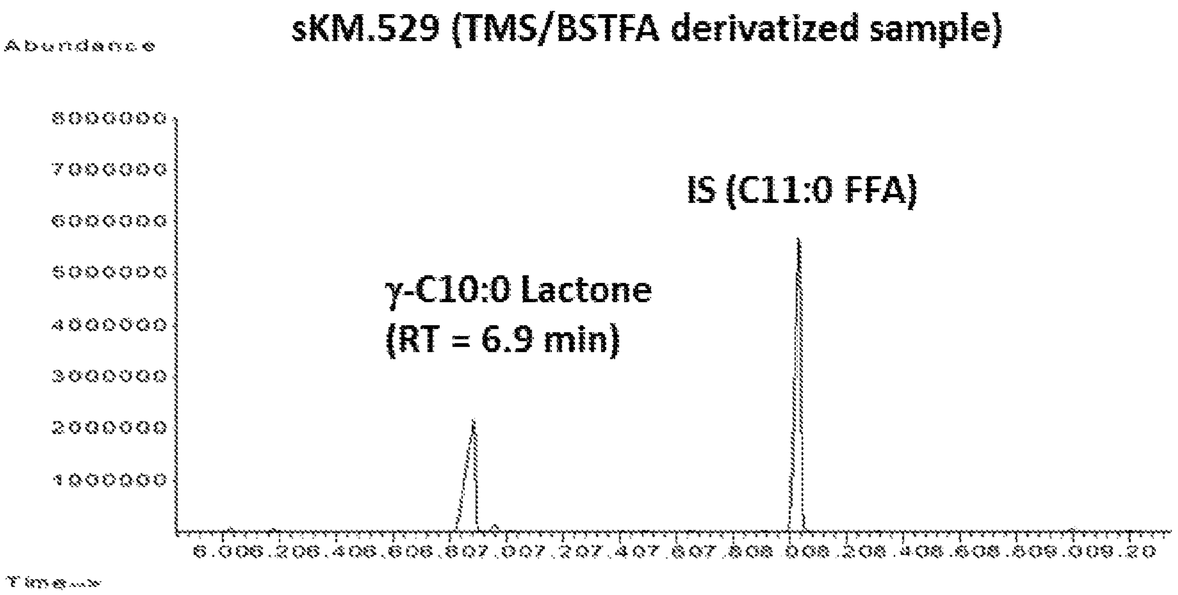

A recombinant bacterium that comprises a heterologously expressed lactonizing enzyme (e.g., YbgC protein, e.g., SEQ ID NO:1) and an acyl-CoA synthetase protein (e.g., FadD3 from *P. putida*) and which heterologously expresses thioesterase and a heterologously expressed fatty acid-hydroxylating enzyme, produces 4-, 5-, or 6-hydroxy fatty acids endogenously from a simple carbon source such as a carbohydrate, e.g. glucose, via an activated acyl-thioester of a medium-chain fatty acid intermediate, e.g. decanoic acid or dodecanoic acid (see e.g., FIG. 3), or via an activated acyl-thioester of a long-chain fatty acid intermediate, e.g. plamitoleic acid or oleic acid (see e.g., FIG. 4).

Thus, a biochemical pathway for the production of γ- or δ-lactones that produces the lactones from a simple carbon source via an activated medium-chain acyl-thioester, e.g. acyl-ACP, contains the following enzymes: a thioesterase, a fatty acid-hydroxylating enzyme, an acyl-CoA synthetase such as e.g., FadD3 from *P. putida* and a lactonizing enzyme such as ybgC from *E. coli*. Examples of suitable thioesterases include but are not limited to those thioesterase enzymes provided in Table 3.

TABLE 3

Examples of thioesterases EC 3.1.2.

| Gene | Uniprot/GenBank Accession | Organism |
|---|---|---|
| FatB1 | Q42561 | *Umbellularia california* |
| FatB1 | Q39473 | *Cinnamomum camphorum* |
| FatB1 | NP_001310677 | *Ricinus communis* |
| FatB2 | Q39514 | *Cuphea hookeriana* |
| FatB2 | Q39555 | *Cuphea palustris* |
| FatB3 | CAB60830 | *Cuphea lanceolata* |
| FatA | NP_189147 | *Arabidopsis thaliana* |
| FatA | XP_021976166 | *Helianthus annuus* |
| FatA1 | ACB29661 | *Macadamia tetraphylla* |

Examples of suitable hydroxylating enzymes include but are not limited to those hydroxylases provided in Table 4. Hydroxylase enzymes suitable for hydroxylating e.g. decanoic acid to 4-hydroxy decanoic acid, can be isolated from microorganisms such as *Mucor circinelloides, Umbellularia isabellina* or *Aspergillus oryzae* (see e.g., U.S. Pat. Nos. 5,457,036 and 7,863,023). Such hydroxylases can be isolated by the following methods: Potential hydroxylases, e.g. cytochrome P450 oxygenases, can be identified from the genome sequences of these microorganisms based on their DNA sequence. The identified hydroxylase genes can be amplified from cDNA and cloned in a bacterial or fungal expression vector. These expression constructs can be transformed in a bacterial, e.g. *Escherichia coli*, or fungal host, e.g. *Saccharomyces cerevisiae*, and the resulting cells or cell extracts can be evaluated in an in-vivo or in-vitro hydroxylase assay that is able to detect the enzymatic conversion of e.g. decanoic acid to 4-hydroxy decanoic acid. Alternatively, or if a genome sequence is unknown, a cDNA expression library can be constructed in a bacterial or fungal expression vector and transformed into in a bacterial, e.g. *Escherichia coli*, or fungal host, e.g. *Saccharomyces cerevisiae*, and the resulting cells or cell extracts can be screened in an in vivo or in vitro hydroxylase assay that is able to detect the enzymatic conversion of e.g. decanoic acid to 4-hydroxy decanoic acid.

TABLE 4

P450 hydroxylases suitable for hydroxylating dodecanoic acid to 5-hydroxy dodecanoic acid

| Name | microorganism | GenBank accession | reference |
|---|---|---|---|
| CYP505E3 | *Aspergillus terreus* | XP_001210151 | WO2017/137935 |
| CYP505Ak | *Aspergillus kawachii* | GAA88365 | WO2017/137935 |
| CYP505E1 | *Aspergillus niger* | CAK39220 | WO2017/137935 |
| CYP505Pe | *Penicillium expansum* | XP_016592781 | WO2017/137935 |
| CYP505An | *Aspergillus niger* | GAQ43769 | WO2017/137935 |
| CYP505Pc | *Penicillium camemberti* | CRL20473 | WO2017/137935 |
| CYP505Pf | *Penicillium freii* | KUM63529 | WO2017/137935 |
| CYP102A1 variants | *Bacillus megaterium* | AAA87602 | Dietrich, Journal of Biotechnology 139 (2009) 115-117 |

Therefore, in an embodiment, a method for producing γ-lactones, from a simple carbon source under physiological conditions comprises culturing a recombinant bacterium that heterologously expresses the following proteins/enzymes: a thioesterase, e.g. FatB1 from *Umbellularia californica*, a fatty acid hydroxylase, from e.g. *Mucor circinelloides, Umbellularia isabellina* or *Aspergillus oryzae*, an acyl-CoA synthetase, e.g. FadD3 from *P. putida*, and a lactonizing enzyme, e.g. ybgC from *E. coli*, produces γ-dodecalactone from a simple carbon source without acidification of the culture medium.

In an embodiment, a method for producing γ-lactones from a simple carbon source under physiological conditions comprises culturing a recombinant bacterium that heterologously expresses the following proteins/enzymes: a thioesterase, e.g. FatB3 from *Cuphea lanceolata*, a fatty acid hydroxylase, e.g. from *Mucor circinelloides, Umbellularia isabellina* or *Aspergillus oryzae*, an acyl-CoA synthetase, e.g. FadD3 from *P. putida*, and a lactonizing enzyme, e.g. ybgC from *E. coli*, produces γ-decalactone from a simple carbon source without acidification.

In an embodiment, a method for producing γ-lactones from a simple carbon source under physiological conditions comprises culturing a recombinant bacterium that heterologously expresses the following proteins/enzymes: a thioesterase, e.g. FatB2 from *Cuphea hookeriana*, a fatty acid hydroxylase, e.g. from *Mucor circinelloides, Umbellularia* isabellina or *Aspergillus oryzae*, an acyl-CoA synthetase, e.g. FadD3 from *P. putida*, and a lactonizing enzyme, e.g.

ybgC from *E. coli*, produces γ-octalactone from a simple carbon source without acidification.

In an embodiment, a method for producing δ-lactones from a simple carbon source under physiological conditions comprises culturing a recombinant bacterium that heterologously expresses the following proteins/enzymes: a thioesterase, e.g. FatB1 from *Umbellularia californica*, a fatty acid hydroxylase, see e.g., Table 4, an acyl-CoA synthetase, e.g. FadD3 from *P. putida*, and a lactonizing enzyme, e.g. ybgC from *E. coli*, produces δ-dodecalactone from a simple carbon source without acidification.

In an embodiment a recombinant bacterium having the endogenous acyl-CoA dehydrogenase gene (fadE, EC 1.3.99.3) deleted, the acetyl-CoA C-acyltransferase (also known as acyl-CoA thiolase) (fadA, EC 2.3.1.16) and 3-ketoacyl-CoA reductase/3-hydroxyacyl-CoA dehydrogenase (fadB, 1.1.1.35 3) either constitutively expressed or over expressed and a long-chain acyl-CoA dehydrogenase such as Aox2 from *Y. lipolytica* overexpressed, and with the expression a thioesterase, e.g. FatA3 from *Arabidopsis thaliana*, a fatty acid hydratase, e.g. OhyA from *Stenotrophomonas maltophilia*, an acyl-CoA synthetase, e.g. FadD3 from *P. putida*, and a lactonizing enzyme, e.g. ybgC from *E. coli*, produces -dodecalactone and -decalactone and from a carbohydrate without acidification.

In an embodiment, biochemical pathways that produce lactones from a simple carbon source in microbial/bacterial strains are expressed in strains that synthesize odd-chain fatty acid (see e.g., U.S. Pat. No. 8,372,610), and the corresponding odd-chain lactones are produced, e.g. natural γ- or δ-nonalactone, γ- or δ-undecalactone, γ- or δ-tridecalactone, etc.

In another embodiment biochemical pathways that produce lactones from a simple carbon source in microbial/bacterial strains that produce branched-chain fatty acid (see e.g., U.S. Pat. No. 8,530,221), the corresponding branched-chain lactones are produced, e.g. natural 9-methyl-γ- or δ-decalactone, 8-methyl-γ- or δ-decalactone, 10-methyl-γ- or δ-undecalactone, 11-methyl-γ- or δ-dodecalactone or 10-methyl-γ- or δ-dodecalactone, etc.

In another embodiment biochemical pathways that produce lactones from a simple carbon source in microbial/bacterial strains that produce ω-7 monounsaturated fatty acid derivatives mono unsaturated lactones are formed originating from the ω7-monounsaturated acyl-fatty acids, e.g. natural (5z)-dodeceno-γ- or δ-lactone, (7z)-tetradeceno-γ- or δ-lactone, etc.

The δ- or γ-lactones produced by this method are chiral molecules. They include all chiral, diastereomeric, and racemic forms of the molecules, including enriched or resolved optical isomers, e.g. (S)-γ-decanolactone, (R)-γ-decanolactone, (S)-δ-decanolactone, (R)-δ-decanolactone, (S)-γ-dodecanolactone, (R)-γ-dodecanolactone, (S)-δ-dodecanolactone, (R)-δ-dodecanolactone, etc.

4. Enzymatically Produced Lactones as Building Blocks for Flavors Fragrances and Other Uses Enzymatically produced lactones such as the enzymatically produced lactones disclosed herein have applications as e.g., fragrances, flavors, nutritional supplements, fuel and etc.

Thus, in some embodiments, enzymatically produced lactones disclosed herein are used alone or in combination with other molecules to provide fragrances and/or flavors for the production of perfume, food, drink, toiletries, etc, nutritional supplements, industrial chemicals, etc.

III. Preparation of Enzymatically Produced Lactones

1. Host Cells and Host Cell Cultures

In view of the present disclosure, the person having ordinary skill in the art will appreciate that any of the embodiments contemplated herein may be practiced with any suitable bacterial host cell that can be genetically modified via the introduction of one or more nucleic acid sequences that code for the appropriate fatty acid biosynthetic enzymes. Accordingly, the recombinant microorganisms disclosed herein function as host cells and comprise one or more polynucleotide sequences that include an open reading frame that encode one or more fatty acid biosynthetic enzymes together with operably-linked regulatory sequences that facilitate heterologous expression of a ybgC protein in the host cell.

Examples of bacteria that provide suitable host cells, include but are not limited to cells from the Class gamma-proteobacteria, cells from the genus *Escherichia, Bacillus, Lactobacillus, Zymomonas, Pseudomonas, Marinobacter*, or *Streptomyces*.

In some exemplary embodiments, the host cell is an *E. coli* cell. In some exemplary embodiments, the *E. coli* cell is a strain B, a strain C, a strain K, or a strain W *E. coli* cell.

2. Expression of Heterologous Enzymatic Activities in Microorganisms

The expression of enzymatic activities in microorganisms and microbial cells for the production of fatty acid derivative molecules is know in the art and is taught e.g., in the following U.S. Pat. Nos. 9,133,406; 9,340,801; 9,200,299; 9,068,201; 8,999,686; 8,658,404; 8,597,922; 8,535,916; 8,530,221; 8,372,610; 8,323,924; 8,313,934; 8,283,143; 8,268,599; 8,183,028; 8,110,670; 8,110,093; and 8,097,439.

Therefore, in exemplary embodiments, the host cells or host microorganisms that heterologously express a ybgC protein also comprise heterologous enzyme activities that make up pathways for the biosynthetic production of fatty acid derivatives.

Typically recombinant bacteria for the enzymatic production of lactones under physiological conditions heterologously express an acyl-CoA synthetase (FadD) (E.C. 6.2.1.3) activity, in addition to heterologously expressed ybgC protein.

In some embodiments, recombinant bacteria for the enzymatic production of lactones under physiological conditions heterologously express a thioesterase e.g., a thioesterase having activity described by EC 3.1.2 . . . . For example a thioesterase as disclosed in Table 3 (supra).

Typically, the enzymatically produced lactones are recovered from the culture medium and/or are isolated from the host cells. In one exemplary embodiment, the enzymatically produced lactones are recovered from the culture medium (extracellular). In another exemplary embodiment, the enzymatically produced lactones are isolated from the host cells (intracellular). In another exemplary embodiment, the enzymatically produced lactones are recovered from the culture medium and isolated from the host cells.

An enzymatically produced lactone composition produced by a host cell can be analyzed using methods known in the art, for example, Gas-Chromatography with Flame Ionization Detection (GC-FID) in order to determine the distribution of enzymatically produced lactones as well as chain lengths and degree of saturation of the components of the enzymatically produced lactone composition. Similarly, other compounds can be analyzed through methods well known in the art.

3. Genetic Alterations for Fine Tuning Recombinant Host Cells

In some exemplary embodiments, host cells comprise optional genetic manipulations and alterations can be used to enhance or otherwise fine tune the production of enzymatically produced lactonesmolecules. As will be appreciated by a person having ordinary skill in the art, optional genetic manipulations can be used interchangeably from one host cell to another, depending on what other heterologous enzymes and what native enzymatic pathways are present in the host cell. Some optional genetic manipulations are discussed below.

FadE

FadE (Acyl-CoA dehydrogenase) catalyzes the first step the first step in fatty acid utilization/degradation (β-oxidation cycle) which is the oxidation of acyl-CoA to 2-enoyl-CoA (see e.g., Campbell, J. W. and Cronan, J. E. Jr (2002) *J. Bacteriol.* 184 (13): 3759-3764, Lennen, R. M. and Pfleger, B. F (2012) Trends Biotechnol. 30 (12): 659-667). Since fadE initiates the β-oxidation cycle, when *E. coli* lacks FadE, it cannot grow on fatty acids as a carbon source (see e.g., Campbell, J. W. and Cronan supra). The same effect can be achieved by attenuating other enzymes from the β-oxidation cycle, e.g. FadA, which is a 3-ketoacyl-CoA thiolase, or FadB, which is a dual 3-hydroxyacyl-CoA-dehydrogenase/dehydratase.

However, when *E. coli* is grown on a carbon source other than fatty acids e.g., grown on sugar, acetate, etc., fadE attenuation is optional because under such conditions fadE expression is repressed by FadR. Therefore, when cells are grown on a simple carbon source such as e.g., glucose, the fadE gene product is already attenuated. Accordingly, when grown on a carbon source other than fatty acids, a fadE mutation/deletion is optional.

Overexpression of Non-Native and/or Native and/or Variants of Genes Involved in the Synthesis of Acyl-ACP In some embodiments, the fatty acid biosynthetic pathway in the production host uses the precursors acetyl-CoA and malonyl-CoA. *E. coli* or other host organisms engineered to overproduce these components can serve as the starting point for subsequent genetic engineering steps to provide the specific output product (such as, fatty acids, fatty esters, hydrocarbons, fatty alcohols). Several different modifications can be made, either in combination or individually, to the host strain to obtain increased acetyl-CoA/malonyl-CoA/fatty acid and fatty acid derivative production see e.g., US Patent Application Publication 2010/0199548.

Other exemplary modifications of a host cell include e.g., overexpression of non-native and/or native and/or variants of genes involved in the synthesis of acyl-ACP. In general, by increasing acyl-ACP synthesis increases the amount of acyl-ACP, which is the substrate of thioesterases, estersynthases and acyl-ACP reductases. Exemplary enzymes that increase acyl-ACP production include e.g., enzymes that make up the "fatty acid synthase" (FAS). As is known in the art (see e.g., US 2010/0199548) FAS enzymes are a group of enzymes that catalyze the initiation and elongation of acyl chains. The acyl carrier protein (ACP) along with the enzymes in the FAS pathway control the length, degree of saturation, and branching of the fatty acids produced. Enzymes that comprise FAS include e.g., AccABCD, FabD, FabH, FabG, FabA, FabZ, FabI, FabK, FabL, FabM, FabQ, FabV, FabX, FabB, and FabF. Depending upon the desired product one or more of these genes can be attenuated or over-expressed.

Therefore, in exemplary embodiments a host strain may overexpress of one or more of the FAS genes. Exemplary FAS genes that may be overexpressed include e.g., fadR from *Escherichia coli* (NP_415705.1) fabA from *Salmonella typhimurium* (NP_460041), fabD from *Salmonella typhimurium* (NP_460164), fabG from *Salmonella typhimurium* (NP_460165), fabH from *Salmonella typhimurium* (NP_460163), fabV from *Vibrio cholera* (YP_001217283), and fabF from *Clostridium acetobutylicum* (NP_350156). In some exemplary embodiments, the overexpression of one or more of these genes, which code for enzymes and regulators in fatty acid biosynthesis, serves to further increase the titer of fatty-acid derivative compounds under particular culture conditions. In some exemplary embodiments, the wild-type *E. coli* strains MG1655 or W3110 (see e.g., Blattner, et al. (1997) 277 (5331): 1453-1462; Jensen, K. F. (1993) *J. Bact.,* 175 (11): 3401-3407) are used as host strains.

4. Methods of Making Recombinant Host Cells and Cultures

Any method known in the art can be used to engineer host cells to produce fatty acid derivatives and/or fatty acid derivative compositions or other compounds. Methods for engineering host cells are well known in the art and are readily appreciated and accessible to the skilled practitioner. See e.g., Sambrook et al. (supra); Current Protocols in Molecular Biology (supra).

Generally, a polynucleotide (or gene) sequence is provided to the host cell by way of a recombinant vector that comprises a promoter operably linked to the fatty acid biosynthetic polynucleotide sequence of interest. Once a polynucleotide sequence(s) encoding fatty acid biosynthetic pathway polypeptide has been prepared and isolated, various methods may be used to construct expression cassettes, vectors and other DNA constructs. The skilled artisan is well aware of the genetic elements that must be present on an expression construct/vector in order to successfully transform, select and propagate the expression construct in host cells. Techniques for manipulation of nucleic acids such as subcloning nucleic acid sequences into expression vectors, labeling probes, DNA hybridization, and the like are described generally in e.g., Sambrook, et al., supra; Current Protocols in Molecular Biology, supra.

A number of recombinant vectors are available to those of skill in the art for use in the stable transformation/transfection of bacteria and other microorganisms (see e.g., Sambrook, et al., supra). Appropriate vectors are readily chosen by one of skill in the art.

Once an appropriate vector is identified and constructed, the appropriate transformation technique is readily chosen by the skilled practitioner. Exemplary transformation/transfection methods available to those skilled in the art include e.g., electroporation, calcium chloride transformation and etc., such methods being well known to the skilled artisan (see e.g., Sambrook, supra). In exemplary embodiments, polynucleotide sequences, comprising open reading frames encoding proteins and operably-linked regulatory sequences can be integrated into a chromosome of the recombinant host cells, incorporated in one or more plasmid expression system resident in the recombinant host cells, or both.

As will be appreciated by those skilled in the art, the design of the expression vector can depend on such factors as e.g., the choice of the host cell to be transformed, the level of expression of polypeptide desired, etc.

IV. Culture and Fermentation of Recombinant Host Cells

As used herein, fermentation broadly refers to the conversion of organic materials into target substances by recombinant host cells. For example, this includes the conversion of a carbon source by recombinant host cells into enzymatically produced lactones as disclosed herein by propagating a culture of the recombinant host cells in a media comprising a carbon source. Conditions permissive for the production of target substances such as e.g., enzymatically produced lactones as disclosed herein, are any conditions that allow a host cell to produce a desired product, such as an enzymatically produced lactone composition. Suitable conditions include, for example, typical fermentation conditions see e.g., *Principles of Fermentation Technology,* 3rd Edition (2016) supra; *Fermentation Microbiology and Biotechnology,* 2nd Edition, (2007) supra.

Fermentation conditions can include many parameters, well known in the art, including but not limited to temperature ranges, pH levels, levels of aeration, feed rates and media composition. Each of these conditions, individually and in combination, allows the host cell to grow. Fermentation can be aerobic, anaerobic, or variations thereof (such as micro-aerobic). Exemplary culture media include broths (liquid) or gels (solid). Generally, the medium includes a carbon source (e.g., a simple carbon source derived from a renewable feedstock) that can be metabolized by a host cell directly. In addition, enzymes can be used in the medium to facilitate the mobilization (e.g., the depolymerization of starch or cellulose to fermentable sugars) and subsequent metabolism of the carbon source to enzymatically produce lactones.

For small scale production, the host cells engineered to enzymatically produced lactone compositions are typically grown in batches of, for example, about 100 μL, 200 μL, 300 μL, 400 μL, 500 μL, 1 mL, 5 mL, 10 mL, 15 mL, 25 mL, 50 mL, 75 mL, 100 mL, 500 mL, 1 L, 2 L, 5 L, or 10 L.

For large scale production, the engineered host cells can be grown in cultures having a volume batches of about 10 L, 100 L, 1000 L, 10,000 L, 100,000 L, 1,000,000 L or larger; fermented; and induced to express any desired polynucleotide sequence.

The non-native monounsaturated fatty acid derivative compositions disclosed herein can be found in the extracellular environment of the recombinant host cell culture and can be readily isolated from the culture medium by methods known in the art. A non-native monounsaturated fatty acid derivative may be secreted by the recombinant host cell, transported into the extracellular environment or passively transferred into the extracellular environment of the recombinant host cell culture.

Exemplary microorganisms suitable for use as production host cells for the production of the enzymatically produced lactones include e.g., bacteria, cyanobacteria, etc. To produce fatty acid derivative compositions production host cells (or equivalently, host cells) are engineered to comprise fatty acid biosynthesis pathways that are modified relative to non-engineered or native host cells e.g., engineered as discussed above and as disclosed e.g., in U.S. Patent Application Publication 2015/0064782. Production hosts engineered to comprise modified fatty acid biosynthesis pathways are able to efficiently convert glucose or other renewable feedstocks into fatty acid derivatives. Protocols and procedures for high density fermentations for the production of various compounds have been established (see, e.g., U.S. Pat. Nos. 8,372,610; 8,323,924; 8,313,934; 8,283,143; 8,268,599; 8,183,028; 8,110,670; 8,110,093; and 8,097,439).

In some exemplary embodiments, a production host cell is cultured in a culture medium (e.g., fermentation medium) comprising an initial concentration of a carbon source (e.g., a simple carbon source) of about 20 g/L to about 900 g/L. In other embodiments, the culture medium comprises an initial concentration of a carbon source of about 2 g/L to about 10 g/L; of about 10 g/L to about 20 g/L; of about 20 g/L to about 30 g/L; of about 30 g/L to about 40 g/L; or of about 40 g/L to about 50 g/L. In some embodiments, the level of available carbon source in the culture medium can be monitored during the fermentation proceeding. In some embodiments, the method further includes adding a supplemental carbon source to the culture medium when the level of the initial carbon source in the medium is less than about 0.5 g/L.

In some exemplary embodiments, a supplemental carbon source is added to the culture medium when the level of the carbon source in the medium is less than about 0.4 g/L, less than about 0.3 g/L, less than about 0.2 g/L, or less than about 0.1 g/L. In some embodiments, the supplemental carbon source is added to maintain a carbon source level of about 1 g/L to about 25 g/L. In some embodiments, the supplemental carbon source is added to maintain a carbon source level of about 2 g/L or more (e.g., about 2 g/L or more, about 3 g/L or more, about 4 g/L or more). In certain embodiments, the supplemental carbon source is added to maintain a carbon source level of about 5 g/L or less (e.g., about 5 g/L or less, about 4 g/L or less, about 3 g/L or less). In some embodiments, the supplemental carbon source is added to maintain a carbon source level of about 2 g/L to about 5 g/L, of about 5 g/L to about 10 g/L, or of about 10 g/L to about 25 g/L.

In one exemplary embodiment the carbon source for the fermentation is derived from a renewable feedstock. In some embodiments, the carbon source is glucose. In other embodiments, the carbon source is glycerol. Other possible carbon sources include, but are not limited to, fructose, mannose, galactose, xylose, arabinose, starch, cellulose, pectin, xylan, sucrose, maltose, cellobiose, and turanose; cellulosic material and variants such as hemicelluloses, methyl cellulose and sodium carboxymethyl cellulose; saturated or unsaturated fatty acids, succinate, lactate, and acetate; alcohols, such as ethanol, methanol, and glycerol, or mixtures thereof. In one embodiment, the carbon source is derived from corn, sugar cane, sorghum, beet, switch grass, ensilage, straw, lumber, pulp, sewage, garbage, cellulosic urban waste, flu-gas, syn-gas, or carbon dioxide. The simple carbon source can also be a product of photosynthesis, such as glucose or sucrose. In one embodiment, the carbon source is derived from a waste product such as glycerol, flu-gas, or syn-gas; or from the reformation of organic materials such as biomass; or from natural gas or from methane, or from the reformation of these materials to syn-gas; or from carbon dioxide that is fixed photosynthetically, for example enzymatically produced lactones may be produced by recombinant cyanobacteria growing photosynthetically and using $CO_2$ as carbon source. In some exemplary embodiments, the carbon source is derived from biomass. An exemplary source of biomass is plant matter or vegetation, such as corn, sugar cane, or switchgrass. Another exemplary source of biomass is metabolic waste products, such as animal matter (e.g., cow manure). Further exemplary sources of biomass include algae and other marine plants. Biomass also includes waste products from industry, agriculture, forestry, and households, including, but not limited to, fermentation waste, ensilage, straw, lumber, sewage, garbage, cellulosic urban waste, municipal solid waste, and food leftovers.

In some exemplary embodiments, enzymatically produced lactones is produced at a concentration of about 0.5 g/L to about 40 g/L. In some embodiments, a fatty acid derivative is produced at a concentration of about 1 g/L or more (e.g., about 1 g/L or more, about 10 g/L or more, about 20 g/L or more, about 50 g/L or more, about 100 g/L or more). In some embodiments, a fatty acid derivative is produced at a concentration of about 1 g/L to about 170 g/L, of about 1 g/L to about 10 g/L, of about 40 g/L to about 170 g/L, of about 100 g/L to about 170 g/L, of about 10 g/L to about 100 g/L, of about 1 g/L to about 40 g/L, of about 40 g/L to about 100 g/L, or of about 1 g/L to about 100 g/L.

In other exemplary embodiments, enzymatically produced lactones are produced at a titer of about 25 mg/L, about 50 mg/L, about 75 mg/L, about 100 mg/L, about 125 mg/L, about 150 mg/L, about 175 mg/L, about 200 mg/L, about 225 mg/L, about 250 mg/L, about 275 mg/L, about 300 mg/L, about 325 mg/L, about 350 mg/L, about 375 mg/L, about 400 mg/L, about 425 mg/L, about 450 mg/L, about 475 mg/L, about 500 mg/L, about 525 mg/L, about 550 mg/L, about 575 mg/L, about 600 mg/L, about 625 mg/L, about 650 mg/L, about 675 mg/L, about 700 mg/L, about 725 mg/L, about 750 mg/L, about 775 mg/L, about 800 mg/L, about 825 mg/L, about 850 mg/L, about 875 mg/L, about 900 mg/L, about 925 mg/L, about 950 mg/L, about 975 mg/L, about 1000 mg/L, about 1050 mg/L, about 1075 mg/L, about 1100 mg/L, about 1125 mg/L, about 1150 mg/L, about 1175 mg/L, about 1200 mg/L, about 1225 mg/L, about 1250 mg/L, about 1275 mg/L, about 1300 mg/L, about 1325 mg/L, about 1350 mg/L, about 1375 mg/L, about 1400 mg/L, about 1425 mg/L, about 1450 mg/L, about 1475 mg/L, about 1500 mg/L, about 1525 mg/L, about 1550 mg/L, about 1575 mg/L, about 1600 mg/L, about 1625 mg/L, about 1650 mg/L, about 1675 mg/L, about 1700 mg/L, about 1725 mg/L, about 1750 mg/L, about 1775 mg/L, about 1800 mg/L, about 1825 mg/L, about 1850 mg/L, about 1875 mg/L, about 1900 mg/L, about 1925 mg/L, about 1950 mg/L, about 1975 mg/L, about 2000 mg/L (2 g/L), 3 g/L, 5 g/L, 10 g/L, 20 g/L, 30 g/L, 40 g/L, 50 g/L, 60 g/L, 70 g/L, 80 g/L, 90 g/L, 100 g/L or a range bounded by any two of the foregoing values. In other embodiments, a fatty acid derivative or other compound is produced at a titer of more than 100 g/L, more than 200 g/L, or more than 300 g/L. In exemplary embodiments, the titer of fatty acid derivative or other compound produced by a recombinant host cell according to the methods disclosed herein is from 5 g/L to 200 g/L, 10 g/L to 150 g/L, 20 g/L to 120 g/L and 30 g/L to 100 g/L. The titer may refer to a particular fatty acid derivative or a combination of fatty acid derivatives or another compound or a combination of other compounds produced by a given recombinant host cell culture. In exemplary embodiments, the expression of ChFatB2 thioesterase variant in a recombinant host cell such as *E. coli* results in the production of a higher titer as compared to a recombinant host cell expressing the corresponding wild type polypeptide. In one embodiment, the higher titer ranges from at least about 5 g/L to about 200 g/L.

In other exemplary embodiments, the host cells engineered to produce enzymatically produced lactones according to the methods of the disclosure have a yield of at least 1%, at least 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, or at least about 30% or a range bounded by any two of the foregoing values. In other embodiments, a fatty acid derivative or derivatives or other compound(s) are produced at a yield of more than about 30%, more than about 35%, more than about 40%, more than about 45%, more than about 50%, more than about 55%, more than about 60%, more than about 65%, more than about 70%, more than about 75%, more than about 80%, more than about 85%, more than about 90%, more than 100%, more than 200%, more than 250%, more than 300%, more than 350%, more than 400%, more than 450%, more than 500%, more than 550%, more than 600%, more than 650%, more than 700%, more than 750%, or more. Alternatively, or in addition, the yield is about 30% or less, about 27% or less, about 25% or less, or about 22% or less. In another embodiment, the yield is about 50% or less, about 45% or less, or about 35% or less. In another embodiment, the yield is about 95% or less, or 90% or less, or 85% or less, or 80% or less, or 75% or less, or 70% or less, or 65% or less, or 60% or less, or 55% or less, or 50% or less. Thus, the yield can be bounded by any two of the above endpoints. For example, the yield of an enzymatically produced lactone e.g., an γ-, δ-, or ε-lactone, produced by the recombinant host cell according to the methods disclosed herein can be about 5% to about 15%, about 10% to about 25%, about 10% to about 22%, about 15% to about 27%, about 18% to about 22%, about 20% to about 28%, about 20% to about 30%, about 30% to about 40%, about 40% to about 50%, about 50% to about 60%, about 60% to about 70%, about 70% to about 80%, about 80% to about 90%, about 90% to about 100%, about 100% to about 200%, about 200% to about 300%, about 300% to about 400%, about 400% to about 500%, about 500% to about 600%, about 600% to about 700%, or about 700% to about 800%. The yield may refer to a particular enzymatically produced lactone or a combination of enzymatically produced lactones. In one embodiment, the higher yield ranges from about 10% to about 800% of theoretical yield. In addition, the yield will also be dependent on the feedstock used.

In some exemplary embodiments, the productivity of the host cells engineered to produce an enzymatically produced lactone according to the methods of the disclosure is at least 100 mg/L/hour, at least 200 mg/L/hour, at least 300 mg/L/hour, at least 400 mg/L/hour, at least 500 mg/L/hour, at least 600 mg/L/hour, at least 700 mg/L/hour, at least 800 mg/L/hour, at least 900 mg/L/hour, at least 1000 mg/L/hour, at least 1100 mg/L/hour, at least 1200 mg/L/hour, at least 1300 mg/L/hour, at least 1400 mg/L/hour, at least 1500 mg/L/hour, at least 1600 mg/L/hour, at least 1700 mg/L/hour, at least 1800 mg/L/hour, at least 1900 mg/L/hour, at least 2000 mg/L/hour, at least 2100 mg/L/hour, at least 2200 mg/L/hour, at least 2300 mg/L/hour, at least 2400 mg/L/hour, 2500 mg/L/hour, or as high as 10 g/L/hour (dependent upon cell mass). The productivity may refer to a particular enzymatically produced lactones e.g., a γ-lactone, or a combination of enzymatically produced lactones or other compound(s) produced by a given host cell culture. For example, the heterologous expression of a YbgC protein and an acyl-CoA synthetase in a recombinant host cell such as *E. coli* results in increased productivity of the enzymatically produced lactones as compared to a recombinant host cell that does not heterologously express (overexpress a native *E. coli* YbgC or heterologous YbgC from and organism other than *E. coli*) a YbgC protein and an acyl-CoA synthetase. In exemplary embodiments, higher productivity ranges from about 0.3 g/L/h to about 3 g/L/h to about 10 g/L/h to about 100 g/L/h to about a 1000 g/L/h.

As disclosed supra, in some exemplary embodiments, the host cell used in the fermentation procedures discussed herein (supra) is a mammalian cell, plant cell, insect cell, yeast cell, fungus cell, filamentous fungi cell, an algal cell, a cyanobacterial cell, and bacterial cell.

V. Isolation

Bioproducts e.g., compositions comprising enzymatically produced lactones as disclosed herein which are produced utilizing recombinant host cells as discussed above are typically isolated from the fermentation broth by methods known in the art. In an exemplary embodiment the compositions comprising the enzymatically produced lactones as disclosed herein which are produced utilizing recombinant host cells are discussed above are isolated from the fermentation broth by gravity settling, centrifugation, or decantation.

VI. Compositions and Formulations of Enzymatically Produced Lactones

Bioproducts e.g., compositions comprising enzymatically produced lactones produced utilizing engineered bacteria as discussed herein, are produced from renewable sources (e.g., from a simple carbon source derived from renewable feedstocks) and, as such, are new compositions of matter. These new bioproducts can be distinguished from organic compounds derived from petrochemical carbon on the basis of dual carbon-isotopic fingerprinting or $^{14}C$ dating. Additionally, the specific source of biosourced carbon (e.g., glucose vs. glycerol) can be determined by dual carbon-isotopic fingerprinting by methods known in the art (see, e.g., U.S. Pat. No. 7,169,588, WO 2016/011430 A1, etc.).

The following examples are offered to illustrate, but not to limit the invention.

EXAMPLES

Example 1

The following Example illustrates materials and methods for Examples 2-9 disclosed herein below.

Methods

Small Scale Fermentation Protocol:

40 μL LB culture (from an LB culture growing in a 96 well plate) was used to inoculate 360 μL LB media, which was then incubated for approximately 4 hours at 32° C. shaking. 80 μL of the LB seed was used to inoculate 320 μL Nlim media (Table 5). After growing at 32° C. for 2 hours, the cultures were induced with IPTG (final concentration 1 mM). The cultures were then incubated at 32° C. with shaking for 20 hours if not noted otherwise, after which they were extracted following the standard extraction protocol detailed below.

TABLE 5

| N-lim Media Formulation<br>N-lim Media Formulation | | |
|---|---|---|
| 1 | X | 5x Salt Soln. with NH4Cl |
| 1 | X | 1000x Trace Vitamins |
| 1 | mg/L | 10 mg/mL Thiamine |
| 1 | mM | 1M MgSO4 |
| 0.1 | mM | 1M CaCl2 |
| 40 | g/L | 500 g/L glucose |
| 1 | X | 1000x Trace minerals |
| 10 | mg/L | 10 g/L Fe Citrate |
| 100 | μg/mL | 100 mg/ml spectinomycin |
| 100 | mM | 2M BisTris (pH7.0) |
| 0.5 | mM | Aminolevulinic acid |

Fatty Acid Species Standard Extraction and Analytical Protocol

To each well to be extracted, 80 μL of 1M HCl, followed by 400 μL of butyl acetate containing 500 mg/L 1-undecanol or 500 mg/L undecanoic acid as internal standard (IS) was added as internal standard (IS) was added. The 96 well plates were then heat-sealed using a plate sealer (ALPS-300 heater; Abgene, ThermoScientific, Rockford, IL), and shaken for 15 minutes at 2000 rpm using MIXMATE mixer (Eppendorf, Hamburg, Germany). After shaking, the plates were centrifuged for 10 minutes at 4500 rpm at room temperature (Allegra X-15R, rotor SX4750A, Beckman Coulter, Brea, CA) to separate the aqueous and organic layers. 50 μL of the organic layer was transferred to a 96 well plate (polypropylene, Corning, Amsterdam, The Netherlands) and derivatized with 50 μL of trimethylsiloxy/N,O-Bis(trimethylsilyl) trifluoroacetamide (TMS/BSTFA). The plate was subsequently heat sealed and stored at −20° C. until evaluated by either Gas Chromatography with Flame Ionization Detection (GC-FID) or Gas Chromatography-Mass Spectrometry (GC-MS).

The GC-MS parameters used to generate chromatograms and mass spectra for compounds identification were as follows: 1 μl sample was injected into analytical Column: DB-1HT, 15m×250 μm×0.1 μm, available from Agilent with cat #J&W 122-1111E, Oven temperature: initial at 50° C., hold for 5 minutes, increase to 300° C. at 25° C./min, and hold for 5.24 minutes for a total run time of 24 minutes. Column flow: 1.2 mL/min, Inlet temperature: 300° C., Split ratio: 20:1, Software: ChemStation E.02.01.1177. MS parameters: Transfer line temperature: 300° C., MS source: 230° C., MS Quad: 150° C. Auto sampler: Combi PAL (CTC analytics) distributed by LEAP Technologies. The GC-FID parameters used to quantify each compound were carried out as follows: 1 μL of sample was injected onto an analytical column (UFC Rtx-1, 5 M×0.1 mm×0.1 μM) in a Thermo Fisher UltraFast TRACE GC (Thermo Fisher Scientific, West Palm Beach, FL). Oven temperature: initial at 100° C., hold for 0.2 minutes, increase to 320° C. at 100° C./min, and hold for 0.5 minutes for a total run time of 2.5 minutes using column flow of 0.5 ml/min, Inlet temperature: 300° C. and flame ionization detector temperature: 300° C.

The protocol detailed above represents standard conditions, a person having ordinary skill in the art appreciates that the protocol may be modified to optimize the analytical results.

TABLE 6

Strains used for bioconversion of hydroxy fatty acids to lactones

| Strain Name | Description |
|---|---|
| DS08-004 | MG1655 ΔfadD |
| sKM.564 | MG1655 ΔfadD AybgC |
| VA1052 | MG1655 ΔfadD::Ptrc-fadD3_Pput |
| sKM.565 | MG1655 ΔfadD::Ptrc-fadD3_Pput, ΔybgC |

TABLE 6-continued

| Strains used for bioconversion of hydroxy fatty acids to lactones | |
|---|---|
| Strain Name | Description |
| sKM.589 | DS08-004 with empty pCL plasmid |
| sKM.590 | DS08-004 with pKM.122 (pCL-Ptrc-ybgC) |
| sKM.591 | sKM.564 with empty pCL plasmid |
| sKM.528 | VA1052 with empty pCL plasmid |
| sKM.593 | sKM.565 with empty pCL plasmid |
| sKM.529 | VA1052 with plasmid pKM.122 (pCL-Ptrc-ybgC) |
| sKM.594 | sKM.565 with plasmid pKM.122 (pCL-Ptrc-ybgC) |

Example 2

The following Example illustrates conversion of 4-hydroxydecanoic acid to γ-decalactone by *E. coli* strains expressing acyl CoA synthase and ybgC.

This Example shows the conversion of 4-hydroxydecanoic acid to γ-decalactone by recombinant *E. coli* MG1655 derivative strains expressing acyl-CoA synthetase and ybgC. Several base strains were created by deleting from the chromosome either the endogenous acyl-CoA synthase gene, fadD, or the endogenous ybgC gene, or by deleting both genes (see Table 6). Additionally in selected strains, the fadD3 gene from *Pseudomonas putida* was cloned under the control of the IPTG-inducible Ptrc promoter and integrated into the fadD locus for heterologous expression from the *E. coli* chromosome (see Table 6). The YbgC gene was amplified from genomic DNA and cloned into a pCL-derivative vector (SC101 replicon, spectinomycin resistance marker) such that it was under the control of the IPTG-inducible Ptrc. The plasmid was named pKM. 122.

Plasmid pKM. 122 or the empty pCL-control plasmid were transformed into the base strains and the resulting strains (see Table 6) were then grown as disclosed in Example 1 and 4-hydroxydecanoic acid was added to culture media as disclosed in Example 1. After 20 h, the cultures were extracted as disclosed in Example 1. The chromatographs of the extracts from three strains compared to authentic γ- and δ-decalactone are shown in FIG. 5. Strains with deletion of the endogenous acyl-CoA-dehydrogenase and ybgC genes, sKM.589 and sKM.591, showed only trace amounts of γ-decalactone. Similarly, the strain with the ybgC gene deleted and FadD3 from *P. putida* overexpressed (sKM.593) showed only trace amounts of γ-decalactone (see Table 7). These results demonstrate that 4-hydroxydecanoic acid or 4-hydroxydecanoyl-CoA do not spontaneously lactonize to form γ-decalactone without acidification of the culture broth.

Figure 6A:
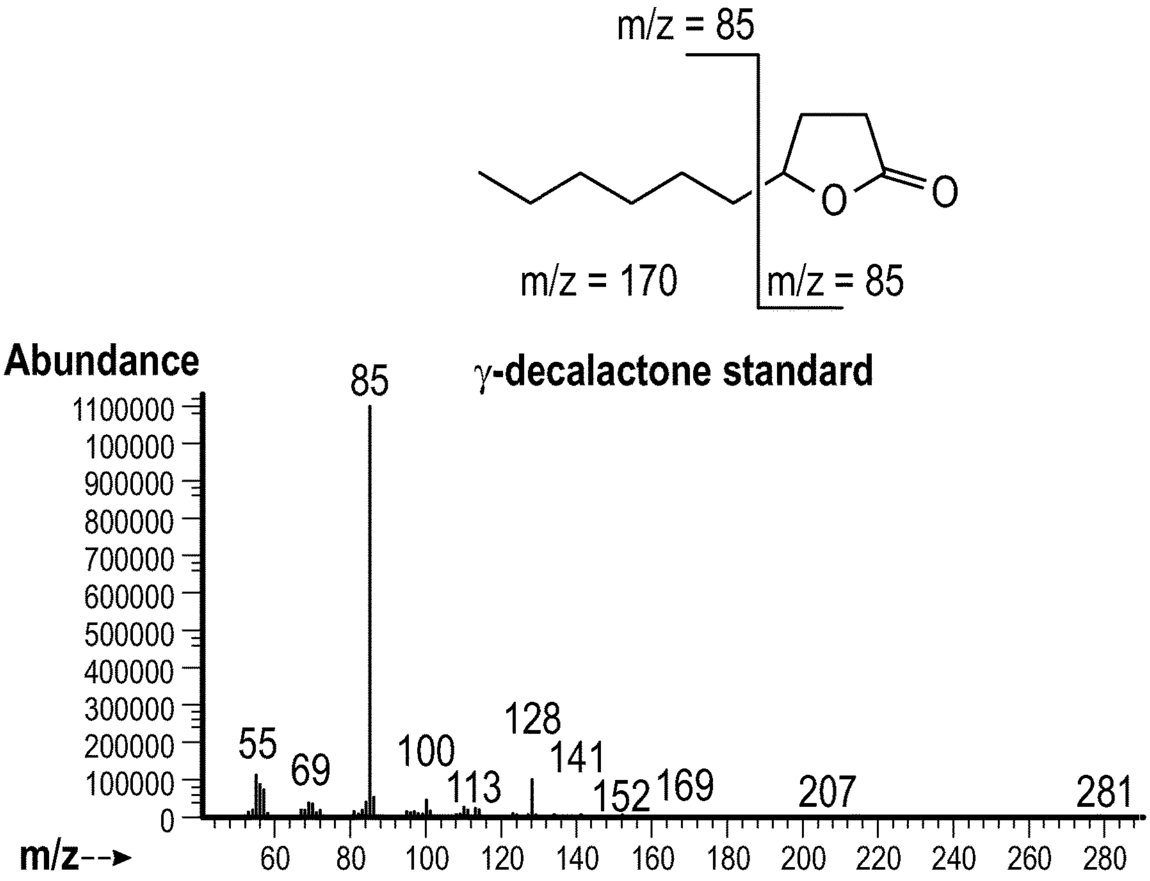
FIG. 6 Illustrates the mass spectrum and ion fragmentation pattern of γ-decalactone authentic standard and the peak at RT=6.9 min from FIG. 3D, minutes), which are identical.
Figure 6B:
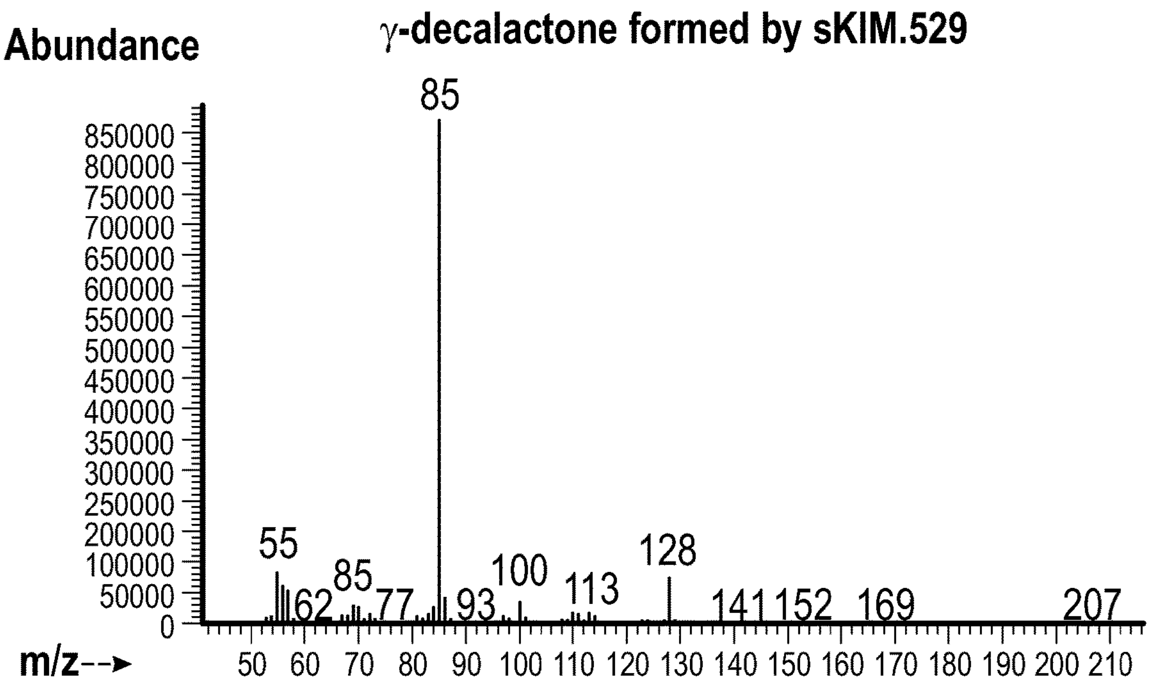
Figure 7A:
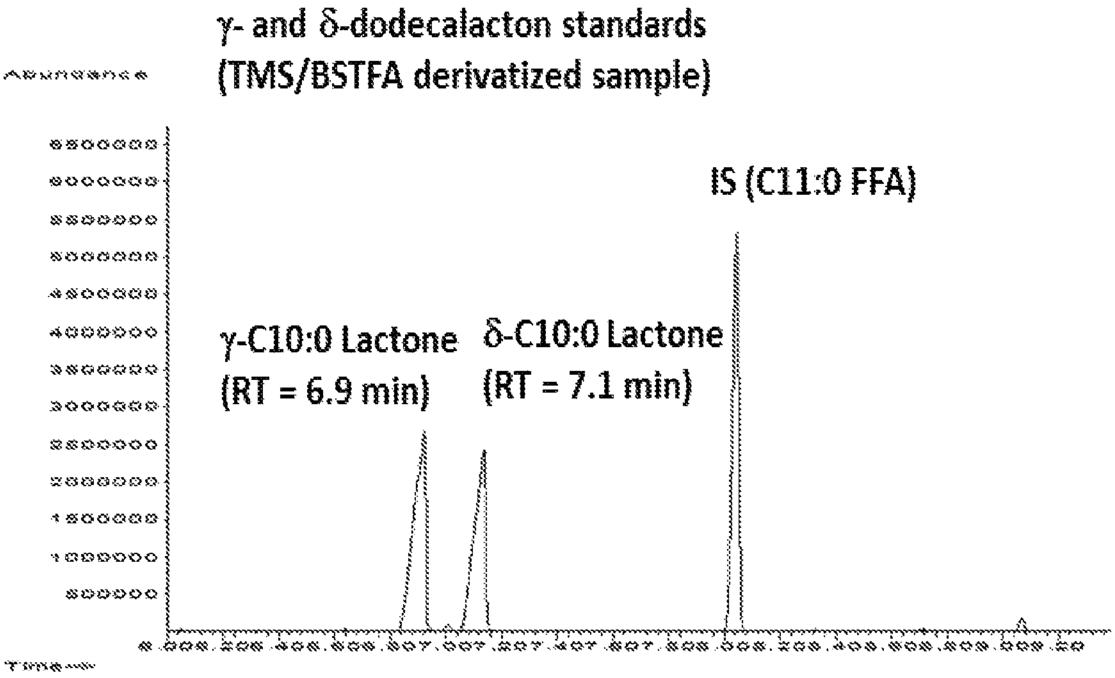
FIG. 7 Illustrates a GC/MS chromatograph of extracts from recombinant *E. coli* strains (B-D) when fed with 5-hydroxy decanoic acid, which was efficiently converted to γ-decalactone by strain sKM.529 expressing FadD3 from *P. putida* and YbgC from *E. coli*. Authentic external and internal standards are shown in (A).
Figure 7B:
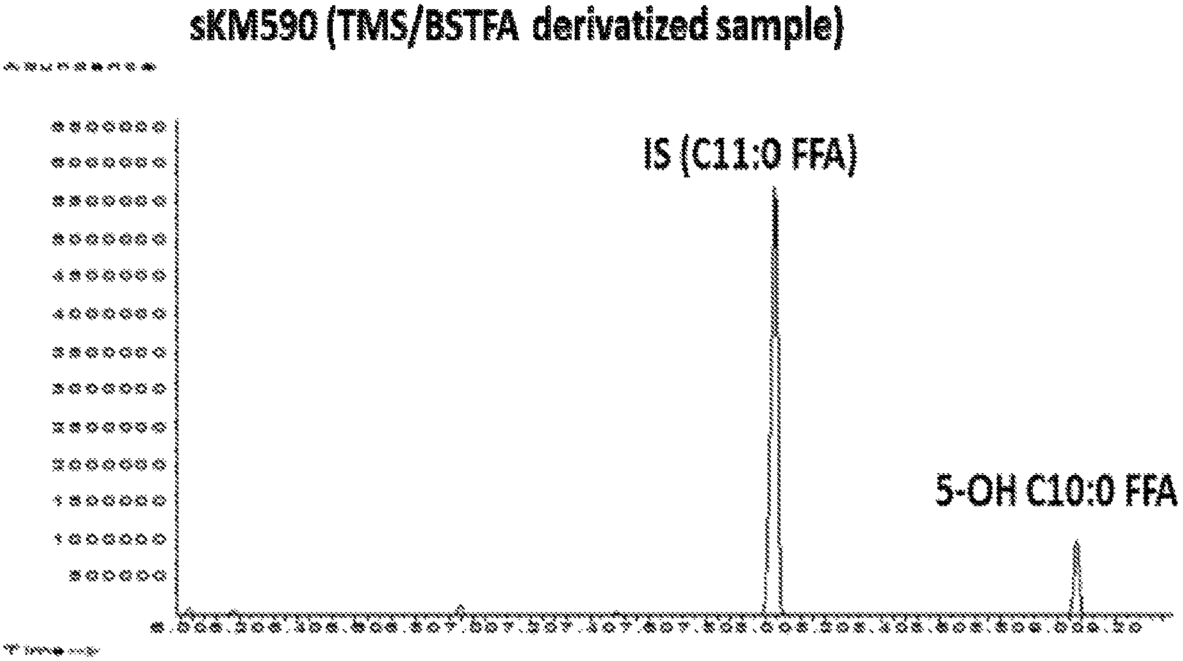
Figure 7C:
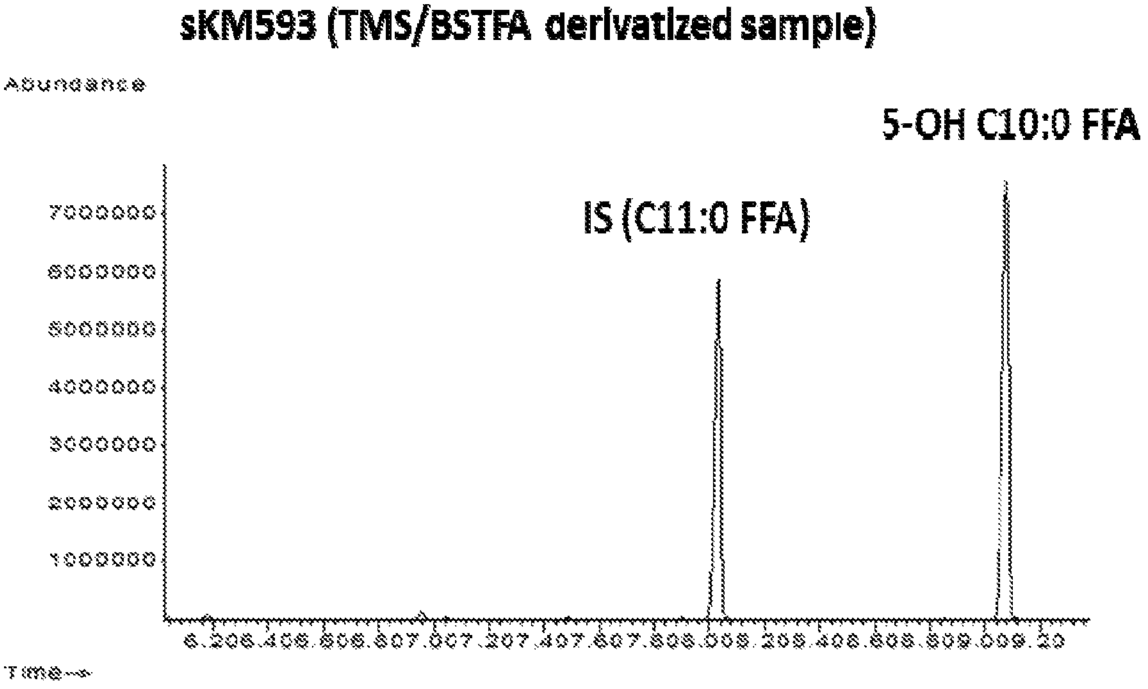
Figure 7D:
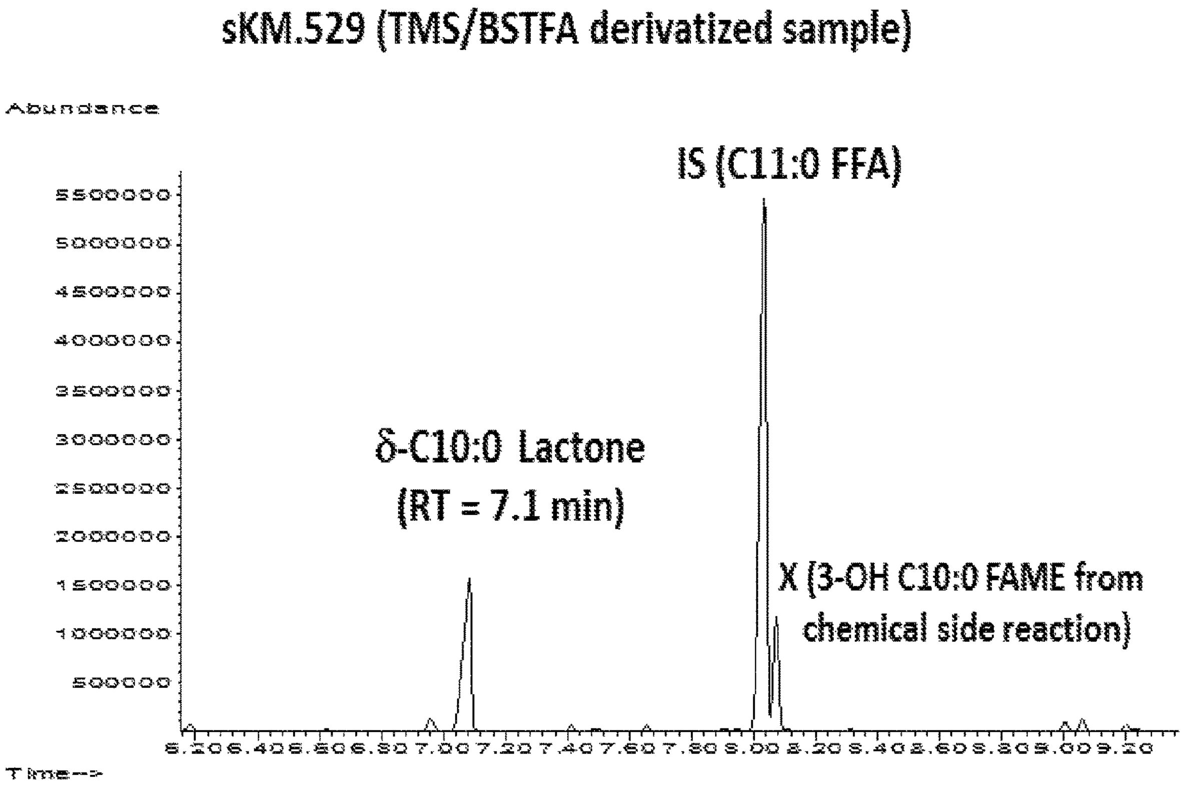

In contrast, the strain with the intact chromosomal copy of the ybgC gene and FadD3 from *P. putida* overexpressed, sKM.528, showed 82% conversion of 4-hydroxydecanoic acid to γ-decalactone, and the two strains with FadD3 from *P. putida* and YbgC overexpressed, sKM.529 and sKM.594, showed complete (100%) and almost complete (96%) conversion of 4-hydroxydecanoic acid to γ-decalactone, respectively (see Table 7). The new peak at RT=6.9 min was identified as γ-decalactone by its retention time (FIG. 5) and fragmentation pattern (see FIG. 6), which matched the authentic standard.

These results demonstrated that the combined expression of YbgC and FadD3 from *P. putida* were sufficient to convert 4-hydroxydecanoic acid to γ-decalactone in-vivo, i.e. under physiological conditions without the need to acidify the culture broth.

TABLE 7

Bioconversion of 4-hydroxydecanoic acid to γ-decalactone in recombinant *E. coli*.

| Strain | Deleted gene | Overexpressed genes | Conversion (%) |
|---|---|---|---|
| MG1655 | — | — | 0 |
| sKM.589 | fadD | — | 1 |
| sKM.590 | fadD | ybgC | 3 |
| sKM.591 | fadD, ybgC | — | 2 |
| sKM.528 | — | fadD3 | 82 |
| sKM.529 | — | fadD3, ybgC | 100 |
| sKM.593 | ybgC | fadD3 | 1 |
| sKM.594 | ybgC | fadD3, ybgC | 96 |

Example 3

The following Example illustrates conversion of 5-hydroxydecanoic acid to 8-decalactone by *E. coli* strains expressing acyl CoA synthetase and ybgC.

This Example shows the conversion of exogenously added 5-hydroxydecanoic acid to δ-decalactone by recombinant *E. coli* strains expressing acyl-CoA synthetase and ybgC. The same strains as in Example 2 were used for this example.

The strains (see Table 6) were grown as disclosed in Example 1 and 5-hydroxydecanoic acid was added to culture media as disclosed in Example 1. After 20 h, the cultures were extracted as disclosed in Example 1. The chromatographs of the extracts from three strains compared to authentic γ- and δ-decalactone are shown in FIG. 7.

Strains with deletion of the endogenous acyl-CoA-dehydrogenase and ybgC genes, sKM.589 and sKM.591, showed no detectable amounts of δ-decalactone. Similarly, the strain with the ybgC gene deleted and FadD3 from *P. putida* overexpressed (sKM.593) showed no detectable amounts of δ-decalactone (see Table 8). These results demonstrate that 5-hydroxydecanoic acid or 5-hydroxydecanoyl-CoA do not spontaneously lactonize to form δ-decalactone without acidification of the culture broth.

Figure 8A:
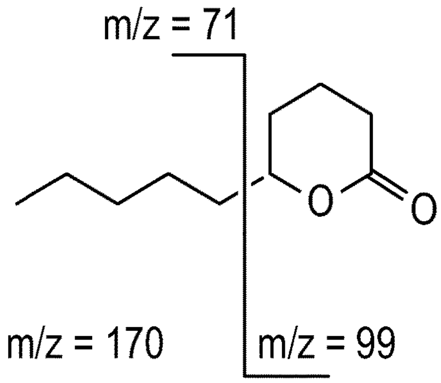
FIG. 8 Illustrates the mass spectrum and ion fragmentation pattern of δ-decalactone authentic standard and the peak at RT=6.9 min from FIG. 3D, minutes), which are identical.
Figure 8A:
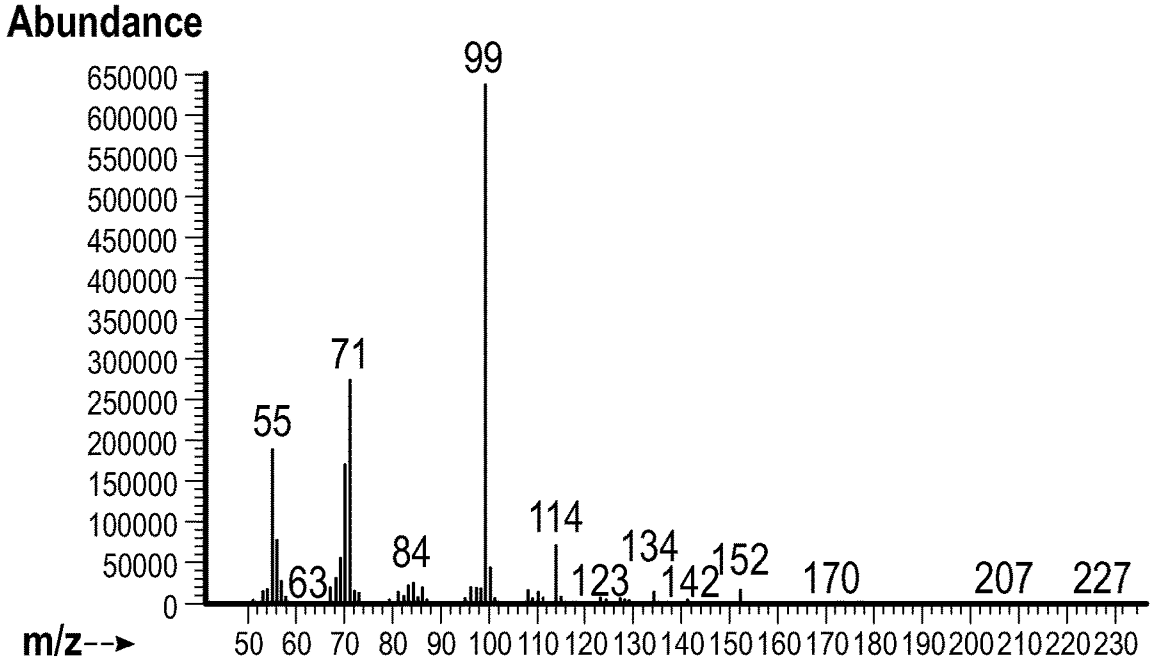
Figure 8B:
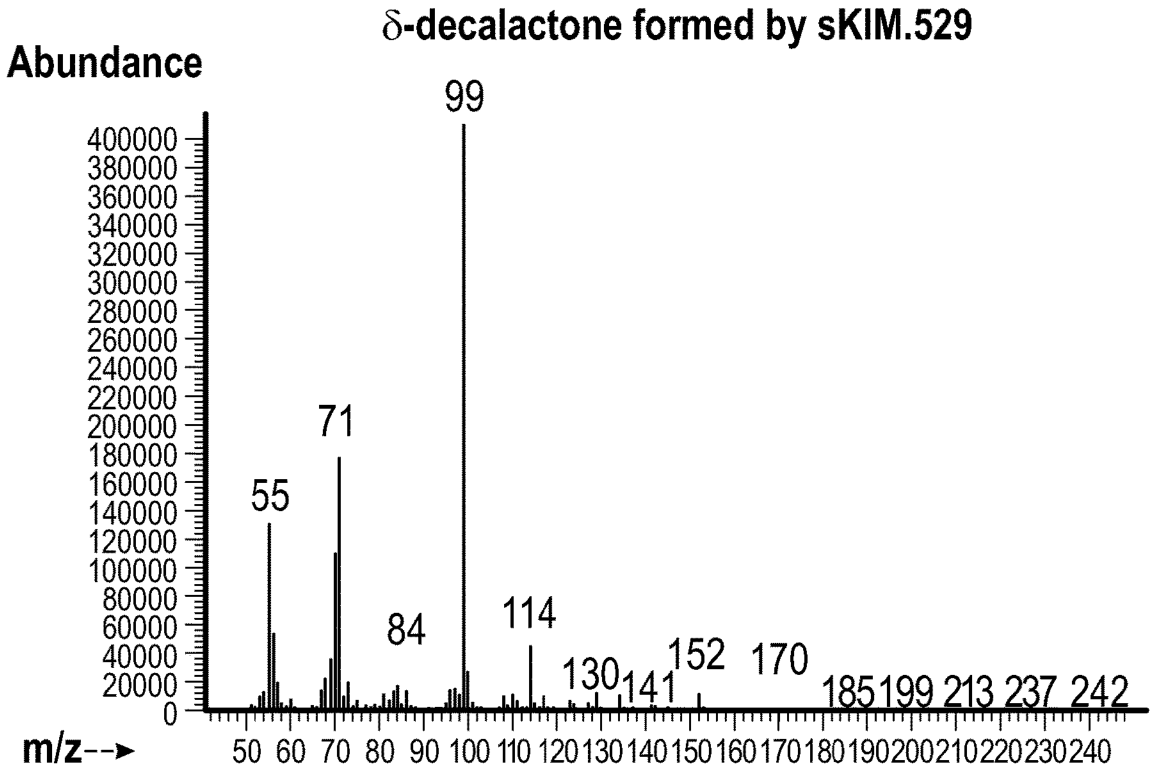

In contrast, the strain with the intact chromosomal copy of the ybgC gene and FadD3 from *P. putida* overexpressed, sKM.528, showed 10% conversion of 5-hydroxydecanoic acid to δ-decalactone, and the two strains with FadD3 from *P. putida* and YbgC overexpressed, sKM.529 and sKM.594, showed almost complete (91 and 96%) conversion of 5-hydroxydecanoic acid to δ-decalactone (see Table 8). The new peak at RT=7.1 min was identified as δ-decalactone by its retention time (FIG. 7) and fragmentation pattern (see FIG. 8), which matched the authentic standard.

These results demonstrated that the combined expression of YbgC and FadD3 from *P. putida* were sufficient to convert 5-hydroxydecanoic acid to δ-decalactone in-vivo, i.e. under physiological conditions without the need to acidify the culture broth.

TABLE 8

Bioconversion of 5-hydroxydecanoic acid to δ-decalactone in recombinant *E. coli.*

| Strain | Deleted genes | Overexpressed genes | Conversion 0 |
|---|---|---|---|
| MG1655 | — | — | 0 |
| sKM.589 | fadD | — | 0 |
| sKM.590 | fadD | ybgC | 0 |
| sKM.591 | fadD, ybgC | — | 0 |
| sKM.528 | — | fadD3 | 10 |
| sKM.529 | — | fadD3, ybgC | 91 |
| sKM.593 | ybgC | fadD3 | 0 |
| sKM.594 | ybgC | fadD3, ybgC | 96 |

Example 4

The following Example illustrates conversion of 6-hydroxyhexanoic acid to &-lactone by *E. coli* strains expressing acyl CoA synthetase and ybgC.

This Example shows the conversion of exogenously added 6-hydroxyhexanoic acid to ε-lactone by recombinant *E. coli* strains expressing acyl-CoA synthetase and ybgC. Strains from Example 2 were used for this Example.

The strains (see Table 6) were grown as disclosed in Example 1 and 6-hydroxyhexanoic acid was added to culture media as disclosed in Example 1. After 20 h, the cultures were extracted as disclosed in Example 1. The chromatographs of the extracts from two strains were compared to authentic ε-caprolactone.

The strain with the ybgC gene deleted and FadD3 from *P. putida* overexpressed (sKM.593) showed no detectable amounts of ε-caprocalactone (see Table 9). These results demonstrate that 6-hydroxyhexanoic acid or 6-hydroxyhexanoyl-CoA do not spontaneously lactonize to form ε-lactone without acidification of the culture broth.

In contrast, the strain with FadD3 from *P. putida* and YbgC overexpressed, sKM.594, showed 52% conversion of 6-hydroxyhexanoic acid to ε-lactone (see Table 9). The new peak was identified as ε-caprolactone by its retention time and fragmentation pattern, which matched the authentic standard (data not shown).

These results demonstrated that the combined expression of YbgC and FadD3 from *P. putida* were sufficient to convert 6-hydroxyhexanoic acid to ε-caprolactone in-vivo, i.e. under physiological conditions without the need to acidify the culture broth.

TABLE 9

Bioconversion of 6-hydroxyhexanoic acid to ε-caprolactone in recombinant *E. coli.*

| Strain | Deleted genes | Overexpressed genes | Conversion (%) |
|---|---|---|---|
| sKM.593 | ybgC | fadD3 | 0 |
| sKM.594 | ybgC | fadD3, ybgC | 52 |

Example 5

The following Example illustrates conversion of 4-hydroxydecanoic acid to γ-decalactone by *E. coli* strains expressing acyl CoA synthase and homologs of ybgC.

This Example shows the conversion of 4-hydroxydecanoic acid to γ-decalactone by recombinant *E. coli* MG1655 derivative strains expressing acyl-CoA synthetase and YbgC homologs from other microorganisms. The YbgC homologs tested in this experiment and their percent identity to YbgC from *E. coli* are given in Table 2.

Five homologous ybgC genes were synthesized and cloned into a pCL-derivative vector (SC101 replicon, spectinomycin resistance marker) such that they were under the control of the IPTG-inducible Ptrc.

The plasmids were transformed into the base strains sKM.565 (see Table 6) and the resulting strains were then grown as disclosed in Example 1 and 4-hydroxydecanoic acid was added to culture media as disclosed in Example 1. After 20 h, the cultures were extracted as disclosed in Example 1 and the amount of γ-decalactone and the residual amount of 4-hydroxydecanoic acid were determined As can be seen in Table 10, all five tested YbgC homologs converted 4-hydroxydecanoic acid (via 4-hydroxydecanyl-CoA in the presence of FadD3 from *P. putida*) to γ-decalactone. For example, the recombinant *E. coli* strain expressing the YbgC homolog from *Plesiomonas shigelloides*, which is only 62% identical to YbgC from *E. coli*, converted 74% of 4-hydroxydecanoic acid to y-decalactone. Table 2 shows the percent identity and FIG. 9 shows an alignment of these six enzymes of the ybgC protein family.

These results demonstrated that the YbgC family contains enzymes that in the presence of on acyl-CoA synthetase convert 4-hydroxydecanoic acid to γ-decalactone in-vivo, i.e. under physiological conditions without the need to acidify the culture broth.

TABLE 10

Bioconversion of 4-hydroxydecanoic acid to γ-decalactone in recombinant *E. coli.*

| overexpressed Gene | Organism | Conversion % |
|---|---|---|
| ybgC | *Escherichia coli* (SEQ ID NO: 1) | 87% |
| none | — | 0 |
| ybgC | *Citrobacter koseri* (SEQ ID NO: 2) | 93% |
| ybgC | *Enterobacter cloacae*(SEQ ID NO: 3) | 76% |
| Acyl-CoA thioesterase | *Serratia fonticola* (SEQ ID NO: 4) | 72% |
| Acyl-CoA thioesterase | *Exiguobacterium mexicanum* (SEQ ID NO: 5) | 36% |
| ybgC | *Plesiomonas shigelloides* (SEQ ID NO: 6) | 74% |

Example 6

The following Example illustrates conversion of 5-hydroxydecanoic acid to 8-decalactone by *E. coli* strains expressing acyl CoA synthetase and homologs of ybgC.

This Example shows the conversion of 5-hydroxydecanoic acid to δ-decalactone by recombinant *E. coli* MG1655 derivative strains expressing acyl-CoA synthetase and YbgC homologs from other microorganisms. The YbgC homologs tested in this experiment and their percent identity to YbgC from *E. coli* are given in Table 2.

Five homologous ybgC genes were synthesized and cloned into a pCL-derivative vector (SC101 replicon, spectinomycin resistance marker) such that they were under the control of the IPTG-inducible Ptrc.

The plasmids were transformed into the base strain sKM.565 (see Table 6) and the resulting strains were then grown as disclosed in Example 1 and 5-hydroxydecanoic acid was added to culture media as disclosed in Example 1. After 20 h, the cultures were extracted as disclosed in Example 1 and the amount of δ-decalactone and the residual amount of 5-hydroxydecanoic acid were determined As can be seen in Table 11, all five tested YbgC homologs converted 5-hydroxydecanoic acid (via 5-hydroxydecanyl-CoA in the presence of FadD3 from *P. putida*) to δ-decalactone. For Example, the recombinant *E. coli* strain expressing the YbgC homolog from *Plesiomonas shigelloides*, which is only 62% identical to YbgC from *E. coli*, converted 80% of 5-hydroxydecanoic acid to δ-decalactone. Table 2 shows the percent similarity and FIG. 10 shows an alignment of these six enzymes of the ybgC protein family.

These results demonstrated that the YbgC family contains enzymes that in the presence of on acyl-CoA synthetase convert 5-hydroxydecanoic acid to δ-decalactone in-vivo, i.e. under physiological conditions without the need to acidify the culture broth.

TABLE 11

Bioconversion of 5-hydroxydecanoic acid to δ-decalactone in recombinant *E. coli.*

| overexpressed Gene | Organism | Conversion % |
|---|---|---|
| ybgC | *Escherichia coli* | 96% |
| none | — | 2% |
| ybgC | *Citrobacter koseri* | 85% |
| ybgC | *Enterobacter cloacae* | 25% |
| Acyl-CoA thioesterase | *Serratia fonticola* | 34% |
| Acyl-CoA thioesterase | *Exiguobacterium mexicanum* | 36% |
| ybgC | *Plesiomonas shigelloides* | 80% |

Example 7

The following Example illustrates conversion of hydroxyl fatty acid to lactones by *E. coli* strains expressing acyl CoA synthetase and ybgC (D18A) variant.

This Example shows the conversion of 4-hydroxydecanoic acid, 5-hydroxydecanoic acid and 6-hydroxyhexanoic acid to the respective lactones by recombinant *E. coli* MG1655 derivative strains expressing acyl-CoA synthetase and a YbgC variant enzyme with aspartate in position 18 mutated to alanine.

Codon 18 of the *E. coli* ybgC was changed from GAT to GCG using standard molecular biology techniques. The mutated gene, which encodes a mutated ybgC (D18A) protein, was cloned into a pCL-derivative vector (SC101 replicon, spectinomycin resistance marker) such that it was under the control of the IPTG-inducible Ptrc, and the resulting plasmid was transformed into strain sKM.565 (see Table 6)

The resulting strain and the control strain sKM.594 (see Table 6) expressing wildtype YbgC were then grown as disclosed in Example 1 and 4-hydroxydecanoic acid, 5-hydroxydecanoic acid or 6-hydroxyhexanoic acid were added to culture media as disclosed in Example 1. After 20 h, the cultures were extracted as disclosed in Example 1 and the amount of γ- or δ-decalactone or ε-caprolactone and the residual amount of 4- or 5-hydroxydecanoic acid or 6-hydroxyhexanoic acid were determined.

As can be seen in Table 12, the mutated YbgC (D18A) enzyme converted only 30% of 4-hydroxydecanoic acid (via 4-hydroxydecanyl-CoA in the presence of FadD3 from *P. putida*) to γ-decalactone, whereas wildtype YbgC converted 98% 4-hydroxydecanoic acid in this experiment. As can also be seen from Table 12, the mutated YbgC (D18A) enzyme was able only to convert small amounts of 5-hydroxydecanoic acid or 6-hydroxyhexanoic acid to δ-decalactone or ε-caprolactone, whereas wildtype YbgC converted 97% 5-hydroxydecanoic acid or 42% of 6-hydroxyhexanoic acid in this experiment.

These results demonstrated that mutating aspartate 18 to alanine in YbgC from *E. coli* significantly reduced the ability of the enzyme to catalyze the formation of γ- or δ-decalactone or ε-caprolactone from 4-hydroxydecanoic acid or 5-hydroxydecanoic acid or 6-hydroxyhexanoic acid (via 4-hydroxydecanyl-CoA or 5-hydroxydecanyl-CoA or 6-hydroxyhexanyl-CoA in the presence of FadD3 from *P. putida*). It also demonstrates that the surprising lactone-forming activity is intrinsic to the ybgC protein and is not an indirect effect resulting from ybgC overexpression.

TABLE 12

Bioconversion to γ- or δ-decalactone or s-caprolactone in recombinant *E. coli.*

| overexpressed Gene | 4-OH decanoic acid Conversion % | 5-OH decanoic acid Conversion % | 6-OH hexanoic acid Conversion % |
|---|---|---|---|
| ybgC | 98% | 97% | 42% |
| none | 0 | 0 | 0 |
| ybgC(D18A) | 30% | 2% | 6% |

As is apparent to one of skill in the art, various modifications and variations of the above aspects and embodiments can be made without departing from the spirit and scope of this disclosure. Such modifications and variations are thus within the scope of this disclosure.

Sequence Appendix

SEQ ID NO: 1: *Escherichia coli* ybgC (UniProt Accession POA8Z3):
MNTTLFRWPVRVYYEDTDAGGVVYHASYVAFYERARTEMLRHHHFSQQA
LMAERVAFVVRKMTVEYYAPARLDDMLEIQTEITSMRGTSLVFTQRIVNAE
NTLLNEAEVLVVCVDPLKMKPRALPKSIVAEFKQ SEQ ID NO: 2: *Citrobacter koseri* ybgC (UniProt Accession A0A078LJN7):
MNIFRWPVRVYYEDTDAGGVVYHASYVAFYERARTEMLRHHHFSQQVLL
AERVAFVVRKMTLEYYAPARLDDMLEVQTEITSMRGTSLVFTQRIVNAENN
VLNEAEVLIV CVDPLKMKPR ALPKSIVAEF KQ SEQ ID NO: 3: *Enterobacter cloacae* ybgC (UniProt Accession A0A157YV01):
MNTTLFRWPVRVYYEDTDAGGVVYHASYVAFYERARTEMLRHHHFSQQVL
LAERVAFVVRKMTLEYFAPARLDDMLEIQTEITSMRGTSLVFTQRIVNAENT
VLNEAEVLIVCVDPLLMK PRALPKSIVAEFKQ SEQ ID NO: 4: *Serratia fonticola* ybgC (UniProt Accession A0A0F7D2B7):
MSNKLFRWPVRVYFEDTDAGGVVYHARYVAFYERARTEMLRQHNFHQQQ
LLSEEHVAFAVRRMTVDYLSPARLDDLLEVQSKITSIRGASLTFAQRIVNSD
GTLLSQADVLIACIDPHQMKPIALPKSIVAEFKQ -continued Sequence Appendix SEQ ID NO: 5: *Exiguobacterium mexicanum* ybgC (UniProt Accession A0A099DCT9):
MLFRWPVRVY YEDTDAGGVV YHARYLAFFE
RARTEMLRNKGINQQSMLAD
NLGFVVRSMTIDFVKGAKLDDLLEVETQIVEMKRASLTFHQRLVDSQGNLL
CGANALIACVDTSKMKPIA LPKS SEQ ID NO: 6: *Plesiomonas shigelloides* ybgC (UniProt Accession A0A1A9AWY4):
MSSKVSQWPVRVYYEDTDAGGVVYHARYVAFFERARTEMLRSLGQQQQT
LLQHNVAFVVRRMTVDYRSPARLDDLLSVETEISSFRGASVTFNQRIIHQDG
RVLCTAEVLVACIDLAKMK PVALPAELVA EFTCVC SEQ IN NO: 7: *Escherichia coli* fadD (UniProt Accession P69451):
MKKVWLNRYPADVPTEINPDRYQSLVDMFEQSVARYADQPAFVNMGEVM
TFRKLEERSRAFAAYLQQGLGLKKGDRVALMMPNLLQYPVALFGILRAGMI
VVNVNPLYTPRELEHQLNDSGASAIVIVSNFAHTLEKVVDKTAVQHVILTR
MGDQLSTAKGTVVNFVVKYIKRLVPKYHLPDAISFRSALHNGYRMQYVKP
ELVPEDLAFLQYTGGTTGVAKGAMLTHRNMLANLEQVNATYGPLLHPGKE
LVVTALPLYHIFALTINCLLFIELGGQNLLITNPRDIPGLVKELAKYPFTAITG
VNTLFNALLNNEFQQLDFSSLHLSAGGGMPVQQVVAERWVKLTGQYLLEG
YGLTECAPLVSVNP
YDIDYHSGSIGLPVPSTEAKLVDDDDNEVPPGQPGELCVKGPQVMLGYWQR
PDATDEIIKNGWLHTGDIAVMDEEGFLRIVDRKKDMILVSGFNVYPNEIEDV
VMQHPGVQEVAAVGVPSGSSGEAVKIFVVKKDPSLTEESLVTFCRRQLTGY
KVPKLVEFRDELPKSNVGKILRRELRDEARGKVDNKA SEQ IN NO: 8: *Pseudomonas putida* fadD-I (UniProt Accession Q88EB7):
MIENFWKDKYPAGITAEINPDEFPNIQAVLKQSCQRFADKPAFSNLGKTITY
GELYALSGAFAAWLQQHTDLKPGDRIAVQLPNVLQYPVAVFGAMRAGLIV
VNTNPLYTAREMEHQFNDSGAKALVCLANMAHLAEKVVPKTQVRHVIVTE
VADLLPPLKRLLINSVIKYVKKMVPAYNLPQAVRENDALALGKGQPVTEAN
PQANDVAVLQYTGGTTGVAKGAMLTHRNLVANMLQCRALMGSNLHEGCE
ILITPLPLYHIYAFTFHCMAMMLIGNHNVLISNPRDLPAMVKELGKWKFSGF
VGLNTLFVALCNNEAFRALDFSALKITLSGGMALQLSVAERWKAVTGCAIC
EGYGMTETSPVAAVNPSEANQVGTIGIPVPSTLCKVIDDAGNELPLGEVGEL
CVKGPQVMKGYWQREDATAEILDSEGWLKTGDIAVIQADGYMRIVDRKKD
MILVSGFNVYPNELEDVLAALPGVLQCAAIGVPDEKSGEVIKVFIVVKPGMT
VTKEQVMEHMRANVTGYKVPRHIEFRDSLPTTNVGKILRRELRDEELKKQG
LKKIA SEQ IN NO: 9: *Pseudomonas putida* fadD-II (UniProt Accession Q88EB6):
MQADFWNDKRPAGVPSTIDINAYASVVEVFERSCKRFADRPAFSNLGVTLS
YAELERHSAAFAAWLQQHTDLKPGERIAVQMPNVLQYPIAVFGAMRAGLI
VVNTNPLYTEREMRHQFKDSGARALVYLNMFGKRVQEVLPDTGIEYLIEAK
MGDLLPAAKGWLVNTVVDKLKKMVPAYRLPQAVPFKQVLREGRGLSPKP
VSLNLDDIAVLQYTGGTTGLAKGAMLTHGNLVANMLQVLACFSQHGPDGQ
KLLKDGQEVMIAPLPLYHIYAFTANCMCMMVTGNHNVLITNPRDIPGFIKEL
GKWRFSALLGLNTLFVALMDHPGFRQLDFSALKVINSGGTALVKATAERW
EDLTGCRIVEGYGLTETSPVASTNPYGQLARLGTVGIPVAGTAFKVIDDDGN
ELPLGERGELCIKGPQVMKGYWQQPEATAQALDAEGWFKTGDIAVIDPDGF
TRIVDRKKDMIIVSGFNVYPNEIEDVVMGHPKVANCAAIGVPDERSGEAVK
LFVVPREGGLSVDELKAYCKANFTGYKVPKHIVLRESLPMTPVGKILRRELR
DIA SEQ IN NO: 10: *Pseudomonas putida* PP_0763 "fadD3" (UniProt Accession Q88PT5):
MLQTRIIKPAEGAYAYPLLIKRLLMSGSRYEKTREIVYRDQMRLTYPQLN
ERIARLANVLTEAGVKAGDTVAVMDWDSHRYLECMFAIPMIGAVVHTINV
RLSPEQILYTMNHAEDRVVLVNSDFVGLYQAIAGQLTTVDKTLLLTDGPD
KTAELPGLVGEYEQLLAAASPRYDFPDFDENSVATTFYTTGTTGNPKGVY
FSHRQLVLHTLAEASVTGSIDSVRLLGSNDVYMPITPMFHVHAWGIPYAA
TMLGMKQVYPGRYEPDMLVKLWREEKVTFSHCVPTILQMLLNCPNAQGQ
D
FGGWKIIIGGSSLNRSLYQAALARGIQLTAAYGMSETCPLISAAHLNDEL
QAGSEDERVTYRIKAGVPVPLVEAAIVDGEGNFLPADGETQGELVLRAPW
LTMGYFKEPEKSEELWQGGWLHTGDVATLDGMGYIDIRDRIKDVIKTGGE
WVSSLDLEDLISRHPAVREVAVVGVADPQWGERPFALLVARDGHDIDAKA
LKEHLKPFVEQGHINKWAIPSQIALVTEIPKTSVGKLDKKRIRQDIVQWQ
ASNSAFLSTL SEQ IN NO: 11: *Pseudomonas aeruginosa* acyl-CoA synthase (UniProtKB - Q9HX89):
MLKTRLIPAAAGAYQYPLLIKSLMLSGRRYEKSHEIVYRDQVRYSYATEN
ERVARLANVLSEAGVKAGDTVAVMDWDSHRYLECMFAIPMIGAVLHTINI
RLSPEQILYTMNHAEDRFVLVNSEFVPLYQAVAGQLATVERTILLTDGAE
KSAELPGLVGEYESLLAAASPRYDFPDFDENSIATTFYTTGTTGNPKGVY
FSHRQLVLHTLAMASTIGSLDSIRLLGTSDVYMPITPMFHVHAWGTPYVA -continued

| Sequence Appendix |
| --- |

TMLGVKQVYPGRYDPELLVELWKREKVTFSHCVPTILQMVMNARAAQGVD
FKGWKVIIGGSALNRSLYEAAKARGIQLTAAYGMSETCPLISCAYLNDEL
LAGSEDERTTYRIKAGVPVPLVDAAIMDEQGRFLPADGESQGELVLRSPW
LTQGYFREPERGEELWRGGWMHTGDVATLDGMGFIEIRDRIKDVIKTGGE
WLSSLELEDLISRHPAVREVAVVGVPDPQWGERPFALLVVREGQQLDARG
LKEHLKPFVEQGNINKWAIPSQIAVVTDIPKTSVGKLDKKRIRIEIAQWQ
EAGSAFLSTV

SEQ IN NO: 12: *Pseudomonas citronellolis* LMG 18378 fatty-acyl-CoA synthase (UniProt Accession A0A1I1GPT1)
MLKTRLLPAASNAYQYPLLIKSLLLSGARYEKSREIVYRDLVRYNYATFN
ERVARLANVLTEAGVQAGDTVAVMDWDSHRYLEAMF AIPMIGAVLHTINI
RLSPDQILYTMNHAEDRFVLVNAEFVPLYQGIAGQLTTVQKTLLLSDGAD
KSCALDDCIGEYETLMAAASPRYAFPDFDENSVATTFYTTGTTGNPKGVY
FTHRQLVLHTLAMASTIASLDSIRLMGNSDVYMPITPMFHVHAWGVPYVA
TMLGIKQVYPGRYDPELLVDLWKRENVTFSHCVPTILQMVMNAKAAQGVD
FKDWKIIGGSALNRSLYEAAQARGIQLTAAYGMSETCPLISCAYLNDEL
LAGSEDERTTYRIKAGVPVPLVDAAIMDEHGQLLPADGESQGELVLRSPW
LTQGYFREPQKGEELWAGGWMHTGDVATLDGMGFIDIRDRIKDVIKTGGE
WLSSLELEDLISRHPAVREVAVVGVPDPQWGERPFALLVLFEGQQLDAKG
LKEHLKPFVEQGHINKWAIPSQIAVVTEVPKTSVGKLDKKRIRVDIARWQ
ESGSEFLSAL SEQ IN NO: 13: *Pseudomonas mendocina* fatty acid-CoA ligase (UniProt Accession A4XYJ3):
MLQTRLIPPANNAHAYPLLIKRLLLSGSRYEKTREIVYRDKLRYSYATFT
ERVARLANVLSQAGVKAGDTVAVMDWDSHRYLECMFAIPMLGAVLHTINI
RLSPDQILYTMNHAEDRFVLVNSEFVPLYNGIAGQLTTVEKTLLLTDGED
KNADLPNLVGEYESLLAAASPHYDFADFDENSVATTFYTTGTTGNPKGVY
FTHRQLVLHTMSMATTMGGLDSIRLMGNDDVYMPITPMFHVHAWGVPYVA
TMLGVKQVYPGRYEPDMLCRLIKEEKVTFSHCVPTILQMLLSAPGAQGHD
FGGMKMIIGGSALNRSLYEAAKERGIQLTAAYGMSETCPLISCAYLNEEL
RAGSEDERTTYRIKAGIPVPLVEAAIMDADGKLLPSDGESQGELVLRAPW
LTQGYFREPEKGEELWAHGWLHTGDVATIDGMGFIEIRDRIKDVIKTGGE
WISSLELEDLISRHSAVREVAVVGVPDPQWGERPFALVVLRDAQGLDAKG
LKEHLKPFVEQGHINKWAIPTQIALVTEIPKTSVGKLDKKRIRVEIAQWQ
EAGSTFLSTL SEQ IN NO: 14: *Bacillus subtilis* IcfB (UniProt Accession 007610):
MNLVSKLEETASEKPDSIACRFKDHMMTYQELNEYIQRFADGLQEAGMEK
GDHLALLLGNSPDFIIAFFGALKAGIVVVPINPLYTPTEIGYMLTNGDVKAIV
GVSQLLPLYESMHESLPKVELVILCQTGEAEPEAADPEVRMKMTTFAKILRP
TSAAKQNQEPVPDDTAVILYTSGTTGKPKGAMLTHQNLYSNANDVAGYLG
MDERDNVVCALPMFHVFCLTVCMNAPLMSGATVLIEPQFSPASVFKLVKQ
QQATIFAGVPTMYNYLFQHENGKKDDFSSIRLCISGGASMPVALLTAFEEKF
GVTILEGYGLSEASPVTCFNPFDRGRKPGSIGTSILHVENKVVDPLGRELPAH
QVGELIVKGPNVMKGYYKMPMETEHALKDGWLYTGDLARRDEDGYFYIV
DRKKDMIIVGGYNVYPREVEEVLYSHPDVKEAVVIGVPDPQSGEAVKGYV
VPKRSGVTEEDIMQHCEHLAKYKRPAAITFLDDIPKNATGKMLRRALRDILP
Q SEQ IN NO: 15: *Saccharomyces cerevisiae* FAA1 (UniProt Accession P30624):
MVAQYTVPVGKAANEHETAPRRNYQCREKPLVRPPNTKCSTVYEFVLECF
QKNKNSNAMGWRDVKEIHEESKSVMKKVDGKETSVEKKWMYYELSHYH
YNSFDQLTDIMHEIGRGLVKIGLKPNDDDKLHLYAATSHKWMKMFLGAQS
QGIPVVTAYDTLGEKGLIHSLVQTGSKAIFTDNSLLPSLIKPVQAAQDVKYII
HFDSISSEDRRQSGKIYQSAHDAINRIKEVRPDIKTFSFDDILKLGKESCNEID
VHPPGKDDLCCIMYTSGSTGEPKGVVLKHSNVVAGVGGASLNVLKFVGNT
DRVICFLPLAHIFELVFELLSFYWGACIGYATVKTLTSSSVRNCQGDLQEFKP
TIMVGVAAVWETVRKGILNQIDNLPFLTKKIFWTAYNTKLNMQRLHIPGGG
ALGNLVFKKIRTATGGQLRYLLNGGSPISRDAQEFITNLICPMLIGYGLTETC
ASTTILDPANFELGVAGDLTGCVTVKLVDVEELGYFAKNNQGEVWITGANV
TPEYYKNEEETSQALTSDGWFKTGDIGEWEANGHLKIIDRKKNLVKTMNGE
YIALEKLESVYRSNEYVANICVYADQSKTKPVGIIVPNHAPLTKLAKKLGIM
EQKDSSINIENYLEDAKLIKAVYSDLLKTGKDQGLVGIELLAGIVFFDGEWTP
QNGFVTSAQKLKRKDILNAVKDKVDAVYSSS SEQ IN NO: 16: *Umbellularia california* FatB1 (UniProt Accession Q42561)
MLKLSCNVTDSKLQRSLLFFSHSYRSDPVNFIRRRIVSCSQTKKTGLVPLRAV
VSADQGSVVQGLATLADQLRLGSLTEDGLSYKEKFVVRSYEVGSNKTATVE
TIANLLQEVGCNHAQSVGFSTDGFATTTTMRKLHLIWVTARMHIEIYKYPA
WGDVVEIETWCQSEGRIGTRRDWILKDSVTGEVTGRATSKWVMMNQDTR
RLQKVSDDVRDEYLVFCPQEPRLAFPEENNRSLKKIPKLEDPAQYSMIGLKP
RRADLDMNQHVNNVTYIGWVLESIPQEIVDTHELQVITLDYRRECQQDDVV
DSLTTTTSEIGGTNGSATSGTQGHNDSQFLHLLRLSGDGQEINRGTTLWRKK
PSS -continued

| Sequence Appendix |
|---|

SEQ IN NO: 17: *Cinnamomum camphorum* FatB1 (UniProt Accession Q39473)
MATTSLASAFCSMKAVMLARDGRGMKPRSSDLQLRAGNAQTSLKMINGTK
FSYTESLKKLPDWSMLFAVITTIFSAAEKQWTNLEWKPKPNPPQLLDDHFGP
HGLVFRRTFAIRSYEVGPDRSTSIVAVMNHLQEAALNHAKSVGILGDGFGTT
LEMSKRDLIWVVKRTHVAVERYPAWGDTVEVECWVGASGNNGRRHDFLV
RDCKTGEILTRCTSLSVMMNTRTRRLSKIPEEVRGEIGPAFIDNVAVKDEEIK
KPQKLNDSTADYIQGGLTPRWNDLDINQHVNNIKYVDWILETVPDSIFESHH
ISSFTIEYRRECTMDSVLQSLTTVSGGSSEAGLVCEHLLQLEGGSEVLRAKT
EWRPKLTDSF RGISVIPAES SV SEQ IN NO: 18: *Ricinus communis* FatB1 (UniProt Accession
NP_001310677)
MVATAAAATSSFFPVPSQSADANFDKAPASLGGIKLKSTSCSRGLQVKANA
QAPPKINGSSVGFTTSVETVKNDGDMPLPPPPRTFINQLPDWSMLLAAITTIF
LAAEKQWMMLDWKPRRPDMLIDPFGIGRIVQDGLIFRQNFSIRSYEIGADRT
ASIETLMNHLQETALNHVKTAGLLGDGFGSTPEMSKRNLIWVVTRMQVLV
DRYPTWGDVVQVDTWVSKSGKNGMRRDWCVRDSRTGETLTRASSVWVM
MNKLTRRLSKIPEEVRGEIEPYFLNSDPIVDEDSRKLPKLDDSNADYVRKGL
TPRWSDLDINQHVNNVKYIGWILESAPLPILESHELSAITLEYRRECGRDSVL
QSLTAVSGNGIGNLGNAGDIECQHLLRLEDGAEIVRGRTEWRPKYSSNFGI
MGQIPVESA SEQ IN NO: 19: *Cuphea hookeriana* FatB2 (UniProt Accession Q39514)
MVAAAASSAFFPVPAPGASPKPGKFGNWPSSLSPSFKPKSIPNGGFQVKAND
SAHPKANGSAVSLKSGSLNTQEDTSSSPPPRTFLHQLPDWSRLLTAITTVFVK
SKRPDMHDRKSKRPDMLVDSFGLESTVQDGLVFRQSFSIRSYEIGTDRTASIE
TLMNHLQETSLNHCKSTGILLDGFGRTLEMCKRDLIWVVIKMQIKVNRYPA
WGDTVEINTRFSRLGKIGMGRDWLISDCNTGEILVRATSAYAMMNQKTRRL
SKLPYEVHQEIVPLFVDSPVIEDSDLKVHKFKVKTGDSIQKGLTPGWNDLDV
NQHVSNVKYIGWILESMPTEVLETQELCSLALEYRRECGRDSVLESVTAMD
PSKVGVRSQYQHLLRLEDGTAIVNGATEWRPKNAGANGAISTGKTSNGNSV
S SEQ IN NO: 20: *Cuphea palustris* FatB2 (UniProt Accession Q39555)
MVAAAASAAFFSVATPRTNISPSSLSVPFKPKSNHNGGFQVKANASAHPK
ANGSAVSLKSGSLETQEDKTSSSSPPPRTFINQLPVWSMLLSAVTTVFGV
AEKQWPMLDRKSKRPDMLVEPLGVDRIVYDGVSFRQSFSIRSYEIGADRT
ASIETLMNMFQETSLNHCKIIGLLNDGFGRTPEMCKRDLIWVVTKMQIEV
NRYPTWGDTIEVNTWVSASGKHGMGRDWLISDCHTGEILIRATSVWAMMN
QKTRRLSKIPYEVRQEIEPQFVDSAPVIVDDRKFHKLDLKTGDSICNGLT
PRWTDLDVNQHVNNVKYIGWILQSVPTEVFETQELCGLTLEYRRECGRDS
VLESVTAMDPSKEGDRSLYQHLLRLEDGADIVKGRTEWRPKNAGAKGAIL
TGKTSNGNSIS SEQ IN NO: 21: *Cuphea lanceolata* FatB3 (Accession CAB60830; UniProtKB -
Q9SMI9)
MVAAAATSAF FPVPAPGTSP KPGKSGNWPS SLSPTFKPKS IPNAGFQVKA
NASAHPKANG SAVNLKSGSL NTQEDTSSSP PPRAFLNQLP DWSMLLTAIT
TVFVAAEKQW TMLDRKSKRP DMLVDSVGLK SIVRDGLVSR QSFLIRSYEI
GADRTASIET LMNHLQETSI NHCKSLGLLN DGFGRTPGMC KNDLIWVLTK
MQIMVNRYPT WGDTVEINTW FSQSGKIGMA SDWLISDCNT GEILIRATSV
WAMMNQKTRR FSRLPYEVRQ ELTPHFVDSP HVIEDNDQKL
HKFDVKTGDS
IRKGLTPRWN DLDVNQHVSNVKYIGWILES MPIEVLETQE LCSLTVEYRR
ECGMDSVLESVTAVDPSENG GRSQYKHLLR LEDGTDIVKS
RTEWRPKNAG
TNGAISTSTA KTSNGNSAS SEQ IN NO: 22: *Arabidopsis thaliana* FatA (NCBI Protien ID NP_189147
or UniProtKB - Q42561)
MLKLSCNVTDSKLQRSLLFFSHSYRSDPVNFIRRRIVSCSQTKKTGLVPLRAV
VSADQGSVVQGLATLADQLRLGSLTEDGLSYKEKFVVRSYEVGSNKTATVE
TIANLLQEVGCNHAQSVGFSTDGFATTTTMRKLHLIWVTARMHIEIYKYPA
WGDVVEIETWCQSEGRIGTRRDWILKDSVTGEVTGRATSKWVMMNQDTR
RLQKVSDDVRDEYLVFCPQEPRLAFPEENNRSLKKIPKLEDPAQYSMIGLKP
RRADLDMNQHVNNVTYIGWVLESIPQEIVDTHELQVITLDYRRECQQDDVV
DSLTTTTSEIGGINGSATSGTQG
HNDSQFLHLLRLSGDGQEINRGTTLWRKKPSS SEQ IN NO: 23: *Helianthus annuus* FatA (NCBI Protien ID
XP_021976166)
MLSRGVPTATATAYNDVIKETARSVTNSRSIDSVSIRRRNNGFVSNSLCRRV
APVMAVKVDEQRTGVAVDVTEKRLADRLRMGSLTEDGLSYKERFIIRCYEV
GINKTATVETIANLLQEVGGNHAQSVGFSTDGFATTTTMRKLNLIWVTSRM -continued

| Sequence Appendix |
| --- |

HIEIYRYPAWSDVVEIETWCQGEGRIGTRRDWIIKDHANGEVIGRATSKWV
MMNSETRRLQKVNDDIRDEYLIFCPKTLRLAFPEENNNSLKKIAKLEDPAEC
STLGLVPRRADLDMNKHVNNVTYIGWVLESIPQEVIDTHELQTITLDYRREC
QHDDVVDSLTSSESPAVNGCASGENLSKFLHLLRSSGEGLELNRGRTEWRK
KPAKK

SEQ IN NO: 24: *Macadamia tetraphylla* FatA1 (NCBI Protien ID ACB29661)
MLSVKGCNAPDQLRSLTQCLSVTPPKALTRRGIAVVSCCSSSSTSPSSISASR
VSNLVVSERINGSGGVVSNPSSNGSASLLEELRLGSLAEDGLSYKEKFIVRS
YEVGINKTATMEAIANLLQEAACNQVQTLGYSTDGMGTSYTMRQLHLIWV
TARMHIEVYKYPAWGDMIEIETWFEAGRVGTRRDFVVKDATGTVIGRATSK
WVAMNQDTRRLQKVNDKILEEIMSHAPRTPRLAFPEEDNCSLKKIPKLEEPA
QYSKLGLKARRADLDMNQHVNNVTYIGWLLESLPQEIIDTHELRKVTLDYR
RECQHDDTVDSLTSMELMDNAEAIPELNGINGSATERKHEEDCCRFLHFVR
FSGDGPEVNRGRTEWRRKSTR SEQ ID NO: 25: *Aspergillus terreus* XP_001210151
MIKETEQIPGPRPLPVVGNLFDMDLEHGLECLIRLADDFGPLFQITINGEKQIF
ATSQALVDELCDESRFHKAVMGGLEKLRMLASDGLFTAYHGERGWGIAHR
ILVP AFGPLRIRNMFEEMNDVAQQLCLKWARQGSSTSINITDDFTRLTLDTIA
LCTMNFRLNSFYNNETMHPFVKSMLYVLRESDIQSMLPGIANCIRVKARSR
MSKHIQLMRNMARGIIQERRDQAEPVDDLLNTLLNGRDPVTGEGMSDDLII
NNVITFLIAGHETTSGLLSFTFYYLLQNPHILERAQNEVDEVTGGERITVQHL
GRLTYIDAILKESLRLMPTAPAFTVTPKKPEVLGGAWAIDAGQAVNVLLPVC
LRDRSVFGPDADEFRPERMLEENFSKLPPNSWKPFGNGERSCIGRAFAWQE
AQLVVAMVLQTFDLVPDDPSYKLRIKETLTIKPDGFRVRATLRRGQSATGLS
QGSMSASGATSSVASPGPPAATGAQSNPAGGQRISFFYGSNSGTCKALAHRL
ASSLMGRGFTEQKLAALDTVVGNLPTDQPVIIVTTSYDGRPTDDAEEFVRW
LESKRPVLQGVSYAVFGCGHHDWAKTFYRIPILIDDLMHKAGATRLTALGT
ANAAVSDLFSDLELWEETNLLPALREAFPPSNSSDVESSEPHQLQICVSKPRR
VDMHRGLVEAKVTAVRTLTSPDSPEKRHVEFHVQGDTTWRPGDHVNILPV
NPLSTVSRVLAYFQLAPDHSITVNSFNTQGLPSATPVSATELFSSFVELSQPAT
RKNLKALAMAAESKTDEQELIRLHDSYDALVRDKRVSVLDILERFPSISLPIG
IFISMLPPLRLRTYSLSMAPSFKPSHGSLTFSVINEPAWSGNGQYLGVGSNYL
ASLTPGSLLYLSPRPAKDAFHLPADQFNTPIIMICAGSGLAPFMGFIQERMTW
LKQGRPLAKGLLFFGCRGPHLDDLYYEELSEFEDAGVVEVHRAYSRAPDDV
RAKGCRHVQHRLVTEAEAVRDHWGRNAIVYVCGSSNMARGVQTVLEEILG
TLPPERYVAEIF SEQ ID NO: 26 *Aspergillus kawachii* GAA88365
MKDAERIPGPKPLPVVGNLFDIDPEHSLESIVAFAEKFGPLFQITINGEKQIFA
TSQALVDELCDELRFHKAVVTGLEILRLLAHDGLFTAYHGERGWGIAHRIL
VPAFGPLRIRNMLDDMSDVAQQLCLKWARQGGSTSINITEDFTRLTLDTIAL
CTMGFRLNSFYNNETMHPFVQSMLYVLREADIQANLPGIANSIRVSAQRRM
HKNIEAMRTMARGIIQERRKNKNPVDDILNTLLNGRDPVTGEGMSDDSIIDN
VITFLIAGHETTSGLLSFTFYFLIQHPHILKKAQEEVDETVGLAQISAQHLAEL
PYIDAILKESLRLMPTAPGFTVTPKKTEVLGGRWMINAGQPVNVLLPACLRD
QSVFGPDADEFRPERMLAENFSKLPPNSWKPFGNGERGCIGRAFAWQEAQL
VVAMILQTFDLVPDDPSYQLRIKETLTIKPDGFRIRATLRRGQTATGLSRRSM
LVARDGSSEESSNHPAEARGDHAPARGQPVSFFYGSNSGTCKALAHQLASN
MMSRGYTTQKLAPLDNAVDNLPRDQPVIILTTTYDGQPTDNAKKFVAWLE
TGNVLSLQGISYAVFGCGHHDWTQTFYRIPILIDDLMYKAGATRLAPRGAA
NAAVSDLFSDLEAWEETSLLPALRENFLPSNSTDFDPLNPHQIQLSLSKPRRV
DLHKGLIEAKVTAVRVLTSPDTPEKRHLEFCFQGDLSLRPGDHLNILPVNPPS
TVSRVLAQFNLAPDYNITVNSFNTLGLPQATPVSASELFSSYVELCQPATRN
NLKSLIAATQSDTVKQELNRLYDSYEFIVRDKRVSVLDLLEQFPSISLPIAAFI
SMLPALRVRTYSLSMAPAFKPSHSSLTFSVINEPAWRGSGQHLGVASNYLAS
LTSGSIFYFSPRPAKETFHLPKDPSRTPIIMICAGSGLAPFLSFIQDRMVLKQQ
NKPLAKAFLFFGCRGRSLDDLYHEELSEYEAAGVVEVRRAYSKTPEFDIAK
GCRYVQHRLVTEGQAILSLWAQNAIIYVCGSTSMAKGAEAVLQNMLGPLP
KERYVTEIF SEQ ID NO: 27 *Aspergillus niger* CAK39220
MSMLLGVRGTRDQSSYIGGRDYVFWQKEMRDAERIPGPTPLPVVGNLFDID
LEHVLQSVIGLANKYGPLFQITINGEKQIFATSQALVDELCDESRFHKAVASG
LENLRMLAHDGLFTAYHGERGWGIAHRILVPAFGPLRIQSMFDDMGDLAQ
QLCLKWARQGASNSINITDDFTRLTLDTIALCTMDFRLNSFYNNDTMHPFVE
SMLYVLREADVQSALPGIANSVRIMAHRRMLKNIEAMRTIARDIIHDRRKKE
NPADDLLNTLLNGRDPVTGEGMSDESIIDNVITFLVAGHETTSGLLSFTFYYL
VQHPDILKKAQKEVDETVGQAQISVQHLAELPYIDAILKESLRMMPTAPGFT
VTPKKAETLGGKWLLNAGQPINVLLPACLRDRSIFGPNADEFSPGRMLAENF
SKLPPNSWKPFGNGERSCIGRAFAWQEAQLVVAMILQNFDLVPDDPSYTLRI
KETLTIKPDGFRVRATLRHRQTATGLFQHTLSARNDTSLASSSAHFIKKSEDQ
APAGGRPICFFYGSNSGTCKALAHRLASDLMPYGFTDQKLAVLDTAVDNLP
RDQPVIILTTTYDGQPTDDAKKFVAWLESGKVPALQGISYAVFGCGHHDWT
QTFYRIPTLIDELMHKAGATRLAPRGTANAAVSDLFSDLEAWEETSLLPALR
ETFLLSSSSDLEPLNLHQLQISLSKPRRIDLHKDLMEARVTTVRILTNPDTPEK -continued

| Sequence Appendix |
| --- |

RHIEFRFQGDTTLRPGDHVNVLPVNPPSTVLRVLAQFNLAPDYSITINSENTL
GLPQATPVSASELFSAYVELSQPATRNNLRILAATAQSDEDKQELIHLQDSY
DSLVRDKRVSVLDLLEQFPSVSLPIAAFISMLPALRLRTYSLSLAPSFKPSHGS
LTFSVVNEPARNGNRRYLGVGSNYLASLTPGSILYLSPRPAKEAFHLPVDQS
RIPIIMICAGSGLAPFLSFIQDRMIWQQQDKPLARALLFFGCGGRFLDDLYHE
ELSEFEAAGVVDVRRAYSKVLDYDMARGCKYVQDRLVAEANAIRHLWAQ
DATIYVCGSADMAKGVEGVLEKLLGMLPRERYVTEIYQMQTRDNVSEWLI

SEQ ID NO: 28 *Penicillium expansum* XP_016592781
mkdmesipgp kplpvvgnlf didlenglqs iikmahefgp lfqitingqk qifatsqalv
delcdetrfh kavmggiqkl rmlakdglft ayhgergwgi ahrilmpafg plrirdmfed
msdvaqqlcf kwarqgssts inicddftrl tldtialctm gfrlnsyyns nalhpfiesm
lyvlkeaelq stlpgvancm rvkaqrrmsk hidamrsmar nlieerrakp epvddllntl
lngrdpitge gmsddliisn iitfliaghe ttsgllsftf yyllqnqdvl erarnevdev
tgvgpitvqh laklpyidai mkeslrlmpt apaftvtpqk pevlggkwmi ntgdsvnlll
pvclrdetvf gpdagefrpn rmleenfskl ppnswkpfgn gergcigraf awqeaqlvva
lvlrtfdlaa edpyyklrik etltikpdgf riratlrhgk satalsqhni svgaaaspas
stylagneng rdaaggqpvs ffygsnsgtc kalthrlast mmtrgftdqn iapldsavdn
lprdqptiii tttydgqptd dakkfvawle sgnspslqgv syavfgcghq dwtktfyrip
ilidnlmyka gatrlatrga anaaisdlfs dlevweetnl lpglresfyp pnnsnfvple
phqlqisink ptrvgmhrdl ieakvtairt ltspgapekr hlefcipget tlrpgdhlni
lpvnppstvs ralarfnlap dhsitfessn aldlpqatpv saaelfssyl elsqpatrnn
lkelasttps dgekqellhl ydsydslira krasvldlle qftsvtlpit tfismlpalr
vrtyslsmap sfkplhyslt fsvinepawn gngrylgvas nylaslnlgs ilyisprpak
dafhlptdqs skpiimicag sglapfrsfi qdrmlwqqqd ktlakallff gcrspqlddl
yhdelsqfea agvvevrray skvpnhylak gcryvqhrll tetetiqdmw aqdaiiyvcg
sgnlakgvka vlesmlgtly eryiteif SEQ ID NO: 29 *Aspergillus niger* GAQ43769
mkdaeripgp kplpvvgnll didpehglqs iiafadkygp lfqitingek qifatsqalv
delcdesrfh kavvtglevl rllahdglft ayhgergwgi ahrilvpafg plrirnmldd
msdvaqqlcl kwarqggsts initedftrl tldtialctm gfrlnsfynn etmhpfvqsm
lyvlkeadvq anlpgiansi rvsaqrrmhk nieamrtmar giiqerrknk npvddilntl
lngrdpvtge gmsddsiidn vitfliaghe ttsgllsftf yfliqhphil kkaqeevdet
vglaqisaqh laelpyidai lkeslrlmpt apgfavtpkk tevlggkwmi nagqpvnvll
paclrdqsvf gpdadefhpe rmlaenfskl ppnswkpfgn gergcigraf awqeaqlvva
milqtfdlvp ddpsyqlrik etltikpdgf rirallrrgq tatglsrrsm lvardgssge
ssnhlaearg dhapargqpv sffygsnsgt ckalahqlas nmmsrgyttq klapldnavg
nlprdqpvii ltttydgqpt ddakkfvawl etgnvpslqg isyavfgcgh hdwtqtfyri
piliddlmhk agatrlaprg aanaavsdlf sdleaweets llpalrenfl psnstdfdpl
nphqiqlsls kprrvdlhkg lieakvtavr vltspdtpek rhlefcfqgd tslrpgdhln
ilpvnppstv srvlaqfnla pdynitvnsf ntlglpqatp vsaselfssy velcqpatrn
nlkaliaatq sdpdkqelnr lydsyefivr dkrvsvldll eqfpsislpi aafismlpal
rvrtyslsma psfkpshssl tfsvinepaw rgsgqhlgva snylasltsg sifyfsprpa
kesfhlpkdp sntpiimica gsglapflsf iqdrmvlkqq ykplakaflf fgcrgrsldd
lyheelsefe aagvveirra ysktpdfdia kgcryvqhrl vtegqailsl wsqnatiyvc
gstnmakgve avlqnmlgpl pkeryvteif SEQ ID NO: 30 *Penicillium camemberti* CRL20473
mkdmdcipgp kplpvvgnlf dldldnalqs iirmadefgp lfqitingqk qifatsqalv
delcdetrfh kavmggvekl rmlaqdglft ahhgergwgi ahrilmpafg plrirdmfed
msdvahqlcf kwarqgssas iniaedftrl tldtialctm sfrlnsyyns etmhpfvqsm
lyvlkeadlq atlpgvancv rvkaqrrmsk hiqamrniag diikgrrdkp epvddllntl
lngrdpvtge gmsdeliisn iitflvaghe ttsgllsftf yyllqhphvl eqarnevdev
vgvgpitvqh laklpyidav mkeslrlmpt apaftvtpkk pevvggkwmv ntgqsvhvll
pvclrdeavf gpdagefrpt rmleenfskl ppnswkpfgn gergcigraf awqeaqlvva
svlqtfdlva edpyyklrik etltikpdgf rvratlrrgq satalsqhnm sagataspgs
sthlagdeng qdtaggqpis ffygsnsgtc kalahrlast mmtrgftdqh laqldsavdn
lprdqptiiv tttydgqptd dakkflawle sgnvpslhgv syavfgcghq dwtktfyrip
iliddlmhka gatrlttrgt anaavsdlfs dlevweetnl lpalrekfyl cnssdfepld
phqlqisisk parvgmhrdl vegkvtairt ltspgvpekr hvefqipsem alrpgdhvni
lpvnppcsvl ralarfslas dhsitfessn aldlpqatpv saaelfssyl elsqpatrin
lkslasatps dddkkellhf hdsydslird krvsvldlle hftsitlpia tfismlpvlr
vrtyslsmap sfkplhcslt fsvvnepaws gngrylgvgs nylasltpgs ilyvsprpak
dafhlptdqs snpiimicag sglapfrsfi qdrmawlqqg kplakallff gcrgphlddl
yhdelsefes agvvevrray skvpnhylak gcryaqhrll tetetiqdmw ahnatlylcg
sanlakgvka vlenmlgtls eeryiteif SEQ ID NO: 31 *Penicillium freii* KUM63529
mkdmdcipgp kplpvvgnlf dldldnalqs iikmadefgp lfqitvnrqk hifatsqalv
delcdetrfh kaviggvekl rmlahdglft ahhgergwgi ahrilmpafg plrirdmfed
msdvahqlcf kwarqgssts inisedftrl tldtialctm sfrlnsyyns dtmhpfvqsm
lyvlkeadlq sslpevancv rvkaqrsmsk hieamrsiag diikgrrdkp epvndllntl
lngrdpvtge gmsdeliisn iitfliaghe ttsgllsftf yyllqhpqvl eqarnevdev
vgvgpitvqh laklpyidai mkeslrlmpt apsftvtpkk pevlggkwmi npgqsvhvll
pvclrdeavf gpdagefrpn rmleenfskl ppnswkpfgn gergcigraf awqeaqlvva
svlqtfdlva edpnyklrvk etltikpdgf rvratlrhgr satalsqhnm sagatsspgs -continued

| Sequence Appendix |
| --- |
| sahpagnkna qdaaggqsis ffygsnsgtc kalahrlast mmtrgftdqh lapldsavdn<br>lpkdqptiiv tttyegqptd dakkflawle sgivpslhgv syavfgcghq dwtktfyrip<br>iliddlmhka gatrittrge anaavsdlfs dlevweetnl lpalrekfda snsgefesld<br>lqqlqisisk ptrvgmhrdl iegkvtairt ltspgvpekr hvefqitsdt tlrpgdhvni<br>lpvnppstvl ralarfnlas dhiitfessn aldlpqatpv saaelfgsyl elsqpatrnn<br>lkslasttps dedkqellrf hdsydslird krvsvldlle hftsitlpia tfismlpvlr<br>vrtyslsmap sfkplhcslt fsvvnepaws gngrylgvgs nylasltpgs ilyvsprpak<br>eafhlpadqs skpiimicag sglapfrsfi qdrmawlqqg kplakallff gcrgpqlddl<br>yhdelsefes agvvevrray skvpnhypgk gcryvqhrlf aetetiqdmw ahnatlylcg<br>satlakgvka tlenmlgtls eeryiteif |

We claim:

1. A method for enzymatically producing a lactone under physiological conditions, the method comprising culturing a recombinant bacterium in the presence of a hydroxy acyl-CoA substrate, thereby producing said lactone, wherein said recombinant bacterium expresses a heterologous acyl-CoA thioesterase and a heterologous acyl-CoA synthetase protein, wherein:

the acyl-CoA thioesterase comprises a YbgC protein, wherein the YbgC protein has at least 85% amino acid sequence identity to any one of the amino acid sequence of SEQ ID NOs: 1-6, and wherein the YbgC protein converts a hydroxy acyl-CoA substrate to a lactone;

the hydroxy acyl-CoA substrate is a member selected from a 4-hydroxy acyl-CoA, a 5-hydroxy acyl-CoA, and a 6-hydroxy acyl-CoA; and the YbgC protein converts the 4-hydroxy acyl-CoA to a γ-lactone, the YbgC protein converts the 5-hydroxy acyl-CoA to a δ-lactone, and the YbgC protein converts the 6-hydroxy acyl-CoA to a ε-lactone.

2. The method of claim 1, wherein the YbgC protein is overexpressed in said recombinant bacterium.

3. The method of claim 1, further comprising exogenously adding a fatty acid derivative molecule to the culture medium to produce said hydroxy acyl-CoA substrate from the recombinant bacterium.

4. The method of claim 3, wherein the fatty acid derivative molecule is a 4-hydroxy fatty acid derivative, a 5-hydroxy fatty acid derivative or a 6-hydroxy fatty acid derivative.

5. The method of claim 4, wherein the fatty acid derivative molecule is the 4-hydroxy fatty acid derivative and the recombinant bacterium produces 4-hydroxy acyl-CoA.

6. The method of claim 5, wherein the 4-hydroxy fatty acid derivative is 4-hydroxy decanoic acid, 4-hydroxy octanoic acid, 4-hydroxy dodecanoic acid, or 4-hydroxy tetranoic acid.

7. The method of claim 4, wherein the fatty acid derivative molecule is the 5-hydroxy fatty acid derivative and the recombinant bacterium produces 5-hydroxy acyl-CoA.

8. The method of claim 7, wherein the 5-hydroxy fatty acid derivative is 5-hydroxy decanoic acid.

9. The method of claim 4, wherein the fatty acid derivative molecule is the 6-hydroxy fatty acid derivative and the recombinant bacterium produces 6-hydroxy acyl-CoA.

10. The method of claim 9, wherein the 6-hydroxy fatty acid derivative is 6-hydroxy hexanoic acid or 6-hydroxy decanoic acid.

11. The method of claim 1, wherein the YbgC protein has at least 85% amino acid sequence identity to the amino acid sequence of SEQ ID NO: 1.

12. The method of claim 1, wherein the recombinant bacterium further expresses a second heterologous thioesterase and a heterologous hydroxylating enzyme.

13. The method of claim 12, wherein:

the second thioesterase is a member selected from the group consisting of the amino acid sequence of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, and SEQ ID NO: 24; and the hydroxylating enzyme is a member selected from the group consisting of the amino acid sequence of SEQ ID NO: 25, SEQ ID NO: 26, SEQ ID NO: 27, SEQ ID NO: 28, SEQ ID NO; 29, SEQ ID NO: 30, and SEQ ID NO: 31.

14. The method of claim 1, wherein the recombinant bacterium produces the lactone from a simple carbon source.

15. The method of claim 1, wherein the recombinant bacterium comprises an endogenous acyl-CoA dehydrogenase that is attenuated or deleted or a 3-ketoacyl-CoA thiolase or dual 3-hydroxyacyl-CoA-dehydrogenase/dehydratase that is attenuated or deleted.

16. The method of claim 1, wherein the acyl-CoA synthetase is overexpressed.

17. The method of claim 1, further comprising recovering the lactone from the culture medium or isolating the lactone from the recombinant bacterium, or both.

18. The method of claim 1, wherein the lactone is produced without a chemical conversion step or acidification of the culture medium.

* * * * *

SEQUENCE LISTING

<160> NUMBER OF SEQ ID NOS: 32

<210> SEQ ID NO 1
<211> LENGTH: 134
<212> TYPE: PRT
<213> ORGANISM: Escherichia coli

<400> SEQUENCE: 1

```
Met Asn Thr Thr Leu Phe Arg Trp Pro Val Arg Val Tyr Tyr Glu Asp
1               5                   10                  15

Thr Asp Ala Gly Gly Val Val Tyr His Ala Ser Tyr Val Ala Phe Tyr
            20                  25                  30

Glu Arg Ala Arg Thr Glu Met Leu Arg His His His Phe Ser Gln Gln
        35                  40                  45

Ala Leu Met Ala Glu Arg Val Ala Phe Val Val Arg Lys Met Thr Val
    50                  55                  60

Glu Tyr Tyr Ala Pro Ala Arg Leu Asp Asp Met Leu Glu Ile Gln Thr
65                  70                  75                  80

Glu Ile Thr Ser Met Arg Gly Thr Ser Leu Val Phe Thr Gln Arg Ile
                85                  90                  95

Val Asn Ala Glu Asn Thr Leu Leu Asn Glu Ala Glu Val Leu Val Val
            100                 105                 110

Cys Val Asp Pro Leu Lys Met Lys Pro Arg Ala Leu Pro Lys Ser Ile
        115                 120                 125

Val Ala Glu Phe Lys Gln
    130
```

<210> SEQ ID NO 2
<211> LENGTH: 132
<212> TYPE: PRT
<213> ORGANISM: Citrobacter koseri

<400> SEQUENCE: 2

```
Met Asn Ile Phe Arg Trp Pro Val Arg Val Tyr Tyr Glu Asp Thr Asp
1               5                   10                  15

Ala Gly Gly Val Val Tyr His Ala Ser Tyr Val Ala Phe Tyr Glu Arg
            20                  25                  30

Ala Arg Thr Glu Met Leu Arg His His His Phe Ser Gln Gln Val Leu
        35                  40                  45

Leu Ala Glu Arg Val Ala Phe Val Val Arg Lys Met Thr Leu Glu Tyr
    50                  55                  60

Tyr Ala Pro Ala Arg Leu Asp Asp Met Leu Glu Val Gln Thr Glu Ile
65                  70                  75                  80

Thr Ser Met Arg Gly Thr Ser Leu Val Phe Thr Gln Arg Ile Val Asn
```

-continued

```
                85                  90                  95

Ala Glu Asn Asn Val Leu Asn Glu Ala Glu Val Leu Ile Val Cys Val
            100                 105                 110

Asp Pro Leu Lys Met Lys Pro Arg Ala Leu Pro Lys Ser Ile Val Ala
        115                 120                 125

Glu Phe Lys Gln
    130


<210> SEQ ID NO 3
<211> LENGTH: 134
<212> TYPE: PRT
<213> ORGANISM: Enterobacter cloacae

<400> SEQUENCE: 3

Met Asn Thr Thr Leu Phe Arg Trp Pro Val Arg Val Tyr Tyr Glu Asp
1               5                   10                  15

Thr Asp Ala Gly Gly Val Val Tyr His Ala Ser Tyr Val Ala Phe Tyr
            20                  25                  30

Glu Arg Ala Arg Thr Glu Met Leu Arg His His His Phe Ser Gln Gln
        35                  40                  45

Val Leu Leu Ala Glu Arg Val Ala Phe Val Val Arg Lys Met Thr Leu
    50                  55                  60

Glu Tyr Phe Ala Pro Ala Arg Leu Asp Asp Met Leu Glu Ile Gln Thr
65                  70                  75                  80

Glu Ile Thr Ser Met Arg Gly Thr Ser Leu Val Phe Thr Gln Arg Ile
                85                  90                  95

Val Asn Ala Glu Asn Thr Val Leu Asn Glu Ala Glu Val Leu Ile Val
            100                 105                 110

Cys Val Asp Pro Leu Leu Met Lys Pro Arg Ala Leu Pro Lys Ser Ile
        115                 120                 125

Val Ala Glu Phe Lys Gln
    130


<210> SEQ ID NO 4
<211> LENGTH: 135
<212> TYPE: PRT
<213> ORGANISM: Serratia fonticola

<400> SEQUENCE: 4

Met Ser Asn Lys Leu Phe Arg Trp Pro Val Arg Val Tyr Phe Glu Asp
1               5                   10                  15

Thr Asp Ala Gly Gly Val Val Tyr His Ala Arg Tyr Val Ala Phe Tyr
            20                  25                  30

Glu Arg Ala Arg Thr Glu Met Leu Arg Gln His Asn Phe His Gln Gln
        35                  40                  45

Gln Leu Leu Ser Glu Glu His Val Ala Phe Ala Val Arg Arg Met Thr
    50                  55                  60

Val Asp Tyr Leu Ser Pro Ala Arg Leu Asp Asp Leu Leu Glu Val Gln
65                  70                  75                  80

Ser Lys Ile Thr Ser Ile Arg Gly Ala Ser Leu Thr Phe Ala Gln Arg
                85                  90                  95

Ile Val Asn Ser Asp Gly Thr Leu Leu Ser Gln Ala Asp Val Leu Ile
            100                 105                 110

Ala Cys Ile Asp Pro His Gln Met Lys Pro Ile Ala Leu Pro Lys Ser
        115                 120                 125

Ile Val Ala Glu Phe Lys Gln
```

130 135

<210> SEQ ID NO 5
<211> LENGTH: 124
<212> TYPE: PRT
<213> ORGANISM: Exiguobacterium mexicanum

<400> SEQUENCE: 5

Met Leu Phe Arg Trp Pro Val Arg Val Tyr Tyr Glu Asp Thr Asp Ala
1 5 10 15

Gly Gly Val Val Tyr His Ala Arg Tyr Leu Ala Phe Phe Glu Arg Ala
20 25 30

Arg Thr Glu Met Leu Arg Asn Lys Gly Ile Asn Gln Gln Ser Met Leu
35 40 45

Ala Asp Asn Leu Gly Phe Val Val Arg Ser Met Thr Ile Asp Phe Val
50 55 60

Lys Gly Ala Lys Leu Asp Asp Leu Leu Glu Val Glu Thr Gln Ile Val
65 70 75 80

Glu Met Lys Arg Ala Ser Leu Thr Phe His Gln Arg Leu Val Asp Ser
85 90 95

Gln Gly Asn Leu Leu Cys Gly Ala Asn Ala Leu Ile Ala Cys Val Asp
100 105 110

Thr Ser Lys Met Lys Pro Ile Ala Leu Pro Lys Ser
115 120

<210> SEQ ID NO 6
<211> LENGTH: 136
<212> TYPE: PRT
<213> ORGANISM: Plesiomonas shigelloides

<400> SEQUENCE: 6

Met Ser Ser Lys Val Ser Gln Trp Pro Val Arg Val Tyr Tyr Glu Asp
1 5 10 15

Thr Asp Ala Gly Gly Val Val Tyr His Ala Arg Tyr Val Ala Phe Phe
20 25 30

Glu Arg Ala Arg Thr Glu Met Leu Arg Ser Leu Gly Gln Gln Gln Gln
35 40 45

Thr Leu Leu Gln His Asn Val Ala Phe Val Val Arg Arg Met Thr Val
50 55 60

Asp Tyr Arg Ser Pro Ala Arg Leu Asp Asp Leu Leu Ser Val Glu Thr
65 70 75 80

Glu Ile Ser Ser Phe Arg Gly Ala Ser Val Thr Phe Asn Gln Arg Ile
85 90 95

Ile His Gln Asp Gly Arg Val Leu Cys Thr Ala Glu Val Leu Val Ala
100 105 110

Cys Ile Asp Leu Ala Lys Met Lys Pro Val Ala Leu Pro Ala Glu Leu
115 120 125

Val Ala Glu Phe Thr Cys Val Cys
130 135

<210> SEQ ID NO 7
<211> LENGTH: 560
<212> TYPE: PRT
<213> ORGANISM: Escherichia coli

<400> SEQUENCE: 7

Met Lys Lys Val Trp Leu Asn Arg Tyr Pro Ala Asp Val Pro Thr Glu
1 5 10 15

-continued

```
Ile Asn Pro Asp Arg Tyr Gln Ser Leu Val Asp Met Phe Glu Gln Ser
            20                  25                  30

Val Ala Arg Tyr Ala Asp Gln Pro Ala Phe Val Asn Met Gly Glu Val
        35                  40                  45

Met Thr Phe Arg Lys Leu Glu Glu Arg Ser Arg Ala Phe Ala Ala Tyr
    50                  55                  60

Leu Gln Gln Gly Leu Gly Leu Lys Lys Gly Asp Arg Val Ala Leu Met
65                  70                  75                  80

Met Pro Asn Leu Leu Gln Tyr Pro Val Ala Leu Phe Gly Ile Leu Arg
                85                  90                  95

Ala Gly Met Ile Val Val Asn Val Asn Pro Leu Tyr Thr Pro Arg Glu
            100                 105                 110

Leu Glu His Gln Leu Asn Asp Ser Gly Ala Ser Ala Ile Val Ile Val
        115                 120                 125

Ser Asn Phe Ala His Thr Leu Glu Lys Val Val Asp Lys Thr Ala Val
    130                 135                 140

Gln His Val Ile Leu Thr Arg Met Gly Asp Gln Leu Ser Thr Ala Lys
145                 150                 155                 160

Gly Thr Val Val Asn Phe Val Val Lys Tyr Ile Lys Arg Leu Val Pro
                165                 170                 175

Lys Tyr His Leu Pro Asp Ala Ile Ser Phe Arg Ser Ala Leu His Asn
            180                 185                 190

Gly Tyr Arg Met Gln Tyr Val Lys Pro Glu Leu Val Pro Glu Asp Leu
        195                 200                 205

Ala Phe Leu Gln Tyr Thr Gly Gly Thr Thr Gly Val Ala Lys Gly Ala
    210                 215                 220

Met Leu Thr His Arg Asn Met Leu Ala Asn Leu Glu Gln Val Asn Ala
225                 230                 235                 240

Thr Tyr Gly Pro Leu Leu His Pro Gly Lys Glu Leu Val Val Thr Ala
                245                 250                 255

Leu Pro Leu Tyr His Ile Phe Ala Leu Thr Ile Asn Cys Leu Leu Phe
            260                 265                 270

Ile Glu Leu Gly Gly Gln Asn Leu Leu Ile Thr Asn Pro Arg Asp Ile
        275                 280                 285

Pro Gly Leu Val Lys Glu Leu Ala Lys Tyr Pro Phe Thr Ala Ile Thr
    290                 295                 300

Gly Val Asn Thr Leu Phe Asn Ala Leu Leu Asn Asn Glu Phe Gln Gln
305                 310                 315                 320

Leu Asp Phe Ser Ser Leu His Leu Ser Ala Gly Gly Gly Met Pro Val
                325                 330                 335

Gln Gln Val Val Ala Glu Arg Trp Val Lys Leu Thr Gly Gln Tyr Leu
            340                 345                 350

Leu Glu Gly Tyr Gly Leu Thr Glu Cys Ala Pro Leu Val Ser Val Asn
        355                 360                 365

Pro Tyr Asp Ile Asp Tyr His Ser Gly Ser Ile Gly Leu Pro Val Pro
    370                 375                 380

Ser Thr Glu Ala Lys Leu Val Asp Asp Asp Asp Asn Glu Val Pro Pro
385                 390                 395                 400

Gly Gln Pro Gly Glu Leu Cys Val Lys Gly Pro Gln Val Met Leu Gly
                405                 410                 415

Tyr Trp Gln Arg Pro Asp Ala Thr Asp Glu Ile Ile Lys Asn Gly Trp
            420                 425                 430
```

-continued

```
Leu His Thr Gly Asp Ile Ala Val Met Asp Glu Glu Gly Phe Leu Arg
        435                 440                 445

Ile Val Asp Arg Lys Lys Asp Met Ile Leu Val Ser Gly Phe Asn Val
    450                 455                 460

Tyr Pro Asn Glu Ile Glu Asp Val Val Met Gln His Pro Gly Val Gln
465                 470                 475                 480

Glu Val Ala Ala Val Gly Val Pro Ser Gly Ser Ser Gly Glu Ala Val
                485                 490                 495

Lys Ile Phe Val Val Lys Lys Asp Pro Ser Leu Thr Glu Glu Ser Leu
            500                 505                 510

Val Thr Phe Cys Arg Arg Gln Leu Thr Gly Tyr Lys Val Pro Lys Leu
        515                 520                 525

Val Glu Phe Arg Asp Glu Leu Pro Lys Ser Asn Val Gly Lys Ile Leu
    530                 535                 540

Arg Arg Glu Leu Arg Asp Glu Ala Arg Gly Lys Val Asp Asn Lys Ala
545                 550                 555                 560


<210> SEQ ID NO 8
<211> LENGTH: 565
<212> TYPE: PRT
<213> ORGANISM: Pseudomonas putida

<400> SEQUENCE: 8

Met Ile Glu Asn Phe Trp Lys Asp Lys Tyr Pro Ala Gly Ile Thr Ala
1               5                   10                  15

Glu Ile Asn Pro Asp Glu Phe Pro Asn Ile Gln Ala Val Leu Lys Gln
            20                  25                  30

Ser Cys Gln Arg Phe Ala Asp Lys Pro Ala Phe Ser Asn Leu Gly Lys
        35                  40                  45

Thr Ile Thr Tyr Gly Glu Leu Tyr Ala Leu Ser Gly Ala Phe Ala Ala
    50                  55                  60

Trp Leu Gln Gln His Thr Asp Leu Lys Pro Gly Asp Arg Ile Ala Val
65                  70                  75                  80

Gln Leu Pro Asn Val Leu Gln Tyr Pro Val Ala Val Phe Gly Ala Met
                85                  90                  95

Arg Ala Gly Leu Ile Val Val Asn Thr Asn Pro Leu Tyr Thr Ala Arg
            100                 105                 110

Glu Met Glu His Gln Phe Asn Asp Ser Gly Ala Lys Ala Leu Val Cys
        115                 120                 125

Leu Ala Asn Met Ala His Leu Ala Glu Lys Val Val Pro Lys Thr Gln
    130                 135                 140

Val Arg His Val Ile Val Thr Glu Val Ala Asp Leu Leu Pro Pro Leu
145                 150                 155                 160

Lys Arg Leu Leu Ile Asn Ser Val Ile Lys Tyr Val Lys Lys Met Val
                165                 170                 175

Pro Ala Tyr Asn Leu Pro Gln Ala Val Arg Phe Asn Asp Ala Leu Ala
            180                 185                 190

Leu Gly Lys Gly Gln Pro Val Thr Glu Ala Asn Pro Gln Ala Asn Asp
        195                 200                 205

Val Ala Val Leu Gln Tyr Thr Gly Gly Thr Thr Gly Val Ala Lys Gly
    210                 215                 220

Ala Met Leu Thr His Arg Asn Leu Val Ala Asn Met Leu Gln Cys Arg
225                 230                 235                 240

Ala Leu Met Gly Ser Asn Leu His Glu Gly Cys Glu Ile Leu Ile Thr
                245                 250                 255
```

Pro Leu Pro Leu Tyr His Ile Tyr Ala Phe Thr Phe His Cys Met Ala
260 265 270

Met Met Leu Ile Gly Asn His Asn Val Leu Ile Ser Asn Pro Arg Asp
275 280 285

Leu Pro Ala Met Val Lys Glu Leu Gly Lys Trp Lys Phe Ser Gly Phe
290 295 300

Val Gly Leu Asn Thr Leu Phe Val Ala Leu Cys Asn Asn Glu Ala Phe
305 310 315 320

Arg Ala Leu Asp Phe Ser Ala Leu Lys Ile Thr Leu Ser Gly Gly Met
325 330 335

Ala Leu Gln Leu Ser Val Ala Glu Arg Trp Lys Ala Val Thr Gly Cys
340 345 350

Ala Ile Cys Glu Gly Tyr Gly Met Thr Glu Thr Ser Pro Val Ala Ala
355 360 365

Val Asn Pro Ser Glu Ala Asn Gln Val Gly Thr Ile Gly Ile Pro Val
370 375 380

Pro Ser Thr Leu Cys Lys Val Ile Asp Asp Ala Gly Asn Glu Leu Pro
385 390 395 400

Leu Gly Glu Val Gly Glu Leu Cys Val Lys Gly Pro Gln Val Met Lys
405 410 415

Gly Tyr Trp Gln Arg Glu Asp Ala Thr Ala Glu Ile Leu Asp Ser Glu
420 425 430

Gly Trp Leu Lys Thr Gly Asp Ile Ala Val Ile Gln Ala Asp Gly Tyr
435 440 445

Met Arg Ile Val Asp Arg Lys Lys Asp Met Ile Leu Val Ser Gly Phe
450 455 460

Asn Val Tyr Pro Asn Glu Leu Glu Asp Val Leu Ala Ala Leu Pro Gly
465 470 475 480

Val Leu Gln Cys Ala Ala Ile Gly Val Pro Asp Glu Lys Ser Gly Glu
485 490 495

Val Ile Lys Val Phe Ile Val Val Lys Pro Gly Met Thr Val Thr Lys
500 505 510

Glu Gln Val Met Glu His Met Arg Ala Asn Val Thr Gly Tyr Lys Val
515 520 525

Pro Arg His Ile Glu Phe Arg Asp Ser Leu Pro Thr Thr Asn Val Gly
530 535 540

Lys Ile Leu Arg Arg Glu Leu Arg Asp Glu Glu Leu Lys Lys Gln Gly
545 550 555 560

Leu Lys Lys Ile Ala
565

<210> SEQ ID NO 9
<211> LENGTH: 562
<212> TYPE: PRT
<213> ORGANISM: Pseudomonas putida

<400> SEQUENCE: 9

Met Gln Ala Asp Phe Trp Asn Asp Lys Arg Pro Ala Gly Val Pro Ser
1 5 10 15

Thr Ile Asp Ile Asn Ala Tyr Ala Ser Val Val Glu Val Phe Glu Arg
20 25 30

Ser Cys Lys Arg Phe Ala Asp Arg Pro Ala Phe Ser Asn Leu Gly Val
35 40 45

Thr Leu Ser Tyr Ala Glu Leu Glu Arg His Ser Ala Ala Phe Ala Ala

-continued

```
    50                  55                  60

Trp Leu Gln Gln His Thr Asp Leu Lys Pro Gly Glu Arg Ile Ala Val
65                  70                  75                  80

Gln Met Pro Asn Val Leu Gln Tyr Pro Ile Ala Val Phe Gly Ala Met
                85                  90                  95

Arg Ala Gly Leu Ile Val Val Asn Thr Asn Pro Leu Tyr Thr Glu Arg
            100                 105                 110

Glu Met Arg His Gln Phe Lys Asp Ser Gly Ala Arg Ala Leu Val Tyr
        115                 120                 125

Leu Asn Met Phe Gly Lys Arg Val Gln Glu Val Leu Pro Asp Thr Gly
    130                 135                 140

Ile Glu Tyr Leu Ile Glu Ala Lys Met Gly Asp Leu Leu Pro Ala Ala
145                 150                 155                 160

Lys Gly Trp Leu Val Asn Thr Val Val Asp Lys Leu Lys Lys Met Val
                165                 170                 175

Pro Ala Tyr Arg Leu Pro Gln Ala Val Pro Phe Lys Gln Val Leu Arg
            180                 185                 190

Glu Gly Arg Gly Leu Ser Pro Lys Pro Val Ser Leu Asn Leu Asp Asp
        195                 200                 205

Ile Ala Val Leu Gln Tyr Thr Gly Gly Thr Thr Gly Leu Ala Lys Gly
    210                 215                 220

Ala Met Leu Thr His Gly Asn Leu Val Ala Asn Met Leu Gln Val Leu
225                 230                 235                 240

Ala Cys Phe Ser Gln His Gly Pro Asp Gly Gln Lys Leu Leu Lys Asp
                245                 250                 255

Gly Gln Glu Val Met Ile Ala Pro Leu Pro Leu Tyr His Ile Tyr Ala
            260                 265                 270

Phe Thr Ala Asn Cys Met Cys Met Met Val Thr Gly Asn His Asn Val
        275                 280                 285

Leu Ile Thr Asn Pro Arg Asp Ile Pro Gly Phe Ile Lys Glu Leu Gly
    290                 295                 300

Lys Trp Arg Phe Ser Ala Leu Leu Gly Leu Asn Thr Leu Phe Val Ala
305                 310                 315                 320

Leu Met Asp His Pro Gly Phe Arg Gln Leu Asp Phe Ser Ala Leu Lys
                325                 330                 335

Val Thr Asn Ser Gly Gly Thr Ala Leu Val Lys Ala Thr Ala Glu Arg
            340                 345                 350

Trp Glu Asp Leu Thr Gly Cys Arg Ile Val Glu Gly Tyr Gly Leu Thr
        355                 360                 365

Glu Thr Ser Pro Val Ala Ser Thr Asn Pro Tyr Gly Gln Leu Ala Arg
    370                 375                 380

Leu Gly Thr Val Gly Ile Pro Val Ala Gly Thr Ala Phe Lys Val Ile
385                 390                 395                 400

Asp Asp Asp Gly Asn Glu Leu Pro Leu Gly Glu Arg Gly Glu Leu Cys
                405                 410                 415

Ile Lys Gly Pro Gln Val Met Lys Gly Tyr Trp Gln Gln Pro Glu Ala
            420                 425                 430

Thr Ala Gln Ala Leu Asp Ala Glu Gly Trp Phe Lys Thr Gly Asp Ile
        435                 440                 445

Ala Val Ile Asp Pro Asp Gly Phe Thr Arg Ile Val Asp Arg Lys Lys
    450                 455                 460

Asp Met Ile Ile Val Ser Gly Phe Asn Val Tyr Pro Asn Glu Ile Glu
465                 470                 475                 480
```

```
Asp Val Val Met Gly His Pro Lys Val Ala Asn Cys Ala Ala Ile Gly
                485                 490                 495

Val Pro Asp Glu Arg Ser Gly Glu Ala Val Lys Leu Phe Val Val Pro
            500                 505                 510

Arg Glu Gly Gly Leu Ser Val Asp Glu Leu Lys Ala Tyr Cys Lys Ala
        515                 520                 525

Asn Phe Thr Gly Tyr Lys Val Pro Lys His Ile Val Leu Arg Glu Ser
    530                 535                 540

Leu Pro Met Thr Pro Val Gly Lys Ile Leu Arg Arg Glu Leu Arg Asp
545                 550                 555                 560

Ile Ala


<210> SEQ ID NO 10
<211> LENGTH: 560
<212> TYPE: PRT
<213> ORGANISM: Pseudomonas putida

<400> SEQUENCE: 10

Met Leu Gln Thr Arg Ile Ile Lys Pro Ala Glu Gly Ala Tyr Ala Tyr
1               5                   10                  15

Pro Leu Leu Ile Lys Arg Leu Leu Met Ser Gly Ser Arg Tyr Glu Lys
            20                  25                  30

Thr Arg Glu Ile Val Tyr Arg Asp Gln Met Arg Leu Thr Tyr Pro Gln
        35                  40                  45

Leu Asn Glu Arg Ile Ala Arg Leu Ala Asn Val Leu Thr Glu Ala Gly
    50                  55                  60

Val Lys Ala Gly Asp Thr Val Ala Val Met Asp Trp Asp Ser His Arg
65                  70                  75                  80

Tyr Leu Glu Cys Met Phe Ala Ile Pro Met Ile Gly Ala Val Val His
                85                  90                  95

Thr Ile Asn Val Arg Leu Ser Pro Glu Gln Ile Leu Tyr Thr Met Asn
            100                 105                 110

His Ala Glu Asp Arg Val Val Leu Val Asn Ser Asp Phe Val Gly Leu
        115                 120                 125

Tyr Gln Ala Ile Ala Gly Gln Leu Thr Thr Val Asp Lys Thr Leu Leu
    130                 135                 140

Leu Thr Asp Gly Pro Asp Lys Thr Ala Glu Leu Pro Gly Leu Val Gly
145                 150                 155                 160

Glu Tyr Glu Gln Leu Leu Ala Ala Ala Ser Pro Arg Tyr Asp Phe Pro
                165                 170                 175

Asp Phe Asp Glu Asn Ser Val Ala Thr Thr Phe Tyr Thr Thr Gly Thr
            180                 185                 190

Thr Gly Asn Pro Lys Gly Val Tyr Phe Ser His Arg Gln Leu Val Leu
        195                 200                 205

His Thr Leu Ala Glu Ala Ser Val Thr Gly Ser Ile Asp Ser Val Arg
    210                 215                 220

Leu Leu Gly Ser Asn Asp Val Tyr Met Pro Ile Thr Pro Met Phe His
225                 230                 235                 240

Val His Ala Trp Gly Ile Pro Tyr Ala Ala Thr Met Leu Gly Met Lys
                245                 250                 255

Gln Val Tyr Pro Gly Arg Tyr Glu Pro Asp Met Leu Val Lys Leu Trp
            260                 265                 270

Arg Glu Glu Lys Val Thr Phe Ser His Cys Val Pro Thr Ile Leu Gln
        275                 280                 285
```

-continued

Met Leu Leu Asn Cys Pro Asn Ala Gln Gly Gln Asp Phe Gly Gly Trp
290 295 300

Lys Ile Ile Ile Gly Gly Ser Ser Leu Asn Arg Ser Leu Tyr Gln Ala
305 310 315 320

Ala Leu Ala Arg Gly Ile Gln Leu Thr Ala Ala Tyr Gly Met Ser Glu
325 330 335

Thr Cys Pro Leu Ile Ser Ala Ala His Leu Asn Asp Glu Leu Gln Ala
340 345 350

Gly Ser Glu Asp Glu Arg Val Thr Tyr Arg Ile Lys Ala Gly Val Pro
355 360 365

Val Pro Leu Val Glu Ala Ala Ile Val Asp Gly Glu Gly Asn Phe Leu
370 375 380

Pro Ala Asp Gly Glu Thr Gln Gly Glu Leu Val Leu Arg Ala Pro Trp
385 390 395 400

Leu Thr Met Gly Tyr Phe Lys Glu Pro Glu Lys Ser Glu Glu Leu Trp
405 410 415

Gln Gly Gly Trp Leu His Thr Gly Asp Val Ala Thr Leu Asp Gly Met
420 425 430

Gly Tyr Ile Asp Ile Arg Asp Arg Ile Lys Asp Val Ile Lys Thr Gly
435 440 445

Gly Glu Trp Val Ser Ser Leu Asp Leu Glu Asp Leu Ile Ser Arg His
450 455 460

Pro Ala Val Arg Glu Val Ala Val Val Gly Val Ala Asp Pro Gln Trp
465 470 475 480

Gly Glu Arg Pro Phe Ala Leu Leu Val Ala Arg Asp Gly His Asp Ile
485 490 495

Asp Ala Lys Ala Leu Lys Glu His Leu Lys Pro Phe Val Glu Gln Gly
500 505 510

His Ile Asn Lys Trp Ala Ile Pro Ser Gln Ile Ala Leu Val Thr Glu
515 520 525

Ile Pro Lys Thr Ser Val Gly Lys Leu Asp Lys Lys Arg Ile Arg Gln
530 535 540

Asp Ile Val Gln Trp Gln Ala Ser Asn Ser Ala Phe Leu Ser Thr Leu
545 550 555 560

<210> SEQ ID NO 11
<211> LENGTH: 560
<212> TYPE: PRT
<213> ORGANISM: Pseudomonas aeruginosa

<400> SEQUENCE: 11

Met Leu Lys Thr Arg Leu Ile Pro Ala Ala Ala Gly Ala Tyr Gln Tyr
1 5 10 15

Pro Leu Leu Ile Lys Ser Leu Met Leu Ser Gly Arg Arg Tyr Glu Lys
20 25 30

Ser His Glu Ile Val Tyr Arg Asp Gln Val Arg Tyr Ser Tyr Ala Thr
35 40 45

Phe Asn Glu Arg Val Ala Arg Leu Ala Asn Val Leu Ser Glu Ala Gly
50 55 60

Val Lys Ala Gly Asp Thr Val Ala Val Met Asp Trp Asp Ser His Arg
65 70 75 80

Tyr Leu Glu Cys Met Phe Ala Ile Pro Met Ile Gly Ala Val Leu His
85 90 95

Thr Ile Asn Ile Arg Leu Ser Pro Glu Gln Ile Leu Tyr Thr Met Asn

-continued

```
            100                 105                 110

His Ala Glu Asp Arg Phe Val Leu Val Asn Ser Glu Phe Val Pro Leu
        115                 120                 125

Tyr Gln Ala Val Ala Gly Gln Leu Ala Thr Val Glu Arg Thr Ile Leu
    130                 135                 140

Leu Thr Asp Gly Ala Glu Lys Ser Ala Glu Leu Pro Gly Leu Val Gly
145                 150                 155                 160

Glu Tyr Glu Ser Leu Leu Ala Ala Ala Ser Pro Arg Tyr Asp Phe Pro
                165                 170                 175

Asp Phe Asp Glu Asn Ser Ile Ala Thr Thr Phe Tyr Thr Thr Gly Thr
            180                 185                 190

Thr Gly Asn Pro Lys Gly Val Tyr Phe Ser His Arg Gln Leu Val Leu
        195                 200                 205

His Thr Leu Ala Met Ala Ser Thr Ile Gly Ser Leu Asp Ser Ile Arg
    210                 215                 220

Leu Leu Gly Thr Ser Asp Val Tyr Met Pro Ile Thr Pro Met Phe His
225                 230                 235                 240

Val His Ala Trp Gly Thr Pro Tyr Val Ala Thr Met Leu Gly Val Lys
                245                 250                 255

Gln Val Tyr Pro Gly Arg Tyr Asp Pro Glu Leu Leu Val Glu Leu Trp
            260                 265                 270

Lys Arg Glu Lys Val Thr Phe Ser His Cys Val Pro Thr Ile Leu Gln
        275                 280                 285

Met Val Met Asn Ala Arg Ala Ala Gln Gly Val Asp Phe Lys Gly Trp
    290                 295                 300

Lys Val Ile Ile Gly Gly Ser Ala Leu Asn Arg Ser Leu Tyr Glu Ala
305                 310                 315                 320

Ala Lys Ala Arg Gly Ile Gln Leu Thr Ala Ala Tyr Gly Met Ser Glu
                325                 330                 335

Thr Cys Pro Leu Ile Ser Cys Ala Tyr Leu Asn Asp Glu Leu Leu Ala
            340                 345                 350

Gly Ser Glu Asp Glu Arg Thr Thr Tyr Arg Ile Lys Ala Gly Val Pro
        355                 360                 365

Val Pro Leu Val Asp Ala Ala Ile Met Asp Glu Gln Gly Arg Phe Leu
    370                 375                 380

Pro Ala Asp Gly Glu Ser Gln Gly Glu Leu Val Leu Arg Ser Pro Trp
385                 390                 395                 400

Leu Thr Gln Gly Tyr Phe Arg Glu Pro Glu Arg Gly Glu Glu Leu Trp
                405                 410                 415

Arg Gly Gly Trp Met His Thr Gly Asp Val Ala Thr Leu Asp Gly Met
            420                 425                 430

Gly Phe Ile Glu Ile Arg Asp Arg Ile Lys Asp Val Ile Lys Thr Gly
        435                 440                 445

Gly Glu Trp Leu Ser Ser Leu Glu Leu Glu Asp Leu Ile Ser Arg His
    450                 455                 460

Pro Ala Val Arg Glu Val Ala Val Val Gly Val Pro Asp Pro Gln Trp
465                 470                 475                 480

Gly Glu Arg Pro Phe Ala Leu Leu Val Val Arg Glu Gly Gln Gln Leu
                485                 490                 495

Asp Ala Arg Gly Leu Lys Glu His Leu Lys Pro Phe Val Glu Gln Gly
            500                 505                 510

Asn Ile Asn Lys Trp Ala Ile Pro Ser Gln Ile Ala Val Val Thr Asp
        515                 520                 525
```

Ile Pro Lys Thr Ser Val Gly Lys Leu Asp Lys Lys Arg Ile Arg Ile
    530                 535                 540

Glu Ile Ala Gln Trp Gln Glu Ala Gly Ser Ala Phe Leu Ser Thr Val
545                 550                 555                 560

<210> SEQ ID NO 12
<211> LENGTH: 560
<212> TYPE: PRT
<213> ORGANISM: Pseudomonas citronellolis

<400> SEQUENCE: 12

Met Leu Lys Thr Arg Leu Leu Pro Ala Ala Ser Asn Ala Tyr Gln Tyr
1               5                   10                  15

Pro Leu Leu Ile Lys Ser Leu Leu Leu Ser Gly Ala Arg Tyr Glu Lys
            20                  25                  30

Ser Arg Glu Ile Val Tyr Arg Asp Leu Val Arg Tyr Asn Tyr Ala Thr
        35                  40                  45

Phe Asn Glu Arg Val Ala Arg Leu Ala Asn Val Leu Thr Glu Ala Gly
    50                  55                  60

Val Gln Ala Gly Asp Thr Val Ala Val Met Asp Trp Asp Ser His Arg
65                  70                  75                  80

Tyr Leu Glu Ala Met Phe Ala Ile Pro Met Ile Gly Ala Val Leu His
                85                  90                  95

Thr Ile Asn Ile Arg Leu Ser Pro Asp Gln Ile Leu Tyr Thr Met Asn
            100                 105                 110

His Ala Glu Asp Arg Phe Val Leu Val Asn Ala Glu Phe Val Pro Leu
        115                 120                 125

Tyr Gln Gly Ile Ala Gly Gln Leu Thr Thr Val Gln Lys Thr Leu Leu
    130                 135                 140

Leu Ser Asp Gly Ala Asp Lys Ser Cys Ala Leu Asp Asp Cys Ile Gly
145                 150                 155                 160

Glu Tyr Glu Thr Leu Met Ala Ala Ala Ser Pro Arg Tyr Ala Phe Pro
                165                 170                 175

Asp Phe Asp Glu Asn Ser Val Ala Thr Thr Phe Tyr Thr Thr Gly Thr
            180                 185                 190

Thr Gly Asn Pro Lys Gly Val Tyr Phe Thr His Arg Gln Leu Val Leu
        195                 200                 205

His Thr Leu Ala Met Ala Ser Thr Ile Ala Ser Leu Asp Ser Ile Arg
    210                 215                 220

Leu Met Gly Asn Ser Asp Val Tyr Met Pro Ile Thr Pro Met Phe His
225                 230                 235                 240

Val His Ala Trp Gly Val Pro Tyr Val Ala Thr Met Leu Gly Ile Lys
                245                 250                 255

Gln Val Tyr Pro Gly Arg Tyr Asp Pro Glu Leu Leu Val Asp Leu Trp
            260                 265                 270

Lys Arg Glu Asn Val Thr Phe Ser His Cys Val Pro Thr Ile Leu Gln
        275                 280                 285

Met Val Met Asn Ala Lys Ala Ala Gln Gly Val Asp Phe Lys Asp Trp
    290                 295                 300

Lys Ile Ile Ile Gly Gly Ser Ala Leu Asn Arg Ser Leu Tyr Glu Ala
305                 310                 315                 320

Ala Gln Ala Arg Gly Ile Gln Leu Thr Ala Ala Tyr Gly Met Ser Glu
                325                 330                 335

Thr Cys Pro Leu Ile Ser Cys Ala Tyr Leu Asn Asp Glu Leu Leu Ala

-continued

```
            340                 345                 350

Gly Ser Glu Asp Glu Arg Thr Thr Tyr Arg Ile Lys Ala Gly Val Pro
        355                 360                 365

Val Pro Leu Val Asp Ala Ala Ile Met Asp Glu His Gly Gln Leu Leu
    370                 375                 380

Pro Ala Asp Gly Glu Ser Gln Gly Glu Leu Val Leu Arg Ser Pro Trp
385                 390                 395                 400

Leu Thr Gln Gly Tyr Phe Arg Glu Pro Gln Lys Gly Glu Glu Leu Trp
                405                 410                 415

Ala Gly Gly Trp Met His Thr Gly Asp Val Ala Thr Leu Asp Gly Met
            420                 425                 430

Gly Phe Ile Asp Ile Arg Asp Arg Ile Lys Asp Val Ile Lys Thr Gly
        435                 440                 445

Gly Glu Trp Leu Ser Ser Leu Glu Leu Glu Asp Leu Ile Ser Arg His
    450                 455                 460

Pro Ala Val Arg Glu Val Ala Val Val Gly Val Pro Asp Pro Gln Trp
465                 470                 475                 480

Gly Glu Arg Pro Phe Ala Leu Leu Val Leu Phe Glu Gly Gln Gln Leu
                485                 490                 495

Asp Ala Lys Gly Leu Lys Glu His Leu Lys Pro Phe Val Glu Gln Gly
            500                 505                 510

His Ile Asn Lys Trp Ala Ile Pro Ser Gln Ile Ala Val Val Thr Glu
        515                 520                 525

Val Pro Lys Thr Ser Val Gly Lys Leu Asp Lys Lys Arg Ile Arg Val
    530                 535                 540

Asp Ile Ala Arg Trp Gln Glu Ser Gly Ser Glu Phe Leu Ser Ala Leu
545                 550                 555                 560


<210> SEQ ID NO 13
<211> LENGTH: 560
<212> TYPE: PRT
<213> ORGANISM: Pseudomonas mendocina

<400> SEQUENCE: 13

Met Leu Gln Thr Arg Leu Ile Pro Pro Ala Asn Asn Ala His Ala Tyr
1               5                   10                  15

Pro Leu Leu Ile Lys Arg Leu Leu Leu Ser Gly Ser Arg Tyr Glu Lys
            20                  25                  30

Thr Arg Glu Ile Val Tyr Arg Asp Lys Leu Arg Tyr Ser Tyr Ala Thr
        35                  40                  45

Phe Thr Glu Arg Val Ala Arg Leu Ala Asn Val Leu Ser Gln Ala Gly
    50                  55                  60

Val Lys Ala Gly Asp Thr Val Ala Val Met Asp Trp Asp Ser His Arg
65                  70                  75                  80

Tyr Leu Glu Cys Met Phe Ala Ile Pro Met Leu Gly Ala Val Leu His
                85                  90                  95

Thr Ile Asn Ile Arg Leu Ser Pro Asp Gln Ile Leu Tyr Thr Met Asn
            100                 105                 110

His Ala Glu Asp Arg Phe Val Leu Val Asn Ser Glu Phe Val Pro Leu
        115                 120                 125

Tyr Asn Gly Ile Ala Gly Gln Leu Thr Thr Val Glu Lys Thr Leu Leu
    130                 135                 140

Leu Thr Asp Gly Glu Asp Lys Asn Ala Asp Leu Pro Asn Leu Val Gly
145                 150                 155                 160
```

-continued

```
Glu Tyr Glu Ser Leu Leu Ala Ala Ala Ser Pro His Tyr Asp Phe Ala
                165                 170                 175

Asp Phe Asp Glu Asn Ser Val Ala Thr Thr Phe Tyr Thr Thr Gly Thr
            180                 185                 190

Thr Gly Asn Pro Lys Gly Val Tyr Phe Thr His Arg Gln Leu Val Leu
        195                 200                 205

His Thr Met Ser Met Ala Thr Thr Met Gly Gly Leu Asp Ser Ile Arg
    210                 215                 220

Leu Met Gly Asn Asp Asp Val Tyr Met Pro Ile Thr Pro Met Phe His
225                 230                 235                 240

Val His Ala Trp Gly Val Pro Tyr Val Ala Thr Met Leu Gly Val Lys
                245                 250                 255

Gln Val Tyr Pro Gly Arg Tyr Glu Pro Asp Met Leu Cys Arg Leu Ile
            260                 265                 270

Lys Glu Glu Lys Val Thr Phe Ser His Cys Val Pro Thr Ile Leu Gln
        275                 280                 285

Met Leu Leu Ser Ala Pro Gly Ala Gln Gly His Asp Phe Gly Gly Met
    290                 295                 300

Lys Met Ile Ile Gly Gly Ser Ala Leu Asn Arg Ser Leu Tyr Glu Ala
305                 310                 315                 320

Ala Lys Glu Arg Gly Ile Gln Leu Thr Ala Ala Tyr Gly Met Ser Glu
                325                 330                 335

Thr Cys Pro Leu Ile Ser Cys Ala Tyr Leu Asn Glu Glu Leu Arg Ala
            340                 345                 350

Gly Ser Glu Asp Glu Arg Thr Thr Tyr Arg Ile Lys Ala Gly Ile Pro
        355                 360                 365

Val Pro Leu Val Glu Ala Ala Ile Met Asp Ala Asp Gly Lys Leu Leu
    370                 375                 380

Pro Ser Asp Gly Glu Ser Gln Gly Glu Leu Val Leu Arg Ala Pro Trp
385                 390                 395                 400

Leu Thr Gln Gly Tyr Phe Arg Glu Pro Glu Lys Gly Glu Glu Leu Trp
                405                 410                 415

Ala His Gly Trp Leu His Thr Gly Asp Val Ala Thr Ile Asp Gly Met
            420                 425                 430

Gly Phe Ile Glu Ile Arg Asp Arg Ile Lys Asp Val Ile Lys Thr Gly
        435                 440                 445

Gly Glu Trp Ile Ser Ser Leu Glu Leu Glu Asp Leu Ile Ser Arg His
    450                 455                 460

Ser Ala Val Arg Glu Val Ala Val Val Gly Val Pro Asp Pro Gln Trp
465                 470                 475                 480

Gly Glu Arg Pro Phe Ala Leu Val Val Leu Arg Asp Ala Gln Gly Leu
                485                 490                 495

Asp Ala Lys Gly Leu Lys Glu His Leu Lys Pro Phe Val Glu Gln Gly
            500                 505                 510

His Ile Asn Lys Trp Ala Ile Pro Thr Gln Ile Ala Leu Val Thr Glu
        515                 520                 525

Ile Pro Lys Thr Ser Val Gly Lys Leu Asp Lys Lys Arg Ile Arg Val
    530                 535                 540

Glu Ile Ala Gln Trp Gln Glu Ala Gly Ser Thr Phe Leu Ser Thr Leu
545                 550                 555                 560
```

<210> SEQ ID NO 14
<211> LENGTH: 512
<212> TYPE: PRT

-continued

<213> ORGANISM: Bacillus subtilis

<400> SEQUENCE: 14

```
Met Asn Leu Val Ser Lys Leu Glu Glu Thr Ala Ser Glu Lys Pro Asp
1               5                   10                  15

Ser Ile Ala Cys Arg Phe Lys Asp His Met Met Thr Tyr Gln Glu Leu
            20                  25                  30

Asn Glu Tyr Ile Gln Arg Phe Ala Asp Gly Leu Gln Glu Ala Gly Met
        35                  40                  45

Glu Lys Gly Asp His Leu Ala Leu Leu Leu Gly Asn Ser Pro Asp Phe
    50                  55                  60

Ile Ile Ala Phe Phe Gly Ala Leu Lys Ala Gly Ile Val Val Val Pro
65                  70                  75                  80

Ile Asn Pro Leu Tyr Thr Pro Thr Glu Ile Gly Tyr Met Leu Thr Asn
                85                  90                  95

Gly Asp Val Lys Ala Ile Val Gly Val Ser Gln Leu Leu Pro Leu Tyr
            100                 105                 110

Glu Ser Met His Glu Ser Leu Pro Lys Val Glu Leu Val Ile Leu Cys
        115                 120                 125

Gln Thr Gly Glu Ala Glu Pro Glu Ala Ala Asp Pro Glu Val Arg Met
    130                 135                 140

Lys Met Thr Thr Phe Ala Lys Ile Leu Arg Pro Thr Ser Ala Ala Lys
145                 150                 155                 160

Gln Asn Gln Glu Pro Val Pro Asp Asp Thr Ala Val Ile Leu Tyr Thr
                165                 170                 175

Ser Gly Thr Thr Gly Lys Pro Lys Gly Ala Met Leu Thr His Gln Asn
            180                 185                 190

Leu Tyr Ser Asn Ala Asn Asp Val Ala Gly Tyr Leu Gly Met Asp Glu
        195                 200                 205

Arg Asp Asn Val Val Cys Ala Leu Pro Met Phe His Val Phe Cys Leu
    210                 215                 220

Thr Val Cys Met Asn Ala Pro Leu Met Ser Gly Ala Thr Val Leu Ile
225                 230                 235                 240

Glu Pro Gln Phe Ser Pro Ala Ser Val Phe Lys Leu Val Lys Gln Gln
                245                 250                 255

Gln Ala Thr Ile Phe Ala Gly Val Pro Thr Met Tyr Asn Tyr Leu Phe
            260                 265                 270

Gln His Glu Asn Gly Lys Lys Asp Asp Phe Ser Ser Ile Arg Leu Cys
        275                 280                 285

Ile Ser Gly Gly Ala Ser Met Pro Val Ala Leu Leu Thr Ala Phe Glu
    290                 295                 300

Glu Lys Phe Gly Val Thr Ile Leu Glu Gly Tyr Gly Leu Ser Glu Ala
305                 310                 315                 320

Ser Pro Val Thr Cys Phe Asn Pro Phe Asp Arg Gly Arg Lys Pro Gly
                325                 330                 335

Ser Ile Gly Thr Ser Ile Leu His Val Glu Asn Lys Val Val Asp Pro
            340                 345                 350

Leu Gly Arg Glu Leu Pro Ala His Gln Val Gly Glu Leu Ile Val Lys
        355                 360                 365

Gly Pro Asn Val Met Lys Gly Tyr Tyr Lys Met Pro Met Glu Thr Glu
    370                 375                 380

His Ala Leu Lys Asp Gly Trp Leu Tyr Thr Gly Asp Leu Ala Arg Arg
385                 390                 395                 400
```

-continued

```
Asp Glu Asp Gly Tyr Phe Tyr Ile Val Asp Arg Lys Lys Asp Met Ile
            405                 410                 415

Ile Val Gly Gly Tyr Asn Val Tyr Pro Arg Glu Val Glu Glu Val Leu
            420                 425                 430

Tyr Ser His Pro Asp Val Lys Glu Ala Val Val Ile Gly Val Pro Asp
        435                 440                 445

Pro Gln Ser Gly Glu Ala Val Lys Gly Tyr Val Val Pro Lys Arg Ser
    450                 455                 460

Gly Val Thr Glu Glu Asp Ile Met Gln His Cys Glu His Leu Ala Lys
465                 470                 475                 480

Tyr Lys Arg Pro Ala Ala Ile Thr Phe Leu Asp Asp Ile Pro Lys Asn
                485                 490                 495

Ala Thr Gly Lys Met Leu Arg Arg Ala Leu Arg Asp Ile Leu Pro Gln
            500                 505                 510


<210> SEQ ID NO 15
<211> LENGTH: 700
<212> TYPE: PRT
<213> ORGANISM: Saccharomyces cerevisiae

<400> SEQUENCE: 15

Met Val Ala Gln Tyr Thr Val Pro Val Gly Lys Ala Ala Asn Glu His
1               5                   10                  15

Glu Thr Ala Pro Arg Arg Asn Tyr Gln Cys Arg Glu Lys Pro Leu Val
            20                  25                  30

Arg Pro Pro Asn Thr Lys Cys Ser Thr Val Tyr Glu Phe Val Leu Glu
        35                  40                  45

Cys Phe Gln Lys Asn Lys Asn Ser Asn Ala Met Gly Trp Arg Asp Val
    50                  55                  60

Lys Glu Ile His Glu Glu Ser Lys Ser Val Met Lys Lys Val Asp Gly
65                  70                  75                  80

Lys Glu Thr Ser Val Glu Lys Lys Trp Met Tyr Tyr Glu Leu Ser His
                85                  90                  95

Tyr His Tyr Asn Ser Phe Asp Gln Leu Thr Asp Ile Met His Glu Ile
            100                 105                 110

Gly Arg Gly Leu Val Lys Ile Gly Leu Lys Pro Asn Asp Asp Asp Lys
        115                 120                 125

Leu His Leu Tyr Ala Ala Thr Ser His Lys Trp Met Lys Met Phe Leu
    130                 135                 140

Gly Ala Gln Ser Gln Gly Ile Pro Val Val Thr Ala Tyr Asp Thr Leu
145                 150                 155                 160

Gly Glu Lys Gly Leu Ile His Ser Leu Val Gln Thr Gly Ser Lys Ala
                165                 170                 175

Ile Phe Thr Asp Asn Ser Leu Leu Pro Ser Leu Ile Lys Pro Val Gln
            180                 185                 190

Ala Ala Gln Asp Val Lys Tyr Ile Ile His Phe Asp Ser Ile Ser Ser
        195                 200                 205

Glu Asp Arg Arg Gln Ser Gly Lys Ile Tyr Gln Ser Ala His Asp Ala
    210                 215                 220

Ile Asn Arg Ile Lys Glu Val Arg Pro Asp Ile Lys Thr Phe Ser Phe
225                 230                 235                 240

Asp Asp Ile Leu Lys Leu Gly Lys Glu Ser Cys Asn Glu Ile Asp Val
                245                 250                 255

His Pro Pro Gly Lys Asp Asp Leu Cys Cys Ile Met Tyr Thr Ser Gly
            260                 265                 270
```

-continued

Ser Thr Gly Glu Pro Lys Gly Val Val Leu Lys His Ser Asn Val Val
275 280 285

Ala Gly Val Gly Gly Ala Ser Leu Asn Val Leu Lys Phe Val Gly Asn
290 295 300

Thr Asp Arg Val Ile Cys Phe Leu Pro Leu Ala His Ile Phe Glu Leu
305 310 315 320

Val Phe Glu Leu Leu Ser Phe Tyr Trp Gly Ala Cys Ile Gly Tyr Ala
325 330 335

Thr Val Lys Thr Leu Thr Ser Ser Ser Val Arg Asn Cys Gln Gly Asp
340 345 350

Leu Gln Glu Phe Lys Pro Thr Ile Met Val Gly Val Ala Ala Val Trp
355 360 365

Glu Thr Val Arg Lys Gly Ile Leu Asn Gln Ile Asp Asn Leu Pro Phe
370 375 380

Leu Thr Lys Lys Ile Phe Trp Thr Ala Tyr Asn Thr Lys Leu Asn Met
385 390 395 400

Gln Arg Leu His Ile Pro Gly Gly Gly Ala Leu Gly Asn Leu Val Phe
405 410 415

Lys Lys Ile Arg Thr Ala Thr Gly Gly Gln Leu Arg Tyr Leu Leu Asn
420 425 430

Gly Gly Ser Pro Ile Ser Arg Asp Ala Gln Glu Phe Ile Thr Asn Leu
435 440 445

Ile Cys Pro Met Leu Ile Gly Tyr Gly Leu Thr Glu Thr Cys Ala Ser
450 455 460

Thr Thr Ile Leu Asp Pro Ala Asn Phe Glu Leu Gly Val Ala Gly Asp
465 470 475 480

Leu Thr Gly Cys Val Thr Val Lys Leu Val Asp Val Glu Glu Leu Gly
485 490 495

Tyr Phe Ala Lys Asn Asn Gln Gly Glu Val Trp Ile Thr Gly Ala Asn
500 505 510

Val Thr Pro Glu Tyr Tyr Lys Asn Glu Glu Glu Thr Ser Gln Ala Leu
515 520 525

Thr Ser Asp Gly Trp Phe Lys Thr Gly Asp Ile Gly Glu Trp Glu Ala
530 535 540

Asn Gly His Leu Lys Ile Ile Asp Arg Lys Lys Asn Leu Val Lys Thr
545 550 555 560

Met Asn Gly Glu Tyr Ile Ala Leu Glu Lys Leu Glu Ser Val Tyr Arg
565 570 575

Ser Asn Glu Tyr Val Ala Asn Ile Cys Val Tyr Ala Asp Gln Ser Lys
580 585 590

Thr Lys Pro Val Gly Ile Ile Val Pro Asn His Ala Pro Leu Thr Lys
595 600 605

Leu Ala Lys Lys Leu Gly Ile Met Glu Gln Lys Asp Ser Ser Ile Asn
610 615 620

Ile Glu Asn Tyr Leu Glu Asp Ala Lys Leu Ile Lys Ala Val Tyr Ser
625 630 635 640

Asp Leu Leu Lys Thr Gly Lys Asp Gln Gly Leu Val Gly Ile Glu Leu
645 650 655

Leu Ala Gly Ile Val Phe Phe Asp Gly Glu Trp Thr Pro Gln Asn Gly
660 665 670

Phe Val Thr Ser Ala Gln Lys Leu Lys Arg Lys Asp Ile Leu Asn Ala
675 680 685

```
Val Lys Asp Lys Val Asp Ala Val Tyr Ser Ser Ser
    690                 695                 700


<210> SEQ ID NO 16
<211> LENGTH: 362
<212> TYPE: PRT
<213> ORGANISM: Umbellularia californica

<400> SEQUENCE: 16

Met Leu Lys Leu Ser Cys Asn Val Thr Asp Ser Lys Leu Gln Arg Ser
1               5                   10                  15

Leu Leu Phe Phe Ser His Ser Tyr Arg Ser Asp Pro Val Asn Phe Ile
            20                  25                  30

Arg Arg Arg Ile Val Ser Cys Ser Gln Thr Lys Lys Thr Gly Leu Val
        35                  40                  45

Pro Leu Arg Ala Val Val Ser Ala Asp Gln Gly Ser Val Val Gln Gly
    50                  55                  60

Leu Ala Thr Leu Ala Asp Gln Leu Arg Leu Gly Ser Leu Thr Glu Asp
65                  70                  75                  80

Gly Leu Ser Tyr Lys Glu Lys Phe Val Val Arg Ser Tyr Glu Val Gly
                85                  90                  95

Ser Asn Lys Thr Ala Thr Val Glu Thr Ile Ala Asn Leu Leu Gln Glu
            100                 105                 110

Val Gly Cys Asn His Ala Gln Ser Val Gly Phe Ser Thr Asp Gly Phe
        115                 120                 125

Ala Thr Thr Thr Thr Met Arg Lys Leu His Leu Ile Trp Val Thr Ala
    130                 135                 140

Arg Met His Ile Glu Ile Tyr Lys Tyr Pro Ala Trp Gly Asp Val Val
145                 150                 155                 160

Glu Ile Glu Thr Trp Cys Gln Ser Glu Gly Arg Ile Gly Thr Arg Arg
                165                 170                 175

Asp Trp Ile Leu Lys Asp Ser Val Thr Gly Glu Val Thr Gly Arg Ala
            180                 185                 190

Thr Ser Lys Trp Val Met Met Asn Gln Asp Thr Arg Arg Leu Gln Lys
        195                 200                 205

Val Ser Asp Asp Val Arg Asp Glu Tyr Leu Val Phe Cys Pro Gln Glu
    210                 215                 220

Pro Arg Leu Ala Phe Pro Glu Glu Asn Asn Arg Ser Leu Lys Lys Ile
225                 230                 235                 240

Pro Lys Leu Glu Asp Pro Ala Gln Tyr Ser Met Ile Gly Leu Lys Pro
                245                 250                 255

Arg Arg Ala Asp Leu Asp Met Asn Gln His Val Asn Asn Val Thr Tyr
            260                 265                 270

Ile Gly Trp Val Leu Glu Ser Ile Pro Gln Glu Ile Val Asp Thr His
        275                 280                 285

Glu Leu Gln Val Ile Thr Leu Asp Tyr Arg Arg Glu Cys Gln Gln Asp
    290                 295                 300

Asp Val Val Asp Ser Leu Thr Thr Thr Thr Ser Glu Ile Gly Gly Thr
305                 310                 315                 320

Asn Gly Ser Ala Thr Ser Gly Thr Gln Gly His Asn Asp Ser Gln Phe
                325                 330                 335

Leu His Leu Leu Arg Leu Ser Gly Asp Gly Gln Glu Ile Asn Arg Gly
            340                 345                 350

Thr Thr Leu Trp Arg Lys Lys Pro Ser Ser
        355                 360
```

<210> SEQ ID NO 17
<211> LENGTH: 382
<212> TYPE: PRT
<213> ORGANISM: Cinnamomum camphora

<400> SEQUENCE: 17

```
Met Ala Thr Thr Ser Leu Ala Ser Ala Phe Cys Ser Met Lys Ala Val
1               5                   10                  15

Met Leu Ala Arg Asp Gly Arg Gly Met Lys Pro Arg Ser Ser Asp Leu
            20                  25                  30

Gln Leu Arg Ala Gly Asn Ala Gln Thr Ser Leu Lys Met Ile Asn Gly
        35                  40                  45

Thr Lys Phe Ser Tyr Thr Glu Ser Leu Lys Lys Leu Pro Asp Trp Ser
    50                  55                  60

Met Leu Phe Ala Val Ile Thr Thr Ile Phe Ser Ala Ala Glu Lys Gln
65                  70                  75                  80

Trp Thr Asn Leu Glu Trp Lys Pro Lys Pro Asn Pro Pro Gln Leu Leu
                85                  90                  95

Asp Asp His Phe Gly Pro His Gly Leu Val Phe Arg Arg Thr Phe Ala
            100                 105                 110

Ile Arg Ser Tyr Glu Val Gly Pro Asp Arg Ser Thr Ser Ile Val Ala
        115                 120                 125

Val Met Asn His Leu Gln Glu Ala Ala Leu Asn His Ala Lys Ser Val
    130                 135                 140

Gly Ile Leu Gly Asp Gly Phe Gly Thr Thr Leu Glu Met Ser Lys Arg
145                 150                 155                 160

Asp Leu Ile Trp Val Val Lys Arg Thr His Val Ala Val Glu Arg Tyr
                165                 170                 175

Pro Ala Trp Gly Asp Thr Val Glu Val Glu Cys Trp Val Gly Ala Ser
            180                 185                 190

Gly Asn Asn Gly Arg Arg His Asp Phe Leu Val Arg Asp Cys Lys Thr
        195                 200                 205

Gly Glu Ile Leu Thr Arg Cys Thr Ser Leu Ser Val Met Met Asn Thr
    210                 215                 220

Arg Thr Arg Arg Leu Ser Lys Ile Pro Glu Glu Val Arg Gly Glu Ile
225                 230                 235                 240

Gly Pro Ala Phe Ile Asp Asn Val Ala Val Lys Asp Glu Glu Ile Lys
                245                 250                 255

Lys Pro Gln Lys Leu Asn Asp Ser Thr Ala Asp Tyr Ile Gln Gly Gly
            260                 265                 270

Leu Thr Pro Arg Trp Asn Asp Leu Asp Ile Asn Gln His Val Asn Asn
        275                 280                 285

Ile Lys Tyr Val Asp Trp Ile Leu Glu Thr Val Pro Asp Ser Ile Phe
    290                 295                 300

Glu Ser His His Ile Ser Ser Phe Thr Ile Glu Tyr Arg Arg Glu Cys
305                 310                 315                 320

Thr Met Asp Ser Val Leu Gln Ser Leu Thr Thr Val Ser Gly Gly Ser
                325                 330                 335

Ser Glu Ala Gly Leu Val Cys Glu His Leu Leu Gln Leu Glu Gly Gly
            340                 345                 350

Ser Glu Val Leu Arg Ala Lys Thr Glu Trp Arg Pro Lys Leu Thr Asp
        355                 360                 365

Ser Phe Arg Gly Ile Ser Val Ile Pro Ala Glu Ser Ser Val
```

-continued 370 375 380

<210> SEQ ID NO 18
<211> LENGTH: 419
<212> TYPE: PRT
<213> ORGANISM: Ricinus communis

<400> SEQUENCE: 18

Met Val Ala Thr Ala Ala Ala Ala Thr Ser Ser Phe Phe Pro Val Pro
1 5 10 15

Ser Gln Ser Ala Asp Ala Asn Phe Asp Lys Ala Pro Ala Ser Leu Gly
20 25 30

Gly Ile Lys Leu Lys Ser Thr Ser Cys Ser Arg Gly Leu Gln Val Lys
35 40 45

Ala Asn Ala Gln Ala Pro Pro Lys Ile Asn Gly Ser Ser Val Gly Phe
50 55 60

Thr Thr Ser Val Glu Thr Val Lys Asn Asp Gly Asp Met Pro Leu Pro
65 70 75 80

Pro Pro Pro Arg Thr Phe Ile Asn Gln Leu Pro Asp Trp Ser Met Leu
85 90 95

Leu Ala Ala Ile Thr Thr Ile Phe Leu Ala Ala Glu Lys Gln Trp Met
100 105 110

Met Leu Asp Trp Lys Pro Arg Arg Pro Asp Met Leu Ile Asp Pro Phe
115 120 125

Gly Ile Gly Arg Ile Val Gln Asp Gly Leu Ile Phe Arg Gln Asn Phe
130 135 140

Ser Ile Arg Ser Tyr Glu Ile Gly Ala Asp Arg Thr Ala Ser Ile Glu
145 150 155 160

Thr Leu Met Asn His Leu Gln Glu Thr Ala Leu Asn His Val Lys Thr
165 170 175

Ala Gly Leu Leu Gly Asp Gly Phe Gly Ser Thr Pro Glu Met Ser Lys
180 185 190

Arg Asn Leu Ile Trp Val Val Thr Arg Met Gln Val Leu Val Asp Arg
195 200 205

Tyr Pro Thr Trp Gly Asp Val Val Gln Val Asp Thr Trp Val Ser Lys
210 215 220

Ser Gly Lys Asn Gly Met Arg Arg Asp Trp Cys Val Arg Asp Ser Arg
225 230 235 240

Thr Gly Glu Thr Leu Thr Arg Ala Ser Ser Val Trp Val Met Met Asn
245 250 255

Lys Leu Thr Arg Arg Leu Ser Lys Ile Pro Glu Glu Val Arg Gly Glu
260 265 270

Ile Glu Pro Tyr Phe Leu Asn Ser Asp Pro Ile Val Asp Glu Asp Ser
275 280 285

Arg Lys Leu Pro Lys Leu Asp Asp Ser Asn Ala Asp Tyr Val Arg Lys
290 295 300

Gly Leu Thr Pro Arg Trp Ser Asp Leu Asp Ile Asn Gln His Val Asn
305 310 315 320

Asn Val Lys Tyr Ile Gly Trp Ile Leu Glu Ser Ala Pro Leu Pro Ile
325 330 335

Leu Glu Ser His Glu Leu Ser Ala Ile Thr Leu Glu Tyr Arg Arg Glu
340 345 350

Cys Gly Arg Asp Ser Val Leu Gln Ser Leu Thr Ala Val Ser Gly Asn
355 360 365

```
Gly Ile Gly Asn Leu Gly Asn Ala Gly Asp Ile Glu Cys Gln His Leu
    370                 375                 380

Leu Arg Leu Glu Asp Gly Ala Glu Ile Val Arg Gly Arg Thr Glu Trp
385                 390                 395                 400

Arg Pro Lys Tyr Ser Ser Asn Phe Gly Ile Met Gly Gln Ile Pro Val
                405                 410                 415

Glu Ser Ala


<210> SEQ ID NO 19
<211> LENGTH: 415
<212> TYPE: PRT
<213> ORGANISM: Cuphea hookeriana

<400> SEQUENCE: 19

Met Val Ala Ala Ala Ala Ser Ser Ala Phe Phe Pro Val Pro Ala Pro
1               5                   10                  15

Gly Ala Ser Pro Lys Pro Gly Lys Phe Gly Asn Trp Pro Ser Ser Leu
            20                  25                  30

Ser Pro Ser Phe Lys Pro Lys Ser Ile Pro Asn Gly Gly Phe Gln Val
        35                  40                  45

Lys Ala Asn Asp Ser Ala His Pro Lys Ala Asn Gly Ser Ala Val Ser
    50                  55                  60

Leu Lys Ser Gly Ser Leu Asn Thr Gln Glu Asp Thr Ser Ser Ser Pro
65                  70                  75                  80

Pro Pro Arg Thr Phe Leu His Gln Leu Pro Asp Trp Ser Arg Leu Leu
                85                  90                  95

Thr Ala Ile Thr Thr Val Phe Val Lys Ser Lys Arg Pro Asp Met His
            100                 105                 110

Asp Arg Lys Ser Lys Arg Pro Asp Met Leu Val Asp Ser Phe Gly Leu
        115                 120                 125

Glu Ser Thr Val Gln Asp Gly Leu Val Phe Arg Gln Ser Phe Ser Ile
    130                 135                 140

Arg Ser Tyr Glu Ile Gly Thr Asp Arg Thr Ala Ser Ile Glu Thr Leu
145                 150                 155                 160

Met Asn His Leu Gln Glu Thr Ser Leu Asn His Cys Lys Ser Thr Gly
                165                 170                 175

Ile Leu Leu Asp Gly Phe Gly Arg Thr Leu Glu Met Cys Lys Arg Asp
            180                 185                 190

Leu Ile Trp Val Val Ile Lys Met Gln Ile Lys Val Asn Arg Tyr Pro
        195                 200                 205

Ala Trp Gly Asp Thr Val Glu Ile Asn Thr Arg Phe Ser Arg Leu Gly
    210                 215                 220

Lys Ile Gly Met Gly Arg Asp Trp Leu Ile Ser Asp Cys Asn Thr Gly
225                 230                 235                 240

Glu Ile Leu Val Arg Ala Thr Ser Ala Tyr Ala Met Met Asn Gln Lys
                245                 250                 255

Thr Arg Arg Leu Ser Lys Leu Pro Tyr Glu Val His Gln Glu Ile Val
            260                 265                 270

Pro Leu Phe Val Asp Ser Pro Val Ile Glu Asp Ser Asp Leu Lys Val
        275                 280                 285

His Lys Phe Lys Val Lys Thr Gly Asp Ser Ile Gln Lys Gly Leu Thr
    290                 295                 300

Pro Gly Trp Asn Asp Leu Asp Val Asn Gln His Val Ser Asn Val Lys
305                 310                 315                 320
```

-continued

```
Tyr Ile Gly Trp Ile Leu Glu Ser Met Pro Thr Glu Val Leu Glu Thr
                325                 330                 335

Gln Glu Leu Cys Ser Leu Ala Leu Glu Tyr Arg Arg Glu Cys Gly Arg
            340                 345                 350

Asp Ser Val Leu Glu Ser Val Thr Ala Met Asp Pro Ser Lys Val Gly
        355                 360                 365

Val Arg Ser Gln Tyr Gln His Leu Leu Arg Leu Glu Asp Gly Thr Ala
    370                 375                 380

Ile Val Asn Gly Ala Thr Glu Trp Arg Pro Lys Asn Ala Gly Ala Asn
385                 390                 395                 400

Gly Ala Ile Ser Thr Gly Lys Thr Ser Asn Gly Asn Ser Val Ser
                405                 410                 415


<210> SEQ ID NO 20
<211> LENGTH: 411
<212> TYPE: PRT
<213> ORGANISM: Cuphea palustris

<400> SEQUENCE: 20

Met Val Ala Ala Ala Ala Ser Ala Ala Phe Phe Ser Val Ala Thr Pro
1               5                   10                  15

Arg Thr Asn Ile Ser Pro Ser Ser Leu Ser Val Pro Phe Lys Pro Lys
            20                  25                  30

Ser Asn His Asn Gly Gly Phe Gln Val Lys Ala Asn Ala Ser Ala His
        35                  40                  45

Pro Lys Ala Asn Gly Ser Ala Val Ser Leu Lys Ser Gly Ser Leu Glu
    50                  55                  60

Thr Gln Glu Asp Lys Thr Ser Ser Ser Ser Pro Pro Pro Arg Thr Phe
65                  70                  75                  80

Ile Asn Gln Leu Pro Val Trp Ser Met Leu Leu Ser Ala Val Thr Thr
                85                  90                  95

Val Phe Gly Val Ala Glu Lys Gln Trp Pro Met Leu Asp Arg Lys Ser
            100                 105                 110

Lys Arg Pro Asp Met Leu Val Glu Pro Leu Gly Val Asp Arg Ile Val
        115                 120                 125

Tyr Asp Gly Val Ser Phe Arg Gln Ser Phe Ser Ile Arg Ser Tyr Glu
    130                 135                 140

Ile Gly Ala Asp Arg Thr Ala Ser Ile Glu Thr Leu Met Asn Met Phe
145                 150                 155                 160

Gln Glu Thr Ser Leu Asn His Cys Lys Ile Ile Gly Leu Leu Asn Asp
                165                 170                 175

Gly Phe Gly Arg Thr Pro Glu Met Cys Lys Arg Asp Leu Ile Trp Val
            180                 185                 190

Val Thr Lys Met Gln Ile Glu Val Asn Arg Tyr Pro Thr Trp Gly Asp
        195                 200                 205

Thr Ile Glu Val Asn Thr Trp Val Ser Ala Ser Gly Lys His Gly Met
    210                 215                 220

Gly Arg Asp Trp Leu Ile Ser Asp Cys His Thr Gly Glu Ile Leu Ile
225                 230                 235                 240

Arg Ala Thr Ser Val Trp Ala Met Met Asn Gln Lys Thr Arg Arg Leu
                245                 250                 255

Ser Lys Ile Pro Tyr Glu Val Arg Gln Glu Ile Glu Pro Gln Phe Val
            260                 265                 270

Asp Ser Ala Pro Val Ile Val Asp Asp Arg Lys Phe His Lys Leu Asp
        275                 280                 285
```

-continued

```
Leu Lys Thr Gly Asp Ser Ile Cys Asn Gly Leu Thr Pro Arg Trp Thr
    290                 295                 300

Asp Leu Asp Val Asn Gln His Val Asn Asn Val Lys Tyr Ile Gly Trp
305                 310                 315                 320

Ile Leu Gln Ser Val Pro Thr Glu Val Phe Glu Thr Gln Glu Leu Cys
                325                 330                 335

Gly Leu Thr Leu Glu Tyr Arg Arg Glu Cys Gly Arg Asp Ser Val Leu
            340                 345                 350

Glu Ser Val Thr Ala Met Asp Pro Ser Lys Glu Gly Asp Arg Ser Leu
        355                 360                 365

Tyr Gln His Leu Leu Arg Leu Glu Asp Gly Ala Asp Ile Val Lys Gly
    370                 375                 380

Arg Thr Glu Trp Arg Pro Lys Asn Ala Gly Ala Lys Gly Ala Ile Leu
385                 390                 395                 400

Thr Gly Lys Thr Ser Asn Gly Asn Ser Ile Ser
                405                 410


<210> SEQ ID NO 21
<211> LENGTH: 419
<212> TYPE: PRT
<213> ORGANISM: Cuphea lanceolata

<400> SEQUENCE: 21

Met Val Ala Ala Ala Ala Thr Ser Ala Phe Phe Pro Val Pro Ala Pro
1               5                   10                  15

Gly Thr Ser Pro Lys Pro Gly Lys Ser Gly Asn Trp Pro Ser Ser Leu
            20                  25                  30

Ser Pro Thr Phe Lys Pro Lys Ser Ile Pro Asn Ala Gly Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Ser Ile Val Arg Asp Gly Leu Val Ser Arg Gln Ser Phe Leu
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Thr Trp Gly Asp Thr Val Glu Ile Asn Thr Trp Phe Ser Gln Ser
    210                 215                 220

Gly Lys Ile Gly Met Ala Ser Asp Trp Leu Ile Ser Asp Cys Asn Thr
225                 230                 235                 240

Gly Glu Ile Leu Ile Arg Ala Thr Ser Val Trp Ala Met Met Asn Gln
```

-continued

```
                245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Gln
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Thr Gln Glu Leu Cys Ser Leu Thr Val Glu Tyr Arg Arg Glu Cys
            340                 345                 350

Gly Met Asp Ser Val Leu Glu Ser Val Thr Ala Val Asp Pro Ser Glu
        355                 360                 365

Asn Gly Gly Arg Ser Gln Tyr Lys His Leu Leu Arg Leu Glu Asp Gly
    370                 375                 380

Thr Asp Ile Val Lys Ser Arg Thr Glu Trp Arg Pro Lys Asn Ala Gly
385                 390                 395                 400

Thr Asn Gly Ala Ile Ser Thr Ser Thr Ala Lys Thr Ser Asn Gly Asn
                405                 410                 415

Ser Ala Ser


<210> SEQ ID NO 22
<211> LENGTH: 362
<212> TYPE: PRT
<213> ORGANISM: Arabidopsis thaliana

<400> SEQUENCE: 22

Met Leu Lys Leu Ser Cys Asn Val Thr Asp Ser Lys Leu Gln Arg Ser
1               5                   10                  15

Leu Leu Phe Phe Ser His Ser Tyr Arg Ser Asp Pro Val Asn Phe Ile
            20                  25                  30

Arg Arg Arg Ile Val Ser Cys Ser Gln Thr Lys Lys Thr Gly Leu Val
        35                  40                  45

Pro Leu Arg Ala Val Val Ser Ala Asp Gln Gly Ser Val Val Gln Gly
    50                  55                  60

Leu Ala Thr Leu Ala Asp Gln Leu Arg Leu Gly Ser Leu Thr Glu Asp
65                  70                  75                  80

Gly Leu Ser Tyr Lys Glu Lys Phe Val Val Arg Ser Tyr Glu Val Gly
                85                  90                  95

Ser Asn Lys Thr Ala Thr Val Glu Thr Ile Ala Asn Leu Leu Gln Glu
            100                 105                 110

Val Gly Cys Asn His Ala Gln Ser Val Gly Phe Ser Thr Asp Gly Phe
        115                 120                 125

Ala Thr Thr Thr Thr Met Arg Lys Leu His Leu Ile Trp Val Thr Ala
    130                 135                 140

Arg Met His Ile Glu Ile Tyr Lys Tyr Pro Ala Trp Gly Asp Val Val
145                 150                 155                 160

Glu Ile Glu Thr Trp Cys Gln Ser Glu Gly Arg Ile Gly Thr Arg Arg
                165                 170                 175

Asp Trp Ile Leu Lys Asp Ser Val Thr Gly Glu Val Thr Gly Arg Ala
            180                 185                 190

Thr Ser Lys Trp Val Met Met Asn Gln Asp Thr Arg Arg Leu Gln Lys
```

```
        195                 200                 205

Val Ser Asp Asp Val Arg Asp Glu Tyr Leu Val Phe Cys Pro Gln Glu
    210                 215                 220

Pro Arg Leu Ala Phe Pro Glu Glu Asn Asn Arg Ser Leu Lys Lys Ile
225                 230                 235                 240

Pro Lys Leu Glu Asp Pro Ala Gln Tyr Ser Met Ile Gly Leu Lys Pro
                245                 250                 255

Arg Arg Ala Asp Leu Asp Met Asn Gln His Val Asn Asn Val Thr Tyr
            260                 265                 270

Ile Gly Trp Val Leu Glu Ser Ile Pro Gln Glu Ile Val Asp Thr His
        275                 280                 285

Glu Leu Gln Val Ile Thr Leu Asp Tyr Arg Arg Glu Cys Gln Gln Asp
    290                 295                 300

Asp Val Val Asp Ser Leu Thr Thr Thr Thr Ser Glu Ile Gly Gly Thr
305                 310                 315                 320

Asn Gly Ser Ala Thr Ser Gly Thr Gln Gly His Asn Asp Ser Gln Phe
                325                 330                 335

Leu His Leu Leu Arg Leu Ser Gly Asp Gly Gln Glu Ile Asn Arg Gly
            340                 345                 350

Thr Thr Leu Trp Arg Lys Lys Pro Ser Ser
        355                 360


<210> SEQ ID NO 23
<211> LENGTH: 365
<212> TYPE: PRT
<213> ORGANISM: Helianthus annuus

<400> SEQUENCE: 23

Met Leu Ser Arg Gly Val Pro Thr Ala Thr Ala Thr Ala Tyr Asn Asp
1               5                   10                  15

Val Ile Lys Glu Thr Ala Arg Ser Val Thr Asn Ser Arg Ser Ile Asp
            20                  25                  30

Ser Val Ser Ile Arg Arg Arg Asn Asn Gly Phe Val Ser Asn Ser Leu
        35                  40                  45

Cys Arg Arg Val Ala Pro Val Met Ala Val Lys Val Asp Glu Gln Arg
    50                  55                  60

Thr Gly Val Ala Val Asp Val Thr Glu Lys Arg Leu Ala Asp Arg Leu
65                  70                  75                  80

Arg Met Gly Ser Leu Thr Glu Asp Gly Leu Ser Tyr Lys Glu Arg Phe
                85                  90                  95

Ile Ile Arg Cys Tyr Glu Val Gly Ile Asn Lys Thr Ala Thr Val Glu
            100                 105                 110

Thr Ile Ala Asn Leu Leu Gln Glu Val Gly Gly Asn His Ala Gln Ser
        115                 120                 125

Val Gly Phe Ser Thr Asp Gly Phe Ala Thr Thr Thr Thr Met Arg Lys
    130                 135                 140

Leu Asn Leu Ile Trp Val Thr Ser Arg Met His Ile Glu Ile Tyr Arg
145                 150                 155                 160

Tyr Pro Ala Trp Ser Asp Val Val Glu Ile Glu Thr Trp Cys Gln Gly
                165                 170                 175

Glu Gly Arg Ile Gly Thr Arg Arg Asp Trp Ile Ile Lys Asp His Ala
            180                 185                 190

Asn Gly Glu Val Ile Gly Arg Ala Thr Ser Lys Trp Val Met Met Asn
        195                 200                 205
```

-continued

```
Ser Glu Thr Arg Arg Leu Gln Lys Val Asn Asp Asp Ile Arg Asp Glu
    210                 215                 220

Tyr Leu Ile Phe Cys Pro Lys Thr Leu Arg Leu Ala Phe Pro Glu Glu
225                 230                 235                 240

Asn Asn Asn Ser Leu Lys Lys Ile Ala Lys Leu Glu Asp Pro Ala Glu
                245                 250                 255

Cys Ser Thr Leu Gly Leu Val Pro Arg Arg Ala Asp Leu Asp Met Asn
            260                 265                 270

Lys His Val Asn Asn Val Thr Tyr Ile Gly Trp Val Leu Glu Ser Ile
        275                 280                 285

Pro Gln Glu Val Ile Asp Thr His Glu Leu Gln Thr Ile Thr Leu Asp
    290                 295                 300

Tyr Arg Arg Glu Cys Gln His Asp Asp Val Val Asp Ser Leu Thr Ser
305                 310                 315                 320

Ser Glu Ser Pro Ala Val Asn Gly Cys Ala Ser Gly Glu Asn Leu Ser
                325                 330                 335

Lys Phe Leu His Leu Leu Arg Ser Ser Gly Glu Gly Leu Glu Leu Asn
            340                 345                 350

Arg Gly Arg Thr Glu Trp Arg Lys Lys Pro Ala Lys Lys
        355                 360                 365


<210> SEQ ID NO 24
<211> LENGTH: 381
<212> TYPE: PRT
<213> ORGANISM: Macadamia tetraphylla

<400> SEQUENCE: 24

Met Leu Ser Val Lys Gly Cys Asn Ala Pro Asp Gln Leu Arg Ser Leu
1               5                   10                  15

Thr Gln Cys Leu Ser Val Thr Pro Pro Lys Ala Leu Thr Arg Arg Gly
            20                  25                  30

Ile Ala Val Val Ser Cys Cys Ser Ser Ser Ser Thr Ser Pro Ser Ser
        35                  40                  45

Ile Ser Ala Ser Arg Val Ser Asn Leu Val Val Ser Glu Arg Thr Asn
    50                  55                  60

Gly Ser Gly Gly Val Val Ser Asn Pro Ser Ser Asn Gly Ser Ala Ser
65                  70                  75                  80

Leu Leu Glu Glu Leu Arg Leu Gly Ser Leu Ala Glu Asp Gly Leu Ser
                85                  90                  95

Tyr Lys Glu Lys Phe Ile Val Arg Ser Tyr Glu Val Gly Ile Asn Lys
            100                 105                 110

Thr Ala Thr Met Glu Ala Ile Ala Asn Leu Leu Gln Glu Ala Ala Cys
        115                 120                 125

Asn Gln Val Gln Thr Leu Gly Tyr Ser Thr Asp Gly Met Gly Thr Ser
    130                 135                 140

Tyr Thr Met Arg Gln Leu His Leu Ile Trp Val Thr Ala Arg Met His
145                 150                 155                 160

Ile Glu Val Tyr Lys Tyr Pro Ala Trp Gly Asp Met Ile Glu Ile Glu
                165                 170                 175

Thr Trp Phe Glu Ala Gly Arg Val Gly Thr Arg Arg Asp Phe Val Val
            180                 185                 190

Lys Asp Ala Thr Gly Thr Val Ile Gly Arg Ala Thr Ser Lys Trp Val
        195                 200                 205

Ala Met Asn Gln Asp Thr Arg Arg Leu Gln Lys Val Asn Asp Lys Ile
    210                 215                 220
```

```
Leu Glu Glu Ile Met Ser His Ala Pro Arg Thr Pro Arg Leu Ala Phe
225                 230                 235                 240

Pro Glu Glu Asp Asn Cys Ser Leu Lys Lys Ile Pro Lys Leu Glu Glu
                245                 250                 255

Pro Ala Gln Tyr Ser Lys Leu Gly Leu Lys Ala Arg Arg Ala Asp Leu
            260                 265                 270

Asp Met Asn Gln His Val Asn Asn Val Thr Tyr Ile Gly Trp Leu Leu
        275                 280                 285

Glu Ser Leu Pro Gln Glu Ile Ile Asp Thr His Glu Leu Arg Lys Val
    290                 295                 300

Thr Leu Asp Tyr Arg Arg Glu Cys Gln His Asp Asp Thr Val Asp Ser
305                 310                 315                 320

Leu Thr Ser Met Glu Leu Met Asp Asn Ala Glu Ala Ile Pro Glu Leu
                325                 330                 335

Asn Gly Thr Asn Gly Ser Ala Thr Glu Arg Lys His Glu Glu Asp Cys
            340                 345                 350

Cys Arg Phe Leu His Phe Val Arg Phe Ser Gly Asp Gly Pro Glu Val
        355                 360                 365

Asn Arg Gly Arg Thr Glu Trp Arg Arg Lys Ser Thr Arg
    370                 375                 380


<210> SEQ ID NO 25
<211> LENGTH: 1050
<212> TYPE: PRT
<213> ORGANISM: Aspergillus terreus

<400> SEQUENCE: 25

Met Ile Lys Glu Thr Glu Gln Ile Pro Gly Pro Arg Pro Leu Pro Val
1               5                   10                  15

Val Gly Asn Leu Phe Asp Met Asp Leu Glu His Gly Leu Glu Cys Leu
            20                  25                  30

Ile Arg Leu Ala Asp Asp Phe Gly Pro Leu Phe Gln Ile Thr Ile Asn
        35                  40                  45

Gly Glu Lys Gln Ile Phe Ala Thr Ser Gln Ala Leu Val Asp Glu Leu
    50                  55                  60

Cys Asp Glu Ser Arg Phe His Lys Ala Val Met Gly Gly Leu Glu Lys
65                  70                  75                  80

Leu Arg Met Leu Ala Ser Asp Gly Leu Phe Thr Ala Tyr His Gly Glu
                85                  90                  95

Arg Gly Trp Gly Ile Ala His Arg Ile Leu Val Pro Ala Phe Gly Pro
            100                 105                 110

Leu Arg Ile Arg Asn Met Phe Glu Glu Met Asn Asp Val Ala Gln Gln
        115                 120                 125

Leu Cys Leu Lys Trp Ala Arg Gln Gly Ser Ser Thr Ser Ile Asn Ile
    130                 135                 140

Thr Asp Asp Phe Thr Arg Leu Thr Leu Asp Thr Ile Ala Leu Cys Thr
145                 150                 155                 160

Met Asn Phe Arg Leu Asn Ser Phe Tyr Asn Asn Glu Thr Met His Pro
                165                 170                 175

Phe Val Lys Ser Met Leu Tyr Val Leu Arg Glu Ser Asp Ile Gln Ser
            180                 185                 190

Met Leu Pro Gly Ile Ala Asn Cys Ile Arg Val Lys Ala Arg Ser Arg
        195                 200                 205

Met Ser Lys His Ile Gln Leu Met Arg Asn Met Ala Arg Gly Ile Ile
```

-continued

```
    210                 215                 220

Gln Glu Arg Arg Asp Gln Ala Glu Pro Val Asp Asp Leu Leu Asn Thr
225                 230                 235                 240

Leu Leu Asn Gly Arg Asp Pro Val Thr Gly Glu Gly Met Ser Asp Asp
                245                 250                 255

Leu Ile Ile Asn Asn Val Ile Thr Phe Leu Ile Ala Gly His Glu Thr
            260                 265                 270

Thr Ser Gly Leu Leu Ser Phe Thr Phe Tyr Tyr Leu Leu Gln Asn Pro
        275                 280                 285

His Ile Leu Glu Arg Ala Gln Asn Glu Val Asp Glu Val Thr Gly Gly
    290                 295                 300

Glu Arg Ile Thr Val Gln His Leu Gly Arg Leu Thr Tyr Ile Asp Ala
305                 310                 315                 320

Ile Leu Lys Glu Ser Leu Arg Leu Met Pro Thr Ala Pro Ala Phe Thr
                325                 330                 335

Val Thr Pro Lys Lys Pro Glu Val Leu Gly Gly Ala Trp Ala Ile Asp
            340                 345                 350

Ala Gly Gln Ala Val Asn Val Leu Leu Pro Val Cys Leu Arg Asp Arg
        355                 360                 365

Ser Val Phe Gly Pro Asp Ala Asp Glu Phe Arg Pro Glu Arg Met Leu
    370                 375                 380

Glu Glu Asn Phe Ser Lys Leu Pro Pro Asn Ser Trp Lys Pro Phe Gly
385                 390                 395                 400

Asn Gly Glu Arg Ser Cys Ile Gly Arg Ala Phe Ala Trp Gln Glu Ala
                405                 410                 415

Gln Leu Val Val Ala Met Val Leu Gln Thr Phe Asp Leu Val Pro Asp
            420                 425                 430

Asp Pro Ser Tyr Lys Leu Arg Ile Lys Glu Thr Leu Thr Ile Lys Pro
        435                 440                 445

Asp Gly Phe Arg Val Arg Ala Thr Leu Arg Arg Gly Gln Ser Ala Thr
    450                 455                 460

Gly Leu Ser Gln Gly Ser Met Ser Ala Ser Gly Ala Thr Ser Ser Val
465                 470                 475                 480

Ala Ser Pro Gly Pro Pro Ala Ala Thr Gly Ala Gln Ser Asn Pro Ala
                485                 490                 495

Gly Gly Gln Arg Ile Ser Phe Phe Tyr Gly Ser Asn Ser Gly Thr Cys
            500                 505                 510

Lys Ala Leu Ala His Arg Leu Ala Ser Ser Leu Met Gly Arg Gly Phe
        515                 520                 525

Thr Glu Gln Lys Leu Ala Ala Leu Asp Thr Val Val Gly Asn Leu Pro
    530                 535                 540

Thr Asp Gln Pro Val Ile Ile Val Thr Thr Ser Tyr Asp Gly Arg Pro
545                 550                 555                 560

Thr Asp Asp Ala Glu Glu Phe Val Arg Trp Leu Glu Ser Lys Arg Pro
                565                 570                 575

Val Leu Gln Gly Val Ser Tyr Ala Val Phe Gly Cys Gly His His Asp
            580                 585                 590

Trp Ala Lys Thr Phe Tyr Arg Ile Pro Ile Leu Ile Asp Asp Leu Met
        595                 600                 605

His Lys Ala Gly Ala Thr Arg Leu Thr Ala Leu Gly Thr Ala Asn Ala
    610                 615                 620

Ala Val Ser Asp Leu Phe Ser Asp Leu Glu Leu Trp Glu Glu Thr Asn
625                 630                 635                 640
```

-continued

```
Leu Leu Pro Ala Leu Arg Glu Ala Phe Pro Pro Ser Asn Ser Ser Asp
                645                 650                 655

Val Glu Ser Ser Glu Pro His Gln Leu Gln Ile Cys Val Ser Lys Pro
            660                 665                 670

Arg Arg Val Asp Met His Arg Gly Leu Val Glu Ala Lys Val Thr Ala
        675                 680                 685

Val Arg Thr Leu Thr Ser Pro Asp Ser Pro Glu Lys Arg His Val Glu
    690                 695                 700

Phe His Val Gln Gly Asp Thr Thr Trp Arg Pro Gly Asp His Val Asn
705                 710                 715                 720

Ile Leu Pro Val Asn Pro Leu Ser Thr Val Ser Arg Val Leu Ala Tyr
                725                 730                 735

Phe Gln Leu Ala Pro Asp His Ser Ile Thr Val Asn Ser Phe Asn Thr
            740                 745                 750

Gln Gly Leu Pro Ser Ala Thr Pro Val Ser Ala Thr Glu Leu Phe Ser
        755                 760                 765

Ser Phe Val Glu Leu Ser Gln Pro Ala Thr Arg Lys Asn Leu Lys Ala
    770                 775                 780

Leu Ala Met Ala Ala Glu Ser Lys Thr Asp Glu Gln Glu Leu Ile Arg
785                 790                 795                 800

Leu His Asp Ser Tyr Asp Ala Leu Val Arg Asp Lys Arg Val Ser Val
                805                 810                 815

Leu Asp Ile Leu Glu Arg Phe Pro Ser Ile Ser Leu Pro Ile Gly Ile
            820                 825                 830

Phe Ile Ser Met Leu Pro Pro Leu Arg Leu Arg Thr Tyr Ser Leu Ser
        835                 840                 845

Met Ala Pro Ser Phe Lys Pro Ser His Gly Ser Leu Thr Phe Ser Val
    850                 855                 860

Ile Asn Glu Pro Ala Trp Ser Gly Asn Gly Gln Tyr Leu Gly Val Gly
865                 870                 875                 880

Ser Asn Tyr Leu Ala Ser Leu Thr Pro Gly Ser Leu Leu Tyr Leu Ser
                885                 890                 895

Pro Arg Pro Ala Lys Asp Ala Phe His Leu Pro Ala Asp Gln Phe Asn
            900                 905                 910

Thr Pro Ile Ile Met Ile Cys Ala Gly Ser Gly Leu Ala Pro Phe Met
        915                 920                 925

Gly Phe Ile Gln Glu Arg Met Thr Trp Leu Lys Gln Gly Arg Pro Leu
    930                 935                 940

Ala Lys Gly Leu Leu Phe Phe Gly Cys Arg Gly Pro His Leu Asp Asp
945                 950                 955                 960

Leu Tyr Tyr Glu Glu Leu Ser Glu Phe Glu Asp Ala Gly Val Val Glu
                965                 970                 975

Val His Arg Ala Tyr Ser Arg Ala Pro Asp Asp Val Arg Ala Lys Gly
            980                 985                 990

Cys Arg His Val Gln His Arg Leu  Val Thr Glu Ala Glu  Ala Val Arg
        995                 1000                1005

Asp His  Trp Gly Arg Asn Ala  Ile Val Tyr Val Cys  Gly Ser Ser
    1010                1015                1020

Asn Met  Ala Arg Gly Val Gln  Thr Val Leu Glu Glu  Ile Leu Gly
    1025                1030                1035

Thr Leu  Pro Pro Glu Arg Tyr  Val Ala Glu Ile Phe
    1040                1045                1050
```

<210> SEQ ID NO 26
<211> LENGTH: 1050
<212> TYPE: PRT
<213> ORGANISM: Aspergillus kawachii

<400> SEQUENCE: 26

```
Met Lys Asp Ala Glu Arg Ile Pro Gly Pro Lys Pro Leu Pro Val Val
1               5                   10                  15

Gly Asn Leu Phe Asp Ile Asp Pro Glu His Ser Leu Glu Ser Ile Val
            20                  25                  30

Ala Phe Ala Glu Lys Phe Gly Pro Leu Phe Gln Ile Thr Ile Asn Gly
        35                  40                  45

Glu Lys Gln Ile Phe Ala Thr Ser Gln Ala Leu Val Asp Glu Leu Cys
    50                  55                  60

Asp Glu Leu Arg Phe His Lys Ala Val Val Thr Gly Leu Glu Ile Leu
65                  70                  75                  80

Arg Leu Leu Ala His Asp Gly Leu Phe Thr Ala Tyr His Gly Glu Arg
                85                  90                  95

Gly Trp Gly Ile Ala His Arg Ile Leu Val Pro Ala Phe Gly Pro Leu
            100                 105                 110

Arg Ile Arg Asn Met Leu Asp Asp Met Ser Asp Val Ala Gln Gln Leu
        115                 120                 125

Cys Leu Lys Trp Ala Arg Gln Gly Gly Ser Thr Ser Ile Asn Ile Thr
    130                 135                 140

Glu Asp Phe Thr Arg Leu Thr Leu Asp Thr Ile Ala Leu Cys Thr Met
145                 150                 155                 160

Gly Phe Arg Leu Asn Ser Phe Tyr Asn Asn Glu Thr Met His Pro Phe
                165                 170                 175

Val Gln Ser Met Leu Tyr Val Leu Arg Glu Ala Asp Ile Gln Ala Asn
            180                 185                 190

Leu Pro Gly Ile Ala Asn Ser Ile Arg Val Ser Ala Gln Arg Arg Met
        195                 200                 205

His Lys Asn Ile Glu Ala Met Arg Thr Met Ala Arg Gly Ile Ile Gln
    210                 215                 220

Glu Arg Arg Lys Asn Lys Asn Pro Val Asp Asp Ile Leu Asn Thr Leu
225                 230                 235                 240

Leu Asn Gly Arg Asp Pro Val Thr Gly Glu Gly Met Ser Asp Asp Ser
                245                 250                 255

Ile Ile Asp Asn Val Ile Thr Phe Leu Ile Ala Gly His Glu Thr Thr
            260                 265                 270

Ser Gly Leu Leu Ser Phe Thr Phe Tyr Phe Leu Ile Gln His Pro His
        275                 280                 285

Ile Leu Lys Lys Ala Gln Glu Glu Val Asp Glu Thr Val Gly Leu Ala
    290                 295                 300

Gln Ile Ser Ala Gln His Leu Ala Glu Leu Pro Tyr Ile Asp Ala Ile
305                 310                 315                 320

Leu Lys Glu Ser Leu Arg Leu Met Pro Thr Ala Pro Gly Phe Thr Val
                325                 330                 335

Thr Pro Lys Lys Thr Glu Val Leu Gly Gly Arg Trp Met Ile Asn Ala
            340                 345                 350

Gly Gln Pro Val Asn Val Leu Leu Pro Ala Cys Leu Arg Asp Gln Ser
        355                 360                 365

Val Phe Gly Pro Asp Ala Asp Glu Phe Arg Pro Glu Arg Met Leu Ala
    370                 375                 380
```

-continued

Glu Asn Phe Ser Lys Leu Pro Pro Asn Ser Trp Lys Pro Phe Gly Asn
385 390 395 400

Gly Glu Arg Gly Cys Ile Gly Arg Ala Phe Ala Trp Gln Glu Ala Gln
405 410 415

Leu Val Val Ala Met Ile Leu Gln Thr Phe Asp Leu Val Pro Asp Asp
420 425 430

Pro Ser Tyr Gln Leu Arg Ile Lys Glu Thr Leu Thr Ile Lys Pro Asp
435 440 445

Gly Phe Arg Ile Arg Ala Thr Leu Arg Arg Gly Gln Thr Ala Thr Gly
450 455 460

Leu Ser Arg Arg Ser Met Leu Val Ala Arg Asp Gly Ser Ser Glu Glu
465 470 475 480

Ser Ser Asn His Pro Ala Glu Ala Arg Gly Asp His Ala Pro Ala Arg
485 490 495

Gly Gln Pro Val Ser Phe Phe Tyr Gly Ser Asn Ser Gly Thr Cys Lys
500 505 510

Ala Leu Ala His Gln Leu Ala Ser Asn Met Met Ser Arg Gly Tyr Thr
515 520 525

Thr Gln Lys Leu Ala Pro Leu Asp Asn Ala Val Asp Asn Leu Pro Arg
530 535 540

Asp Gln Pro Val Ile Ile Leu Thr Thr Thr Tyr Asp Gly Gln Pro Thr
545 550 555 560

Asp Asn Ala Lys Lys Phe Val Ala Trp Leu Glu Thr Gly Asn Val Leu
565 570 575

Ser Leu Gln Gly Ile Ser Tyr Ala Val Phe Gly Cys Gly His His Asp
580 585 590

Trp Thr Gln Thr Phe Tyr Arg Ile Pro Ile Leu Ile Asp Asp Leu Met
595 600 605

Tyr Lys Ala Gly Ala Thr Arg Leu Ala Pro Arg Gly Ala Ala Asn Ala
610 615 620

Ala Val Ser Asp Leu Phe Ser Asp Leu Glu Ala Trp Glu Glu Thr Ser
625 630 635 640

Leu Leu Pro Ala Leu Arg Glu Asn Phe Leu Pro Ser Asn Ser Thr Asp
645 650 655

Phe Asp Pro Leu Asn Pro His Gln Ile Gln Leu Ser Leu Ser Lys Pro
660 665 670

Arg Arg Val Asp Leu His Lys Gly Leu Ile Glu Ala Lys Val Thr Ala
675 680 685

Val Arg Val Leu Thr Ser Pro Asp Thr Pro Glu Lys Arg His Leu Glu
690 695 700

Phe Cys Phe Gln Gly Asp Leu Ser Leu Arg Pro Gly Asp His Leu Asn
705 710 715 720

Ile Leu Pro Val Asn Pro Pro Ser Thr Val Ser Arg Val Leu Ala Gln
725 730 735

Phe Asn Leu Ala Pro Asp Tyr Asn Ile Thr Val Asn Ser Phe Asn Thr
740 745 750

Leu Gly Leu Pro Gln Ala Thr Pro Val Ser Ala Ser Glu Leu Phe Ser
755 760 765

Ser Tyr Val Glu Leu Cys Gln Pro Ala Thr Arg Asn Asn Leu Lys Ser
770 775 780

Leu Ile Ala Ala Thr Gln Ser Asp Thr Val Lys Gln Glu Leu Asn Arg
785 790 795 800

-continued

```
Leu Tyr Asp Ser Tyr Glu Phe Ile Val Arg Asp Lys Arg Val Ser Val
                805                 810                 815

Leu Asp Leu Leu Glu Gln Phe Pro Ser Ile Ser Leu Pro Ile Ala Ala
            820                 825                 830

Phe Ile Ser Met Leu Pro Ala Leu Arg Val Arg Thr Tyr Ser Leu Ser
        835                 840                 845

Met Ala Pro Ala Phe Lys Pro Ser His Ser Ser Leu Thr Phe Ser Val
    850                 855                 860

Ile Asn Glu Pro Ala Trp Arg Gly Ser Gly Gln His Leu Gly Val Ala
865                 870                 875                 880

Ser Asn Tyr Leu Ala Ser Leu Thr Ser Gly Ser Ile Phe Tyr Phe Ser
                885                 890                 895

Pro Arg Pro Ala Lys Glu Thr Phe His Leu Pro Lys Asp Pro Ser Arg
            900                 905                 910

Thr Pro Ile Ile Met Ile Cys Ala Gly Ser Gly Leu Ala Pro Phe Leu
        915                 920                 925

Ser Phe Ile Gln Asp Arg Met Val Leu Lys Gln Gln Asn Lys Pro Leu
    930                 935                 940

Ala Lys Ala Phe Leu Phe Phe Gly Cys Arg Gly Arg Ser Leu Asp Asp
945                 950                 955                 960

Leu Tyr His Glu Glu Leu Ser Glu Tyr Glu Ala Ala Gly Val Val Glu
                965                 970                 975

Val Arg Arg Ala Tyr Ser Lys Thr Pro Glu Phe Asp Ile Ala Lys Gly
            980                 985                 990

Cys Arg Tyr Val Gln His Arg Leu  Val Thr Glu Gly Gln  Ala Ile Leu
        995                 1000                1005

Ser Leu  Trp Ala Gln Asn Ala  Ile Ile Tyr Val Cys  Gly Ser Thr
    1010                1015                1020

Ser Met  Ala Lys Gly Ala Glu  Ala Val Leu Gln Asn  Met Leu Gly
    1025                1030                1035

Pro Leu  Pro Lys Glu Arg Tyr  Val Thr Glu Ile Phe
    1040                1045                1050
```

<210> SEQ ID NO 27
<211> LENGTH: 1091
<212> TYPE: PRT
<213> ORGANISM: Aspergillus niger

<400> SEQUENCE: 27

```
Met Ser Met Leu Leu Gly Val Arg Gly Thr Arg Asp Gln Ser Ser Tyr
1               5                   10                  15

Ile Gly Gly Arg Asp Tyr Val Phe Trp Gln Lys Glu Met Arg Asp Ala
            20                  25                  30

Glu Arg Ile Pro Gly Pro Thr Pro Leu Pro Val Val Gly Asn Leu Phe
        35                  40                  45

Asp Ile Asp Leu Glu His Val Leu Gln Ser Val Ile Gly Leu Ala Asn
    50                  55                  60

Lys Tyr Gly Pro Leu Phe Gln Ile Thr Ile Asn Gly Glu Lys Gln Ile
65                  70                  75                  80

Phe Ala Thr Ser Gln Ala Leu Val Asp Glu Leu Cys Asp Glu Ser Arg
                85                  90                  95

Phe His Lys Ala Val Ala Ser Gly Leu Glu Asn Leu Arg Met Leu Ala
            100                 105                 110

His Asp Gly Leu Phe Thr Ala Tyr His Gly Glu Arg Gly Trp Gly Ile
        115                 120                 125
```

```
Ala His Arg Ile Leu Val Pro Ala Phe Gly Pro Leu Arg Ile Gln Ser
    130                 135                 140

Met Phe Asp Asp Met Gly Asp Leu Ala Gln Gln Leu Cys Leu Lys Trp
145                 150                 155                 160

Ala Arg Gln Gly Ala Ser Asn Ser Ile Asn Ile Thr Asp Asp Phe Thr
                165                 170                 175

Arg Leu Thr Leu Asp Thr Ile Ala Leu Cys Thr Met Asp Phe Arg Leu
            180                 185                 190

Asn Ser Phe Tyr Asn Asn Asp Thr Met His Pro Phe Val Glu Ser Met
        195                 200                 205

Leu Tyr Val Leu Arg Glu Ala Asp Val Gln Ser Ala Leu Pro Gly Ile
    210                 215                 220

Ala Asn Ser Val Arg Ile Met Ala His Arg Arg Met Leu Lys Asn Ile
225                 230                 235                 240

Glu Ala Met Arg Thr Ile Ala Arg Asp Ile Ile His Asp Arg Arg Lys
                245                 250                 255

Lys Glu Asn Pro Ala Asp Asp Leu Leu Asn Thr Leu Leu Asn Gly Arg
            260                 265                 270

Asp Pro Val Thr Gly Glu Gly Met Ser Asp Glu Ser Ile Ile Asp Asn
        275                 280                 285

Val Ile Thr Phe Leu Val Ala Gly His Glu Thr Thr Ser Gly Leu Leu
    290                 295                 300

Ser Phe Thr Phe Tyr Tyr Leu Val Gln His Pro Asp Ile Leu Lys Lys
305                 310                 315                 320

Ala Gln Lys Glu Val Asp Glu Thr Val Gly Gln Ala Gln Ile Ser Val
                325                 330                 335

Gln His Leu Ala Glu Leu Pro Tyr Ile Asp Ala Ile Leu Lys Glu Ser
            340                 345                 350

Leu Arg Met Met Pro Thr Ala Pro Gly Phe Thr Val Thr Pro Lys Lys
        355                 360                 365

Ala Glu Thr Leu Gly Gly Lys Trp Leu Leu Asn Ala Gly Gln Pro Ile
    370                 375                 380

Asn Val Leu Leu Pro Ala Cys Leu Arg Asp Arg Ser Ile Phe Gly Pro
385                 390                 395                 400

Asn Ala Asp Glu Phe Ser Pro Gly Arg Met Leu Ala Glu Asn Phe Ser
                405                 410                 415

Lys Leu Pro Pro Asn Ser Trp Lys Pro Phe Gly Asn Gly Glu Arg Ser
            420                 425                 430

Cys Ile Gly Arg Ala Phe Ala Trp Gln Glu Ala Gln Leu Val Val Ala
        435                 440                 445

Met Ile Leu Gln Asn Phe Asp Leu Val Pro Asp Asp Pro Ser Tyr Thr
    450                 455                 460

Leu Arg Ile Lys Glu Thr Leu Thr Ile Lys Pro Asp Gly Phe Arg Val
465                 470                 475                 480

Arg Ala Thr Leu Arg His Arg Gln Thr Ala Thr Gly Leu Phe Gln His
                485                 490                 495

Thr Leu Ser Ala Arg Asn Asp Thr Ser Leu Ala Ser Ser Ser Ala His
            500                 505                 510

Phe Ile Lys Lys Ser Glu Asp Gln Ala Pro Ala Gly Gly Arg Pro Ile
        515                 520                 525

Cys Phe Phe Tyr Gly Ser Asn Ser Gly Thr Cys Lys Ala Leu Ala His
    530                 535                 540
```

```
Arg Leu Ala Ser Asp Leu Met Pro Tyr Gly Phe Thr Asp Gln Lys Leu
545                 550                 555                 560

Ala Val Leu Asp Thr Ala Val Asp Asn Leu Pro Arg Asp Gln Pro Val
                565                 570                 575

Ile Ile Leu Thr Thr Thr Tyr Asp Gly Gln Pro Thr Asp Asp Ala Lys
            580                 585                 590

Lys Phe Val Ala Trp Leu Glu Ser Gly Lys Val Pro Ala Leu Gln Gly
        595                 600                 605

Ile Ser Tyr Ala Val Phe Gly Cys Gly His His Asp Trp Thr Gln Thr
    610                 615                 620

Phe Tyr Arg Ile Pro Thr Leu Ile Asp Glu Leu Met His Lys Ala Gly
625                 630                 635                 640

Ala Thr Arg Leu Ala Pro Arg Gly Thr Ala Asn Ala Ala Val Ser Asp
                645                 650                 655

Leu Phe Ser Asp Leu Glu Ala Trp Glu Glu Thr Ser Leu Leu Pro Ala
            660                 665                 670

Leu Arg Glu Thr Phe Leu Leu Ser Ser Ser Ser Asp Leu Glu Pro Leu
        675                 680                 685

Asn Leu His Gln Leu Gln Ile Ser Leu Ser Lys Pro Arg Arg Ile Asp
    690                 695                 700

Leu His Lys Asp Leu Met Glu Ala Arg Val Thr Thr Val Arg Ile Leu
705                 710                 715                 720

Thr Asn Pro Asp Thr Pro Glu Lys Arg His Ile Glu Phe Arg Phe Gln
                725                 730                 735

Gly Asp Thr Thr Leu Arg Pro Gly Asp His Val Asn Val Leu Pro Val
            740                 745                 750

Asn Pro Pro Ser Thr Val Leu Arg Val Leu Ala Gln Phe Asn Leu Ala
        755                 760                 765

Pro Asp Tyr Ser Ile Thr Ile Asn Ser Phe Asn Thr Leu Gly Leu Pro
    770                 775                 780

Gln Ala Thr Pro Val Ser Ala Ser Glu Leu Phe Ser Ala Tyr Val Glu
785                 790                 795                 800

Leu Ser Gln Pro Ala Thr Arg Asn Asn Leu Arg Ile Leu Ala Ala Thr
                805                 810                 815

Ala Gln Ser Asp Glu Asp Lys Gln Glu Leu Ile His Leu Gln Asp Ser
            820                 825                 830

Tyr Asp Ser Leu Val Arg Asp Lys Arg Val Ser Val Leu Asp Leu Leu
        835                 840                 845

Glu Gln Phe Pro Ser Val Ser Leu Pro Ile Ala Ala Phe Ile Ser Met
    850                 855                 860

Leu Pro Ala Leu Arg Leu Arg Thr Tyr Ser Leu Ser Leu Ala Pro Ser
865                 870                 875                 880

Phe Lys Pro Ser His Gly Ser Leu Thr Phe Ser Val Val Asn Glu Pro
                885                 890                 895

Ala Arg Asn Gly Asn Arg Arg Tyr Leu Gly Val Gly Ser Asn Tyr Leu
            900                 905                 910

Ala Ser Leu Thr Pro Gly Ser Ile Leu Tyr Leu Ser Pro Arg Pro Ala
        915                 920                 925

Lys Glu Ala Phe His Leu Pro Val Asp Gln Ser Arg Ile Pro Ile Ile
    930                 935                 940

Met Ile Cys Ala Gly Ser Gly Leu Ala Pro Phe Leu Ser Phe Ile Gln
945                 950                 955                 960

Asp Arg Met Ile Trp Gln Gln Gln Asp Lys Pro Leu Ala Arg Ala Leu
```

965 970 975

Leu Phe Phe Gly Cys Gly Gly Arg Phe Leu Asp Asp Leu Tyr His Glu
980 985 990

Glu Leu Ser Glu Phe Glu Ala Ala Gly Val Val Asp Val Arg Arg Ala
995 1000 1005

Tyr Ser Lys Val Leu Asp Tyr Asp Met Ala Arg Gly Cys Lys Tyr
1010 1015 1020

Val Gln Asp Arg Leu Val Ala Glu Ala Asn Ala Ile Arg His Leu
1025 1030 1035

Trp Ala Gln Asp Ala Thr Ile Tyr Val Cys Gly Ser Ala Asp Met
1040 1045 1050

Ala Lys Gly Val Glu Gly Val Leu Glu Lys Leu Leu Gly Met Leu
1055 1060 1065

Pro Arg Glu Arg Tyr Val Thr Glu Ile Tyr Gln Met Gln Thr Arg
1070 1075 1080

Asp Asn Val Ser Glu Trp Leu Ile
1085 1090

<210> SEQ ID NO 28
<211> LENGTH: 1048
<212> TYPE: PRT
<213> ORGANISM: Penicillium expansum

<400> SEQUENCE: 28

Met Lys Asp Met Glu Ser Ile Pro Gly Pro Lys Pro Leu Pro Val Val
1 5 10 15

Gly Asn Leu Phe Asp Ile Asp Leu Glu Asn Gly Leu Gln Ser Ile Ile
20 25 30

Lys Met Ala His Glu Phe Gly Pro Leu Phe Gln Ile Thr Ile Asn Gly
35 40 45

Gln Lys Gln Ile Phe Ala Thr Ser Gln Ala Leu Val Asp Glu Leu Cys
50 55 60

Asp Glu Thr Arg Phe His Lys Ala Val Met Gly Gly Ile Gln Lys Leu
65 70 75 80

Arg Met Leu Ala Lys Asp Gly Leu Phe Thr Ala Tyr His Gly Glu Arg
85 90 95

Gly Trp Gly Ile Ala His Arg Ile Leu Met Pro Ala Phe Gly Pro Leu
100 105 110

Arg Ile Arg Asp Met Phe Glu Asp Met Ser Asp Val Ala Gln Gln Leu
115 120 125

Cys Phe Lys Trp Ala Arg Gln Gly Ser Ser Thr Ser Ile Asn Ile Cys
130 135 140

Asp Asp Phe Thr Arg Leu Thr Leu Asp Thr Ile Ala Leu Cys Thr Met
145 150 155 160

Gly Phe Arg Leu Asn Ser Tyr Tyr Asn Ser Asn Ala Leu His Pro Phe
165 170 175

Ile Glu Ser Met Leu Tyr Val Leu Lys Glu Ala Glu Leu Gln Ser Thr
180 185 190

Leu Pro Gly Val Ala Asn Cys Met Arg Val Lys Ala Gln Arg Arg Met
195 200 205

Ser Lys His Ile Asp Ala Met Arg Ser Met Ala Arg Asn Leu Ile Glu
210 215 220

Glu Arg Arg Ala Lys Pro Glu Pro Val Asp Asp Leu Leu Asn Thr Leu
225 230 235 240

-continued

```
Leu Asn Gly Arg Asp Pro Ile Thr Gly Glu Gly Met Ser Asp Asp Leu
                245                 250                 255

Ile Ile Ser Asn Ile Ile Thr Phe Leu Ile Ala Gly His Glu Thr Thr
            260                 265                 270

Ser Gly Leu Leu Ser Phe Thr Phe Tyr Tyr Leu Leu Gln Asn Gln Asp
        275                 280                 285

Val Leu Glu Arg Ala Arg Asn Glu Val Asp Glu Val Thr Gly Val Gly
    290                 295                 300

Pro Ile Thr Val Gln His Leu Ala Lys Leu Pro Tyr Ile Asp Ala Ile
305                 310                 315                 320

Met Lys Glu Ser Leu Arg Leu Met Pro Thr Ala Pro Ala Phe Thr Val
                325                 330                 335

Thr Pro Gln Lys Pro Glu Val Leu Gly Gly Lys Trp Met Ile Asn Thr
            340                 345                 350

Gly Asp Ser Val Asn Leu Leu Leu Pro Val Cys Leu Arg Asp Glu Thr
        355                 360                 365

Val Phe Gly Pro Asp Ala Gly Glu Phe Arg Pro Asn Arg Met Leu Glu
    370                 375                 380

Glu Asn Phe Ser Lys Leu Pro Pro Asn Ser Trp Lys Pro Phe Gly Asn
385                 390                 395                 400

Gly Glu Arg Gly Cys Ile Gly Arg Ala Phe Ala Trp Gln Glu Ala Gln
                405                 410                 415

Leu Val Val Ala Leu Val Leu Arg Thr Phe Asp Leu Ala Ala Glu Asp
            420                 425                 430

Pro Tyr Tyr Lys Leu Arg Ile Lys Glu Thr Leu Thr Ile Lys Pro Asp
        435                 440                 445

Gly Phe Arg Ile Arg Ala Thr Leu Arg His Gly Lys Ser Ala Thr Ala
    450                 455                 460

Leu Ser Gln His Asn Ile Ser Val Gly Ala Ala Ala Ser Pro Ala Ser
465                 470                 475                 480

Ser Thr Tyr Leu Ala Gly Asn Glu Asn Gly Arg Asp Ala Ala Gly Gly
                485                 490                 495

Gln Pro Val Ser Phe Phe Tyr Gly Ser Asn Ser Gly Thr Cys Lys Ala
            500                 505                 510

Leu Thr His Arg Leu Ala Ser Thr Met Met Thr Arg Gly Phe Thr Asp
        515                 520                 525

Gln Asn Ile Ala Pro Leu Asp Ser Ala Val Asp Asn Leu Pro Arg Asp
    530                 535                 540

Gln Pro Thr Ile Ile Ile Thr Thr Thr Tyr Asp Gly Gln Pro Thr Asp
545                 550                 555                 560

Asp Ala Lys Lys Phe Val Ala Trp Leu Glu Ser Gly Asn Ser Pro Ser
                565                 570                 575

Leu Gln Gly Val Ser Tyr Ala Val Phe Gly Cys Gly His Gln Asp Trp
            580                 585                 590

Thr Lys Thr Phe Tyr Arg Ile Pro Ile Leu Ile Asp Asn Leu Met Tyr
        595                 600                 605

Lys Ala Gly Ala Thr Arg Leu Ala Thr Arg Gly Ala Ala Asn Ala Ala
    610                 615                 620

Ile Ser Asp Leu Phe Ser Asp Leu Glu Val Trp Glu Glu Thr Asn Leu
625                 630                 635                 640

Leu Pro Gly Leu Arg Glu Ser Phe Tyr Pro Pro Asn Asn Ser Asn Phe
                645                 650                 655

Val Pro Leu Glu Pro His Gln Leu Gln Ile Ser Ile Asn Lys Pro Thr
```

-continued

```
            660                 665                 670

Arg Val Gly Met His Arg Asp Leu Ile Glu Ala Lys Val Thr Ala Ile
        675                 680                 685

Arg Thr Leu Thr Ser Pro Gly Ala Pro Glu Lys Arg His Leu Glu Phe
    690                 695                 700

Cys Ile Pro Gly Glu Thr Thr Leu Arg Pro Gly Asp His Leu Asn Ile
705                 710                 715                 720

Leu Pro Val Asn Pro Pro Ser Thr Val Ser Arg Ala Leu Ala Arg Phe
                725                 730                 735

Asn Leu Ala Pro Asp His Ser Ile Thr Phe Glu Ser Ser Asn Ala Leu
            740                 745                 750

Asp Leu Pro Gln Ala Thr Pro Val Ser Ala Ala Glu Leu Phe Ser Ser
        755                 760                 765

Tyr Leu Glu Leu Ser Gln Pro Ala Thr Arg Asn Asn Leu Lys Glu Leu
    770                 775                 780

Ala Ser Thr Thr Pro Ser Asp Gly Glu Lys Gln Glu Leu Leu His Leu
785                 790                 795                 800

Tyr Asp Ser Tyr Asp Ser Leu Ile Arg Ala Lys Arg Ala Ser Val Leu
                805                 810                 815

Asp Leu Leu Glu Gln Phe Thr Ser Val Thr Leu Pro Ile Thr Thr Phe
            820                 825                 830

Ile Ser Met Leu Pro Ala Leu Arg Val Arg Thr Tyr Ser Leu Ser Met
        835                 840                 845

Ala Pro Ser Phe Lys Pro Leu His Tyr Ser Leu Thr Phe Ser Val Ile
    850                 855                 860

Asn Glu Pro Ala Trp Asn Gly Asn Gly Arg Tyr Leu Gly Val Ala Ser
865                 870                 875                 880

Asn Tyr Leu Ala Ser Leu Asn Leu Gly Ser Ile Leu Tyr Ile Ser Pro
                885                 890                 895

Arg Pro Ala Lys Asp Ala Phe His Leu Pro Thr Asp Gln Ser Ser Lys
            900                 905                 910

Pro Ile Ile Met Ile Cys Ala Gly Ser Gly Leu Ala Pro Phe Arg Ser
        915                 920                 925

Phe Ile Gln Asp Arg Met Leu Trp Gln Gln Gln Asp Lys Thr Leu Ala
    930                 935                 940

Lys Ala Leu Leu Phe Phe Gly Cys Arg Ser Pro Gln Leu Asp Asp Leu
945                 950                 955                 960

Tyr His Asp Glu Leu Ser Gln Phe Glu Ala Ala Gly Val Val Glu Val
                965                 970                 975

Arg Arg Ala Tyr Ser Lys Val Pro Asn His Tyr Leu Ala Lys Gly Cys
            980                 985                 990

Arg Tyr Val Gln His Arg Leu Leu  Thr Glu Thr Glu Thr  Ile Gln Asp
        995                 1000                1005

Met Trp  Ala Gln Asp Ala Ile  Ile Tyr Val Cys Gly  Ser Gly Asn
    1010                1015                1020

Leu Ala  Lys Gly Val Lys Ala  Val Leu Glu Ser Met  Leu Gly Thr
    1025                1030                1035

Leu Tyr  Glu Arg Tyr Ile Thr  Glu Ile Phe
    1040                1045
```

<210> SEQ ID NO 29
<211> LENGTH: 1050
<212> TYPE: PRT
<213> ORGANISM: Aspergillus niger

<400> SEQUENCE: 29

Met Lys Asp Ala Glu Arg Ile Pro Gly Pro Lys Pro Leu Pro Val Val
1 5 10 15

Gly Asn Leu Leu Asp Ile Asp Pro Glu His Gly Leu Gln Ser Ile Ile
20 25 30

Ala Phe Ala Asp Lys Tyr Gly Pro Leu Phe Gln Ile Thr Ile Asn Gly
35 40 45

Glu Lys Gln Ile Phe Ala Thr Ser Gln Ala Leu Val Asp Glu Leu Cys
50 55 60

Asp Glu Ser Arg Phe His Lys Ala Val Val Thr Gly Leu Glu Val Leu
65 70 75 80

Arg Leu Leu Ala His Asp Gly Leu Phe Thr Ala Tyr His Gly Glu Arg
85 90 95

Gly Trp Gly Ile Ala His Arg Ile Leu Val Pro Ala Phe Gly Pro Leu
100 105 110

Arg Ile Arg Asn Met Leu Asp Asp Met Ser Asp Val Ala Gln Gln Leu
115 120 125

Cys Leu Lys Trp Ala Arg Gln Gly Gly Ser Thr Ser Ile Asn Ile Thr
130 135 140

Glu Asp Phe Thr Arg Leu Thr Leu Asp Thr Ile Ala Leu Cys Thr Met
145 150 155 160

Gly Phe Arg Leu Asn Ser Phe Tyr Asn Asn Glu Thr Met His Pro Phe
165 170 175

Val Gln Ser Met Leu Tyr Val Leu Lys Glu Ala Asp Val Gln Ala Asn
180 185 190

Leu Pro Gly Ile Ala Asn Ser Ile Arg Val Ser Ala Gln Arg Arg Met
195 200 205

His Lys Asn Ile Glu Ala Met Arg Thr Met Ala Arg Gly Ile Ile Gln
210 215 220

Glu Arg Arg Lys Asn Lys Asn Pro Val Asp Asp Ile Leu Asn Thr Leu
225 230 235 240

Leu Asn Gly Arg Asp Pro Val Thr Gly Glu Gly Met Ser Asp Asp Ser
245 250 255

Ile Ile Asp Asn Val Ile Thr Phe Leu Ile Ala Gly His Glu Thr Thr
260 265 270

Ser Gly Leu Leu Ser Phe Thr Phe Tyr Phe Leu Ile Gln His Pro His
275 280 285

Ile Leu Lys Lys Ala Gln Glu Glu Val Asp Glu Thr Val Gly Leu Ala
290 295 300

Gln Ile Ser Ala Gln His Leu Ala Glu Leu Pro Tyr Ile Asp Ala Ile
305 310 315 320

Leu Lys Glu Ser Leu Arg Leu Met Pro Thr Ala Pro Gly Phe Ala Val
325 330 335

Thr Pro Lys Lys Thr Glu Val Leu Gly Gly Lys Trp Met Ile Asn Ala
340 345 350

Gly Gln Pro Val Asn Val Leu Leu Pro Ala Cys Leu Arg Asp Gln Ser
355 360 365

Val Phe Gly Pro Asp Ala Asp Glu Phe His Pro Glu Arg Met Leu Ala
370 375 380

Glu Asn Phe Ser Lys Leu Pro Pro Asn Ser Trp Lys Pro Phe Gly Asn
385 390 395 400

Gly Glu Arg Gly Cys Ile Gly Arg Ala Phe Ala Trp Gln Glu Ala Gln 405 410 415

Leu Val Val Ala Met Ile Leu Gln Thr Phe Asp Leu Val Pro Asp Asp
420 425 430

Pro Ser Tyr Gln Leu Arg Ile Lys Glu Thr Leu Thr Ile Lys Pro Asp
435 440 445

Gly Phe Arg Ile Arg Ala Leu Leu Arg Arg Gly Gln Thr Ala Thr Gly
450 455 460

Leu Ser Arg Arg Ser Met Leu Val Ala Arg Asp Gly Ser Ser Gly Glu
465 470 475 480

Ser Ser Asn His Leu Ala Glu Ala Arg Gly Asp His Ala Pro Ala Arg
485 490 495

Gly Gln Pro Val Ser Phe Phe Tyr Gly Ser Asn Ser Gly Thr Cys Lys
500 505 510

Ala Leu Ala His Gln Leu Ala Ser Asn Met Met Ser Arg Gly Tyr Thr
515 520 525

Thr Gln Lys Leu Ala Pro Leu Asp Asn Ala Val Gly Asn Leu Pro Arg
530 535 540

Asp Gln Pro Val Ile Ile Leu Thr Thr Thr Tyr Asp Gly Gln Pro Thr
545 550 555 560

Asp Asp Ala Lys Lys Phe Val Ala Trp Leu Glu Thr Gly Asn Val Pro
565 570 575

Ser Leu Gln Gly Ile Ser Tyr Ala Val Phe Gly Cys Gly His His Asp
580 585 590

Trp Thr Gln Thr Phe Tyr Arg Ile Pro Ile Leu Ile Asp Asp Leu Met
595 600 605

His Lys Ala Gly Ala Thr Arg Leu Ala Pro Arg Gly Ala Ala Asn Ala
610 615 620

Ala Val Ser Asp Leu Phe Ser Asp Leu Glu Ala Trp Glu Glu Thr Ser
625 630 635 640

Leu Leu Pro Ala Leu Arg Glu Asn Phe Leu Pro Ser Asn Ser Thr Asp
645 650 655

Phe Asp Pro Leu Asn Pro His Gln Ile Gln Leu Ser Leu Ser Lys Pro
660 665 670

Arg Arg Val Asp Leu His Lys Gly Leu Ile Glu Ala Lys Val Thr Ala
675 680 685

Val Arg Val Leu Thr Ser Pro Asp Thr Pro Glu Lys Arg His Leu Glu
690 695 700

Phe Cys Phe Gln Gly Asp Thr Ser Leu Arg Pro Gly Asp His Leu Asn
705 710 715 720

Ile Leu Pro Val Asn Pro Pro Ser Thr Val Ser Arg Val Leu Ala Gln
725 730 735

Phe Asn Leu Ala Pro Asp Tyr Asn Ile Thr Val Asn Ser Phe Asn Thr
740 745 750

Leu Gly Leu Pro Gln Ala Thr Pro Val Ser Ala Ser Glu Leu Phe Ser
755 760 765

Ser Tyr Val Glu Leu Cys Gln Pro Ala Thr Arg Asn Asn Leu Lys Ala
770 775 780

Leu Ile Ala Ala Thr Gln Ser Asp Pro Asp Lys Gln Glu Leu Asn Arg
785 790 795 800

Leu Tyr Asp Ser Tyr Glu Phe Ile Val Arg Asp Lys Arg Val Ser Val
805 810 815

Leu Asp Leu Leu Glu Gln Phe Pro Ser Ile Ser Leu Pro Ile Ala Ala
820 825 830

Phe Ile Ser Met Leu Pro Ala Leu Arg Val Arg Thr Tyr Ser Leu Ser
835 840 845

Met Ala Pro Ser Phe Lys Pro Ser His Ser Ser Leu Thr Phe Ser Val
850 855 860

Ile Asn Glu Pro Ala Trp Arg Gly Ser Gly Gln His Leu Gly Val Ala
865 870 875 880

Ser Asn Tyr Leu Ala Ser Leu Thr Ser Gly Ser Ile Phe Tyr Phe Ser
885 890 895

Pro Arg Pro Ala Lys Glu Ser Phe His Leu Pro Lys Asp Pro Ser Asn
900 905 910

Thr Pro Ile Ile Met Ile Cys Ala Gly Ser Gly Leu Ala Pro Phe Leu
915 920 925

Ser Phe Ile Gln Asp Arg Met Val Leu Lys Gln Gln Tyr Lys Pro Leu
930 935 940

Ala Lys Ala Phe Leu Phe Phe Gly Cys Arg Gly Arg Ser Leu Asp Asp
945 950 955 960

Leu Tyr His Glu Glu Leu Ser Glu Phe Glu Ala Ala Gly Val Val Glu
965 970 975

Ile Arg Arg Ala Tyr Ser Lys Thr Pro Asp Phe Asp Ile Ala Lys Gly
980 985 990

Cys Arg Tyr Val Gln His Arg Leu Val Thr Glu Gly Gln Ala Ile Leu
995 1000 1005

Ser Leu Trp Ser Gln Asn Ala Thr Ile Tyr Val Cys Gly Ser Thr
1010 1015 1020

Asn Met Ala Lys Gly Val Glu Ala Val Leu Gln Asn Met Leu Gly
1025 1030 1035

Pro Leu Pro Lys Glu Arg Tyr Val Thr Glu Ile Phe
1040 1045 1050

<210> SEQ ID NO 30
<211> LENGTH: 1049
<212> TYPE: PRT
<213> ORGANISM: Penicillium camemberti

<400> SEQUENCE: 30

Met Lys Asp Met Asp Cys Ile Pro Gly Pro Lys Pro Leu Pro Val Val
1 5 10 15

Gly Asn Leu Phe Asp Leu Asp Leu Asp Asn Ala Leu Gln Ser Ile Ile
20 25 30

Arg Met Ala Asp Glu Phe Gly Pro Leu Phe Gln Ile Thr Ile Asn Gly
35 40 45

Gln Lys Gln Ile Phe Ala Thr Ser Gln Ala Leu Val Asp Glu Leu Cys
50 55 60

Asp Glu Thr Arg Phe His Lys Ala Val Met Gly Gly Val Glu Lys Leu
65 70 75 80

Arg Met Leu Ala Gln Asp Gly Leu Phe Thr Ala His His Gly Glu Arg
85 90 95

Gly Trp Gly Ile Ala His Arg Ile Leu Met Pro Ala Phe Gly Pro Leu
100 105 110

Arg Ile Arg Asp Met Phe Glu Asp Met Ser Asp Val Ala His Gln Leu
115 120 125

Cys Phe Lys Trp Ala Arg Gln Gly Ser Ser Ala Ser Ile Asn Ile Ala
130 135 140

Glu Asp Phe Thr Arg Leu Thr Leu Asp Thr Ile Ala Leu Cys Thr Met

-continued

```
145                 150                 155                 160

Ser Phe Arg Leu Asn Ser Tyr Tyr Asn Ser Glu Thr Met His Pro Phe
                165                 170                 175

Val Gln Ser Met Leu Tyr Val Leu Lys Glu Ala Asp Leu Gln Ala Thr
            180                 185                 190

Leu Pro Gly Val Ala Asn Cys Val Arg Val Lys Ala Gln Arg Arg Met
        195                 200                 205

Ser Lys His Ile Gln Ala Met Arg Asn Ile Ala Gly Asp Ile Ile Lys
    210                 215                 220

Gly Arg Arg Asp Lys Pro Glu Pro Val Asp Asp Leu Leu Asn Thr Leu
225                 230                 235                 240

Leu Asn Gly Arg Asp Pro Val Thr Gly Glu Gly Met Ser Asp Glu Leu
                245                 250                 255

Ile Ile Ser Asn Ile Ile Thr Phe Leu Val Ala Gly His Glu Thr Thr
            260                 265                 270

Ser Gly Leu Leu Ser Phe Thr Phe Tyr Tyr Leu Leu Gln His Pro His
        275                 280                 285

Val Leu Glu Gln Ala Arg Asn Glu Val Asp Glu Val Val Gly Val Gly
    290                 295                 300

Pro Ile Thr Val Gln His Leu Ala Lys Leu Pro Tyr Ile Asp Ala Val
305                 310                 315                 320

Met Lys Glu Ser Leu Arg Leu Met Pro Thr Ala Pro Ala Phe Thr Val
                325                 330                 335

Thr Pro Lys Lys Pro Glu Val Val Gly Gly Lys Trp Met Val Asn Thr
            340                 345                 350

Gly Gln Ser Val His Val Leu Leu Pro Val Cys Leu Arg Asp Glu Ala
        355                 360                 365

Val Phe Gly Pro Asp Ala Gly Glu Phe Arg Pro Thr Arg Met Leu Glu
    370                 375                 380

Glu Asn Phe Ser Lys Leu Pro Pro Asn Ser Trp Lys Pro Phe Gly Asn
385                 390                 395                 400

Gly Glu Arg Gly Cys Ile Gly Arg Ala Phe Ala Trp Gln Glu Ala Gln
                405                 410                 415

Leu Val Val Ala Ser Val Leu Gln Thr Phe Asp Leu Val Ala Glu Asp
            420                 425                 430

Pro Tyr Tyr Lys Leu Arg Ile Lys Glu Thr Leu Thr Ile Lys Pro Asp
        435                 440                 445

Gly Phe Arg Val Arg Ala Thr Leu Arg Arg Gly Gln Ser Ala Thr Ala
    450                 455                 460

Leu Ser Gln His Asn Met Ser Ala Gly Ala Thr Ala Ser Pro Gly Ser
465                 470                 475                 480

Ser Thr His Leu Ala Gly Asp Glu Asn Gly Gln Asp Thr Ala Gly Gly
                485                 490                 495

Gln Pro Ile Ser Phe Phe Tyr Gly Ser Asn Ser Gly Thr Cys Lys Ala
            500                 505                 510

Leu Ala His Arg Leu Ala Ser Thr Met Met Thr Arg Gly Phe Thr Asp
        515                 520                 525

Gln His Leu Ala Gln Leu Asp Ser Ala Val Asp Asn Leu Pro Arg Asp
    530                 535                 540

Gln Pro Thr Ile Ile Val Thr Thr Thr Tyr Asp Gly Gln Pro Thr Asp
545                 550                 555                 560

Asp Ala Lys Lys Phe Leu Ala Trp Leu Glu Ser Gly Asn Val Pro Ser
                565                 570                 575
```

-continued

```
Leu His Gly Val Ser Tyr Ala Val Phe Gly Cys Gly His Gln Asp Trp
            580                 585                 590

Thr Lys Thr Phe Tyr Arg Ile Pro Ile Leu Ile Asp Asp Leu Met His
        595                 600                 605

Lys Ala Gly Ala Thr Arg Leu Thr Thr Arg Gly Thr Ala Asn Ala Ala
    610                 615                 620

Val Ser Asp Leu Phe Ser Asp Leu Glu Val Trp Glu Glu Thr Asn Leu
625                 630                 635                 640

Leu Pro Ala Leu Arg Glu Lys Phe Tyr Leu Cys Asn Ser Ser Asp Phe
                645                 650                 655

Glu Pro Leu Asp Pro His Gln Leu Gln Ile Ser Ile Ser Lys Pro Ala
            660                 665                 670

Arg Val Gly Met His Arg Asp Leu Val Glu Gly Lys Val Thr Ala Ile
        675                 680                 685

Arg Thr Leu Thr Ser Pro Gly Val Pro Glu Lys Arg His Val Glu Phe
    690                 695                 700

Gln Ile Pro Ser Glu Met Ala Leu Arg Pro Gly Asp His Val Asn Ile
705                 710                 715                 720

Leu Pro Val Asn Pro Pro Cys Ser Val Leu Arg Ala Leu Ala Arg Phe
                725                 730                 735

Ser Leu Ala Ser Asp His Ser Ile Thr Phe Glu Ser Ser Asn Ala Leu
            740                 745                 750

Asp Leu Pro Gln Ala Thr Pro Val Ser Ala Ala Glu Leu Phe Ser Ser
        755                 760                 765

Tyr Leu Glu Leu Ser Gln Pro Ala Thr Arg Ile Asn Leu Lys Ser Leu
    770                 775                 780

Ala Ser Ala Thr Pro Ser Asp Asp Asp Lys Lys Glu Leu Leu His Phe
785                 790                 795                 800

His Asp Ser Tyr Asp Ser Leu Ile Arg Asp Lys Arg Val Ser Val Leu
                805                 810                 815

Asp Leu Leu Glu His Phe Thr Ser Ile Thr Leu Pro Ile Ala Thr Phe
            820                 825                 830

Ile Ser Met Leu Pro Val Leu Arg Val Arg Thr Tyr Ser Leu Ser Met
        835                 840                 845

Ala Pro Ser Phe Lys Pro Leu His Cys Ser Leu Thr Phe Ser Val Val
    850                 855                 860

Asn Glu Pro Ala Trp Ser Gly Asn Gly Arg Tyr Leu Gly Val Gly Ser
865                 870                 875                 880

Asn Tyr Leu Ala Ser Leu Thr Pro Gly Ser Ile Leu Tyr Val Ser Pro
                885                 890                 895

Arg Pro Ala Lys Asp Ala Phe His Leu Pro Thr Asp Gln Ser Ser Asn
            900                 905                 910

Pro Ile Ile Met Ile Cys Ala Gly Ser Gly Leu Ala Pro Phe Arg Ser
        915                 920                 925

Phe Ile Gln Asp Arg Met Ala Trp Leu Gln Gln Gly Lys Pro Leu Ala
    930                 935                 940

Lys Ala Leu Leu Phe Phe Gly Cys Arg Gly Pro His Leu Asp Asp Leu
945                 950                 955                 960

Tyr His Asp Glu Leu Ser Glu Phe Glu Ser Ala Gly Val Val Glu Val
                965                 970                 975

Arg Arg Ala Tyr Ser Lys Val Pro Asn His Tyr Leu Ala Lys Gly Cys
            980                 985                 990
```

-continued

Arg Tyr Ala Gln His Arg Leu Leu Thr Glu Thr Glu Thr Ile Gln Asp
995 1000 1005

Met Trp Ala His Asn Ala Thr Leu Tyr Leu Cys Gly Ser Ala Asn
1010 1015 1020

Leu Ala Lys Gly Val Lys Ala Val Leu Glu Asn Met Leu Gly Thr
1025 1030 1035

Leu Ser Glu Glu Arg Tyr Ile Thr Glu Ile Phe
1040 1045

<210> SEQ ID NO 31
<211> LENGTH: 1049
<212> TYPE: PRT
<213> ORGANISM: Penicillium freii

<400> SEQUENCE: 31

Met Lys Asp Met Asp Cys Ile Pro Gly Pro Lys Pro Leu Pro Val Val
1 5 10 15

Gly Asn Leu Phe Asp Leu Asp Leu Asp Asn Ala Leu Gln Ser Ile Ile
20 25 30

Lys Met Ala Asp Glu Phe Gly Pro Leu Phe Gln Ile Thr Val Asn Arg
35 40 45

Gln Lys His Ile Phe Ala Thr Ser Gln Ala Leu Val Asp Glu Leu Cys
50 55 60

Asp Glu Thr Arg Phe His Lys Ala Val Ile Gly Gly Val Glu Lys Leu
65 70 75 80

Arg Met Leu Ala His Asp Gly Leu Phe Thr Ala His His Gly Glu Arg
85 90 95

Gly Trp Gly Ile Ala His Arg Ile Leu Met Pro Ala Phe Gly Pro Leu
100 105 110

Arg Ile Arg Asp Met Phe Glu Asp Met Ser Asp Val Ala His Gln Leu
115 120 125

Cys Phe Lys Trp Ala Arg Gln Gly Ser Ser Thr Ser Ile Asn Ile Ser
130 135 140

Glu Asp Phe Thr Arg Leu Thr Leu Asp Thr Ile Ala Leu Cys Thr Met
145 150 155 160

Ser Phe Arg Leu Asn Ser Tyr Tyr Asn Ser Asp Thr Met His Pro Phe
165 170 175

Val Gln Ser Met Leu Tyr Val Leu Lys Glu Ala Asp Leu Gln Ser Ser
180 185 190

Leu Pro Glu Val Ala Asn Cys Val Arg Val Lys Ala Gln Arg Ser Met
195 200 205

Ser Lys His Ile Glu Ala Met Arg Ser Ile Ala Gly Asp Ile Ile Lys
210 215 220

Gly Arg Arg Asp Lys Pro Glu Pro Val Asn Asp Leu Leu Asn Thr Leu
225 230 235 240

Leu Asn Gly Arg Asp Pro Val Thr Gly Glu Gly Met Ser Asp Glu Leu
245 250 255

Ile Ile Ser Asn Ile Ile Thr Phe Leu Ile Ala Gly His Glu Thr Thr
260 265 270

Ser Gly Leu Leu Ser Phe Thr Phe Tyr Tyr Leu Leu Gln His Pro Gln
275 280 285

Val Leu Glu Gln Ala Arg Asn Glu Val Asp Glu Val Val Gly Val Gly
290 295 300

Pro Ile Thr Val Gln His Leu Ala Lys Leu Pro Tyr Ile Asp Ala Ile
305 310 315 320

-continued

```
Met Lys Glu Ser Leu Arg Leu Met Pro Thr Ala Pro Ser Phe Thr Val
                325                 330                 335

Thr Pro Lys Lys Pro Glu Val Leu Gly Gly Lys Trp Met Ile Asn Pro
            340                 345                 350

Gly Gln Ser Val His Val Leu Leu Pro Val Cys Leu Arg Asp Glu Ala
        355                 360                 365

Val Phe Gly Pro Asp Ala Gly Glu Phe Arg Pro Asn Arg Met Leu Glu
    370                 375                 380

Glu Asn Phe Ser Lys Leu Pro Pro Asn Ser Trp Lys Pro Phe Gly Asn
385                 390                 395                 400

Gly Glu Arg Gly Cys Ile Gly Arg Ala Phe Ala Trp Gln Glu Ala Gln
                405                 410                 415

Leu Val Val Ala Ser Val Leu Gln Thr Phe Asp Leu Val Ala Glu Asp
            420                 425                 430

Pro Asn Tyr Lys Leu Arg Val Lys Glu Thr Leu Thr Ile Lys Pro Asp
        435                 440                 445

Gly Phe Arg Val Arg Ala Thr Leu Arg His Gly Arg Ser Ala Thr Ala
    450                 455                 460

Leu Ser Gln His Asn Met Ser Ala Gly Ala Thr Ser Ser Pro Gly Ser
465                 470                 475                 480

Ser Ala His Pro Ala Gly Asn Lys Asn Ala Gln Asp Ala Ala Gly Gly
                485                 490                 495

Gln Ser Ile Ser Phe Phe Tyr Gly Ser Asn Ser Gly Thr Cys Lys Ala
            500                 505                 510

Leu Ala His Arg Leu Ala Ser Thr Met Met Thr Arg Gly Phe Thr Asp
        515                 520                 525

Gln His Leu Ala Pro Leu Asp Ser Ala Val Asp Asn Leu Pro Lys Asp
    530                 535                 540

Gln Pro Thr Ile Ile Val Thr Thr Thr Tyr Glu Gly Gln Pro Thr Asp
545                 550                 555                 560

Asp Ala Lys Lys Phe Leu Ala Trp Leu Glu Ser Gly Ile Val Pro Ser
                565                 570                 575

Leu His Gly Val Ser Tyr Ala Val Phe Gly Cys Gly His Gln Asp Trp
            580                 585                 590

Thr Lys Thr Phe Tyr Arg Ile Pro Ile Leu Ile Asp Asp Leu Met His
        595                 600                 605

Lys Ala Gly Ala Thr Arg Leu Thr Thr Arg Gly Glu Ala Asn Ala Ala
    610                 615                 620

Val Ser Asp Leu Phe Ser Asp Leu Glu Val Trp Glu Glu Thr Asn Leu
625                 630                 635                 640

Leu Pro Ala Leu Arg Glu Lys Phe Asp Ala Ser Asn Ser Gly Glu Phe
                645                 650                 655

Glu Ser Leu Asp Leu Gln Gln Leu Gln Ile Ser Ile Ser Lys Pro Thr
            660                 665                 670

Arg Val Gly Met His Arg Asp Leu Ile Glu Gly Lys Val Thr Ala Ile
        675                 680                 685

Arg Thr Leu Thr Ser Pro Gly Val Pro Glu Lys Arg His Val Glu Phe
    690                 695                 700

Gln Ile Thr Ser Asp Thr Thr Leu Arg Pro Gly Asp His Val Asn Ile
705                 710                 715                 720

Leu Pro Val Asn Pro Pro Ser Thr Val Leu Arg Ala Leu Ala Arg Phe
                725                 730                 735
```

-continued

```
Asn Leu Ala Ser Asp His Ile Ile Thr Phe Glu Ser Ser Asn Ala Leu
            740                 745                 750

Asp Leu Pro Gln Ala Thr Pro Val Ser Ala Ala Glu Leu Phe Gly Ser
        755                 760                 765

Tyr Leu Glu Leu Ser Gln Pro Ala Thr Arg Asn Asn Leu Lys Ser Leu
    770                 775                 780

Ala Ser Thr Thr Pro Ser Asp Glu Asp Lys Gln Glu Leu Leu Arg Phe
785                 790                 795                 800

His Asp Ser Tyr Asp Ser Leu Ile Arg Asp Lys Arg Val Ser Val Leu
                805                 810                 815

Asp Leu Leu Glu His Phe Thr Ser Ile Thr Leu Pro Ile Ala Thr Phe
            820                 825                 830

Ile Ser Met Leu Pro Val Leu Arg Val Arg Thr Tyr Ser Leu Ser Met
        835                 840                 845

Ala Pro Ser Phe Lys Pro Leu His Cys Ser Leu Thr Phe Ser Val Val
    850                 855                 860

Asn Glu Pro Ala Trp Ser Gly Asn Gly Arg Tyr Leu Gly Val Gly Ser
865                 870                 875                 880

Asn Tyr Leu Ala Ser Leu Thr Pro Gly Ser Ile Leu Tyr Val Ser Pro
                885                 890                 895

Arg Pro Ala Lys Glu Ala Phe His Leu Pro Ala Asp Gln Ser Ser Lys
            900                 905                 910

Pro Ile Ile Met Ile Cys Ala Gly Ser Gly Leu Ala Pro Phe Arg Ser
        915                 920                 925

Phe Ile Gln Asp Arg Met Ala Trp Leu Gln Gln Gly Lys Pro Leu Ala
    930                 935                 940

Lys Ala Leu Leu Phe Phe Gly Cys Arg Gly Pro Gln Leu Asp Asp Leu
945                 950                 955                 960

Tyr His Asp Glu Leu Ser Glu Phe Glu Ser Ala Gly Val Val Glu Val
                965                 970                 975

Arg Arg Ala Tyr Ser Lys Val Pro Asn His Tyr Pro Gly Lys Gly Cys
            980                 985                 990

Arg Tyr Val Gln His Arg Leu Phe  Ala Glu Thr Glu Thr  Ile Gln Asp
        995                 1000                1005

Met Trp  Ala His Asn Ala Thr  Leu Tyr Leu Cys Gly  Ser Ala Thr
    1010                1015                1020

Leu Ala  Lys Gly Val Lys Ala  Thr Leu Glu Asn Met  Leu Gly Thr
    1025                1030                1035

Leu Ser  Glu Glu Arg Tyr Ile  Thr Glu Ile Phe
    1040                1045
```

```
<210> SEQ ID NO 32
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Asn, Ser or absent
<220> FEATURE:
<221> NAME/KEY: MOD_RES
<222> LOCATION: (4)..(4)
<223> OTHER INFORMATION: Thr, Lys, Met or Asn
<220> FEATURE:
<221> NAME/KEY: MOD_RES
<222> LOCATION: (27)..(27)
```

-continued

```
<223> OTHER INFORMATION: Ser or Arg
<220> FEATURE:
<221> NAME/KEY: MOD_RES
<222> LOCATION: (65)..(65)
<223> OTHER INFORMATION: Glu or Asp
<220> FEATURE:
<221> NAME/KEY: MOD_RES
<222> LOCATION: (75)..(75)
<223> OTHER INFORMATION: Met or Leu
<220> FEATURE:
<221> NAME/KEY: MOD_RES
<222> LOCATION: (88)..(88)
<223> OTHER INFORMATION: Thr or Ala
<220> FEATURE:
<221> NAME/KEY: MOD_RES
<222> LOCATION: (91)..(91)
<223> OTHER INFORMATION: Val or Thr
<220> FEATURE:
<221> NAME/KEY: MOD_RES
<222> LOCATION: (101)..(101)
<223> OTHER INFORMATION: Asn or Gly
<220> FEATURE:
<221> NAME/KEY: MOD_RES
<222> LOCATION: (103)..(103)
<223> OTHER INFORMATION: Leu or Val
<220> FEATURE:
<221> NAME/KEY: MOD_RES
<222> LOCATION: (112)..(112)
<223> OTHER INFORMATION: Val or Ala

<400> SEQUENCE: 32

Met Xaa Thr Xaa Leu Phe Arg Trp Pro Val Arg Val Tyr Tyr Glu Asp
1               5                   10                  15

Thr Asp Ala Gly Gly Val Val Tyr His Ala Xaa Tyr Val Ala Phe Tyr
            20                  25                  30

Glu Arg Ala Arg Thr Glu Met Leu Arg His His His Phe Ser Gln Gln
        35                  40                  45

Val Leu Leu Ala Glu Arg Val Ala Phe Val Val Arg Lys Met Thr Val
    50                  55                  60

Xaa Tyr Tyr Ala Pro Ala Arg Leu Asp Asp Xaa Leu Glu Val Gln Thr
65                  70                  75                  80

Glu Ile Thr Ser Met Arg Gly Xaa Ser Leu Xaa Phe Thr Gln Arg Ile
                85                  90                  95

Val Asn Ala Glu Xaa Thr Xaa Leu Asn Glu Ala Glu Val Leu Ile Xaa
            100                 105                 110

Cys Val Asp Pro Ile Lys Met Lys Pro Arg Ala Leu Pro Lys Ser
        115                 120                 125
```